United States Patent
Gao et al.

(10) Patent No.: US 9,243,037 B2
(45) Date of Patent: Jan. 26, 2016

(54) GRAMICIDIN A MUTANTS THAT FUNCTION AS ANTIBIOTICS WITH IMPROVED SOLUBILITY AND REDUCED TOXICITY

(71) Applicant: Trustees of Boston College, Chestnut Hill, MA (US)

(72) Inventors: Jianmin Gao, Newton, MA (US); Fang Wang, Brighton, MA (US)

(73) Assignee: Trustees of Boston College, Chestnut Hill, MA (US)

(*) Notice: Subject to any disclaimer, the term of this patent is extended or adjusted under 35 U.S.C. 154(b) by 0 days.

(21) Appl. No.: 14/357,084

(22) PCT Filed: Nov. 9, 2012

(86) PCT No.: PCT/US2012/064364
§ 371 (c)(1),
(2) Date: May 8, 2014

(87) PCT Pub. No.: WO2013/071049
PCT Pub. Date: May 16, 2013

(65) Prior Publication Data
US 2015/0239936 A1 Aug. 27, 2015

Related U.S. Application Data

(60) Provisional application No. 61/557,990, filed on Nov. 10, 2011.

(51) Int. Cl.
| | | |
|---|---|---|
| *A01N 37/18* | (2006.01) | |
| *A61K 38/00* | (2006.01) | |
| *A61P 31/04* | (2006.01) | |
| *C07K 7/28* | (2006.01) | |
| *A61K 38/10* | (2006.01) | |
| *A01N 43/38* | (2006.01) | |

(52) U.S. Cl.
CPC . *C07K 7/28* (2013.01); *A01N 43/38* (2013.01); *A61K 38/10* (2013.01); *A61K 38/00* (2013.01)

(58) Field of Classification Search
None
See application file for complete search history.

(56) References Cited

U.S. PATENT DOCUMENTS

| | | |
|---|---|---|
| 5,741,712 A | 4/1998 | Cornell et al. |
| 6,358,921 B1 | 3/2002 | Kondejewski et al. |
| 2011/0046020 A1 | 2/2011 | Yang et al. |

FOREIGN PATENT DOCUMENTS

WO 2008/134544 11/2008

OTHER PUBLICATIONS

Solovskij et al. Polymer water-soluble derivatives of polypeptide antibiotic, gramicidin-S based on reactive copolymers of N-(2-hydroxypropyl)methacrylamide. J Controlled Release, 1999. vol. 58, pp. 1-8.*
Fernandez-Reyes et al. Lysine N-epsilon-Trimethylation, a Tool for Improving the Selectivity of Antimicrobial Peptides. J Med Chem, 2010. vol. 53, pp. 5587-5596.*
Pfeifer et al. Crown Ether-Gramicidin Hybrid Ion Channels: Dehydration-Assisted Ion Selectivity. Angew. Chem. Int. Ed., 2006. vol. 45, pp. 501-504.*
Jude et al., Biochemistry, 38(3):1030-1039 (1999). "Modulation of Gramicidin Channel Structure and Function by the Aliphatic 'Spacer' Residues 10, 12, and 14 between the Tryptophans +."
Orwa et al., Chromatographia, 53(1-2):17-21 (2001). "Liquid Chromatography of gramicidin."
Rokitskaya et al., European Biophysics Journal; With Biophysics Letters, Springer, Berlin, DD, 41(2):129-138 (2011). "The ph-dependent induction of lipid membrane ionic permeability by N-terminally lysine-substituted analogs of gramicidin A."
Separovic et al., Biochimicia Et Biophysica Acta (BBA)—Biomembranes, 1416(2):48-56 (1999). "NMR structure of C-terminally tagged gramicidin channels."
Wang et al., Chembiochem, 13(1):51-55 (2011). "Solubilized Gramicidin A as Potential Systemic Antibiotics."
Bamberg et al., "Single-Channel Parameters of Gramicidin A, B and C", Biochimica et Biphysica Acta 419:223-228 (1976).
Becker et al., "Amino acid sequence modulation of gramicidin channel function: effects of tryptophan-to-phenylalanine substitutions on the single-channel conductance and duration", Biochemistry 30(36):8830-8839 (1991).
Fonseca et al., "Gramicidin channels that have no tryptophan residues", Biochemistry 31(23):5340-5350 (1992).
Hessa et al., "Molecular code for transmembrane-helix recognition by the Sec61 translocon", Nature 450 (7172):1026-1030 (2007).
Killian J.A. & von Heijne G., "How proteins adapt to a membrane-water interface", Trends Biochem Sci 25 (9):429-434 (2000).
Koeppe et al., "Engineering the gramicidin channel", Annu. Rev. Biophys. Biomol. Struct. 25:231-258 (1996).
Koeppe et al., "Design and characterization of gramicidin channels with side chain or backbone mutations", Novartis Found Symp 225: 44-55 (1999).
Koeppe et al., "Neighboring aliphatic/aromatic side chain interactions between residues 9 and 10 in gramicidin channels", Biochemistry 39(9):2235-2242 (2000).
Koeppe., "Chapter 2 Molecular and Nano Tubes: Gramicidin Channels as Cation Nanotubes", pp. 11-30 (2011).

* cited by examiner

*Primary Examiner* — Marcela M Cordero Garcia
(74) *Attorney, Agent, or Firm* — Nixon Peabody LLP; Ronald I. Eisenstein; Leena H. Karttunen Contarino

(57) ABSTRACT

Described herein are antimicrobial peptides for use in pharmaceutical antibiotic compositions and methods of use thereof. These antimicrobial peptides are Gramicidin A (gA) peptide analogs that, in addition to having potent anti-microbial activity, have greatly increased solubility and significantly reduced toxicity in comparison to the wild-type Gramicidin A peptide.

31 Claims, 19 Drawing Sheets formyl-V-G-A-*d*L-A-*d*V-V-*d*V-W-*d*L-W-*d*L-W-*d*L-W-NHCH$_2$CH$_2$OH

*FIG. 1A*

*FIG. 1B* formyl-V-G-A-dL-A-dV-V-dV-W-dL-W-dL-W-dL-W-NHCH₂CH₂OH

10 *Lys*, 12 *Orn* and 14 *Dab*

GRAMICIDIN A MUTANTS THAT FUNCTION AS ANTIBIOTICS WITH IMPROVED SOLUBILITY AND REDUCED TOXICITY

CROSS-REFERENCE TO RELATED APPLICATIONS

This application is a 35 U.S.C. §371 National Phase Entry Application of International Application No. PCT/US12/64364 filed Nov. 9, 2012, and which claims benefit under 35 U.S.C. §119(e) of U.S. Provisional Application Ser. No. 61/557,990 filed Nov. 10, 2011, the contents of which are incorporated herein by reference in their entireties.

SEQUENCE LISTING

The instant application contains a Sequence Listing which has been submitted electronically in ASCII format via EFS-Web and is hereby incorporated by reference in its entirety. Said ASCII copy, created on Sep. 23, 2014, is named 51566-072242-US SL.txt and is 6,085 bytes in size.

FIELD OF THE INVENTION

The invention generally relates to Gramicidin A analog peptides and derivatives thereof with improved solubility and reduced toxicity and uses thereof as systemic antibiotics.

BACKGROUND

Bacteria rapidly develop resistance to antibiotic drugs within years of first clinical use. Antibiotic resistance can be acquired by horizontal gene transfer or result from persistence, in which a small fraction of cells in a population exhibits a non-inherited tolerance to antimicrobials. Antimicrobial drug discovery is increasingly lagging behind the evolution of antibiotic resistance.

Bacterial infections are responsible for significant morbidity and mortality in clinical settings. Though the advent of antibiotics has reduced the impact of bacterial diseases on human health, the constant evolution of antibiotic resistance poses a serious challenge to the usefulness of today's antibiotic drugs. Infections that would have been easily cured by antibiotics in the past are now able to survive to a greater extent, resulting in sicker patients and longer hospitalizations. The economic impact of antibiotic-resistant infections is estimated to be between US $5 billion and US $24 billion per year in the United States alone. Resistance to antibiotic drugs develops and spreads rapidly, often within a few years of first clinical use.

SUMMARY OF THE INVENTION

Provided herein are strategically designed anti-microbial peptide analogs and derivatives of Gramicidin A having increased solubility and reduced toxicity to host cells, such as mammalian cells. By analyzing the dimeric channel structure of wild-type Gramicidin A having SEQ ID NO: 2, key residues of wild-type Gramicidin A (SEQ ID NO: 2) were identified as ideal for mutation or modification. By strategically incorporating cationic residues at one or more of the d-Leucines of SEQ ID NO: 2, channel formation and bacterial specificity is maintained, while providing greatly increased solubility, as demonstrated herein. Importantly, and in contrast to wild-type Gramicidin A, the Gramicidin A peptide analogs and derivatives described herein have greatly increased water solubility and significantly decreased cytotoxicity of non-bacterial cells, such as mammalian cells. In addition, as demonstrated herein, the therapeutic utility of solubilized gramicidin A as systemic antibiotics can be further fine tuned by $N^\epsilon$-trialkylation, such as $N^\epsilon$-trimethylation, of one or more cationic residues, such as lysine. Accordingly, the novel Gramicidin A peptide analogs described herein are useful as systemic antibiotics and in methods of use thereof.

The Gramicidin A peptide analogs and derivatives disclosed herein have potent antimicrobial activities and can be useful against, for example, bacteria, such as gram-positive bacteria, fungi, and other pathogens. Antimicrobial peptides that work directly on cell membranes, like gramicidin A, are known to be more difficult for bacterial cells to develop resistance. These peptide analogs and derivatives are effective compounds for use in human and/or veterinary medicine, or as agents in agricultural, food science, or industrial applications. The Gramicidin A peptide analogs and derivatives described herein are useful for inhibiting the growth of bacteria such as, *Bacillus* species, *Staphylococcus* species, and *Streptococcus* species, and for treating infections in humans or animals caused by these and other organisms.

Accordingly, provided herein, in some aspects, are antimicrobial compositions comprising at least one Gramicidin A peptide analog or derivative having reduced cytotoxicity and increased solubility relative to wild-type Gramicidin A having the amino acid sequence of SEQ ID NO: 2.

In some embodiments of these aspects and all such aspects described herein, the at least one Gramicidin A peptide analog or derivative comprises the amino acid sequence of SEQ ID NO: 2 having one or more of the d-Leucine amino acids at positions 10, 12, or 14 replaced or substituted. In some such embodiments, the one or more of the d-Leucine amino acids are replaced or substituted with a cationic amino acid residue. In some such embodiments, the cationic amino acid is d-lysine or d-arginine.

In some embodiments of these aspects and all such aspects described herein, the at least one Gramicidin A peptide analog or derivative comprises the amino acid sequence of SEQ ID NO: 2 having at least two of the d-Leucine amino acids at positions 10, 12, or 14 replaced or substituted. In some such embodiments, the at least d-Leucine amino acids are replaced or substituted with a cationic amino acid. In some such embodiments, the cationic amino acid is d-lysine or d-arginine.

In some embodiments of these aspects and all such aspects described herein, the at least one Gramicidin A peptide analog or derivative comprises the amino acid sequence of SEQ ID NO: 2 having all three of the d-Leucine amino acids at positions 10, 12, and 14 replaced or substituted. In some such embodiments, the all three of the d-Leucine amino acids at positions 10, 12, and 14 are replaced or substituted with a cationic amino acid. In some such embodiments, the cationic amino acid is d-lysine or d-arginine.

In some embodiments of these aspects and all such aspects described herein, the solubility of the Gramicidin A peptide analog or derivative is increased relative to wild-type Gramicidin A by at least 10-fold.

In some embodiments of these aspects and all such aspects described herein, the cytotoxicity of the Gramicidin A peptide analog or derivative is reduced relative to wild-type Gramicidin A by at least 2-fold.

In some embodiments of these aspects and all such aspects described herein, the at least one Gramicidin A peptide analog or derivative comprises an amino acid sequence of formyl-V-G-A-dL-A-dV-V-dV-W-dK-W-dL-W-dL-W—NHCH$_2$CH$_2$OH (SEQ ID NO: 3). In some embodiments of these aspects and all such aspects described herein, the at least one Gramicidin A peptide analog or derivative consists essentially of an amino acid sequence of SEQ ID NO: 3. In some embodiments of these aspects and all such aspects described herein, the at least one Gramicidin A peptide analog or derivative consists of an amino acid sequence of SEQ ID NO: 3.

In some embodiments of these aspects and all such aspects described herein, the at least one Gramicidin A peptide analog or derivative comprises an amino acid sequence of formyl-V-G-A-dL-A-dV-V-dV-W-dL-W-dL-W-dK-W—NHCH$_2$CH$_2$OH (SEQ ID NO: 4). In some embodiments of these aspects and all such aspects described herein, the at least one Gramicidin A peptide analog or derivative consists essentially of an amino acid sequence of SEQ ID NO: 4. In some embodiments of these aspects and all such aspects described herein, the at least one Gramicidin A peptide analog or derivative consists of an amino acid sequence of SEQ ID NO: 4.

In some embodiments of these aspects and all such aspects described herein, the at least one Gramicidin A peptide analog or derivative comprises an amino acid sequence of formyl-V-G-A-dL-A-dV-V-dV-W-dK-W-dL-W-dK-W—NHCH$_2$CH$_2$OH (SEQ ID NO: 5). In some embodiments of these aspects and all such aspects described herein, the at least one Gramicidin A peptide analog or derivative consists essentially of an amino acid sequence of SEQ ID NO: 5. In some embodiments of these aspects and all such aspects described herein, the at least one Gramicidin A peptide analog or derivative consists of an amino acid sequence of SEQ ID NO: 5.

In some embodiments of these aspects and all such aspects described herein, the at least one Gramicidin A peptide analog or derivative comprises an amino acid sequence of formyl-V-G-A-dL-A-dV-V-dV-W-dK-W-dK-W-dL-W—NHCH$_2$CH$_2$OH (SEQ ID NO: 6). In some embodiments of these aspects and all such aspects described herein, the at least one Gramicidin A peptide analog or derivative consists essentially of an amino acid sequence of SEQ ID NO: 6. In some embodiments of these aspects and all such aspects described herein, the at least one Gramicidin A peptide analog or derivative consists of an amino acid sequence of SEQ ID NO: 6.

In some embodiments of these aspects and all such aspects described herein, the at least one Gramicidin A peptide analog or derivative comprises an amino acid sequence of formyl-V-G-A-dL-A-dV-V-dV-W-dK-W-dK-W-dK-W—NHCH$_2$CH$_2$OH (SEQ ID NO: 7). In some embodiments of these aspects and all such aspects described herein, the at least one Gramicidin A peptide analog or derivative consists essentially of an amino acid sequence of SEQ ID NO: 7. In some embodiments of these aspects and all such aspects described herein, the at least one Gramicidin A peptide analog or derivative consists of an amino acid sequence of SEQ ID NO: 7.

In some embodiments of these aspects and all such aspects described herein, the at least one Gramicidin A peptide analog or derivative comprises an amino acid sequence of formyl-V-G-A-dL-A-dV-V-dV-W-dR-W-dR-W-dR-W—NHCH$_2$CH$_2$OH (SEQ ID NO: 8). In some embodiments of these aspects and all such aspects described herein, the at least one Gramicidin A peptide analog or derivative consists essentially of an amino acid sequence of SEQ ID NO: 8. In some embodiments of these aspects and all such aspects described herein, the at least one Gramicidin A peptide analog or derivative consists of an amino acid sequence of SEQ ID NO: 8.

In some embodiments of these aspects and all such aspects described herein, one or more of the d-Leucine residues at positions 10 or 14 of wild-type Gramicidin A or SEQ ID NO: 2 is replaced with a Nε-trialkylated cationic residue. In some such embodiments, the Nε-trialkylated cationic residue is Nε-trialkylated lysine. In some embodiments of these aspects and all such aspects described herein, a d-Leucine residue at position 10 of wild-type Gramicidin A or SEQ ID NO: 2 is replaced with a Nε-trialkylated lysine. In some embodiments of these aspects and all such aspects described herein, a d-Leucine residue at position 14 of wild-type Gramicidin A or SEQ ID NO: 2 is replaced with a Nε-trialkylated lysine. In some embodiments of these aspects and all such aspects described herein, d-Leucine residues at positions 10 and 14 of wild-type Gramicidin A or SEQ ID NO: 2 are both replaced with a Nε-trialkylated lysine.

In some embodiments of these aspects and all such aspects described herein, one or more of the d-Leucine residues at positions 10 or 14 of wild-type Gramicidin A or SEQ ID NO: 2 is replaced with a Nε-trimethylated cationic residue. In some such embodiments, the Nε-trimethylated cationic residue is Nε-trimethylated lysine. In some embodiments of these aspects and all such aspects described herein, a d-Leucine residue at position 10 of wild-type Gramicidin A or SEQ ID NO: 2 is replaced with a Nε-trimethylated lysine. In some embodiments of these aspects and all such aspects described herein, a d-Leucine residue at position 14 of wild-type Gramicidin A or SEQ ID NO: 2 is replaced with a Nε-trimethylated lysine. In some embodiments of these aspects and all such aspects described herein, d-Leucine residues at positions 10 and 14 of wild-type Gramicidin A or SEQ ID NO: 2 are both replaced with a Nε-trimethylated lysine.

In some embodiments of these aspects and all such aspects described herein, one or more of the d-Leucine residues at positions 10 or 14 of wild-type Gramicidin A or SEQ ID NO: 2 is replaced with a Nε-trialkylated ornithine residue. In some embodiments of these aspects and all such aspects described herein, a d-Leucine residue at position 10 of wild-type Gramicidin A or SEQ ID NO: 2 is replaced with a Nε-trialkylated ornithine. In some embodiments of these aspects and all such aspects described herein, a d-Leucine residue at position 14 of wild-type Gramicidin A or SEQ ID NO: 2 is replaced with a Nε-trialkylated ornithine. In some embodiments of these aspects and all such aspects described herein, d-Leucine residues at positions 10 and 14 of wild-type Gramicidin A or SEQ ID NO: 2 are both replaced with a Nε-trialkylated ornithine.

In some embodiments of these aspects and all such aspects described herein, one or more of the d-Leucine residues at positions 10 or 14 of wild-type Gramicidin A or SEQ ID NO: 2 is replaced with a Nε-trimethylated ornithine. In some embodiments of these aspects and all such aspects described herein, a d-Leucine residue at position 10 of wild-type Gramicidin A or SEQ ID NO: 2 is replaced with a Nε-trimethylated ornithine. In some embodiments of these aspects and all such aspects described herein, a d-Leucine residue at position 14 of wild-type Gramicidin A or SEQ ID NO: 2 is replaced with a Nε-trimethylated ornithine. In some embodiments of these aspects and all such aspects described herein, d-Leucine residues at positions 10 and 14 of wild-type Gramicidin A or SEQ ID NO: 2 are both replaced with a Nε-trimethylated ornithine.

In some embodiments of these aspects and all such aspects described herein, the anti-microbial compositions further comprise a pharmaceutically acceptable carrier.

In other aspects, provided herein are methods of inhibiting growth or replication of a microorganism. Such methods comprise contacting a biological sample or a surface with an anti-microbial composition comprising at least one Gramicidin A peptide analog or derivative having reduced cytotoxicity and increased solubility relative to wild-type Gramicidin A having the amino acid sequence of SEQ ID NO: 2, in an amount sufficient to inhibit growth or replication of the microorganism.

In some embodiments of these methods and all such methods described herein, the microorganism is a bacteria. In some such embodiments, the bacteria is a Gram-positive bacteria.

Also provided herein are methods of treating or inhibiting a microbial infection in a subject having or at risk for a microbial infection, comprising administering to the subject a therapeutically effective amount of an anti-microbial composition comprising at least one Gramicidin A peptide analog or derivative having reduced cytotoxicity and increased solubility relative to wild-type Gramicidin A having the amino acid sequence of SEQ ID NO: 2.

In some embodiments of these methods and all such methods described herein, the microbial infection is a bacterial infection. In some such embodiments, the bacterial infection is caused by a Gram-positive bacteria.

In some embodiments of these methods and all such methods described herein, the methods further comprise the step of selecting the subject having or at risk for a microbial infection.

In some embodiments of these methods and all such methods described herein, the at least one Gramicidin A peptide analog or derivative comprises the amino acid sequence of SEQ ID NO: 2 having one or more of the d-Leucine amino acids at positions 10, 12, or 14 replaced or substituted. In some such embodiments, the one or more of the d-Leucine amino acids are replaced or substituted with a cationic amino acid residue. In some such embodiments, the cationic amino acid is d-lysine or d-arginine.

In some embodiments of these methods and all such methods described herein, the at least one Gramicidin A peptide analog or derivative comprises the amino acid sequence of SEQ ID NO: 2 having at least two of the d-Leucine amino acids at positions 10, 12, or 14 replaced or substituted. In some such embodiments, the at least d-Leucine amino acids are replaced or substituted with a cationic amino acid. In some such embodiments, the cationic amino acid is d-lysine or d-arginine.

In some embodiments of these methods and all such methods described herein, the at least one Gramicidin A peptide analog or derivative comprises the amino acid sequence of SEQ ID NO: 2 having all three of the d-Leucine amino acids at positions 10, 12, and 14 replaced or substituted. In some such embodiments, the all three of the d-Leucine amino acids at positions 10, 12, and 14 are replaced or substituted with a cationic amino acid. In some such embodiments, the cationic amino acid is d-lysine or d-arginine.

In some embodiments of these methods and all such methods described herein, the solubility of the Gramicidin A peptide analog or derivative is increased relative to wild-type Gramicidin A by at least 10-fold.

In some embodiments of these methods and all such methods described herein, the cytotoxicity of the Gramicidin A peptide analog or derivative is reduced relative to wild-type Gramicidin A by at least 2-fold.

In some embodiments of these methods and all such methods described herein, the at least one Gramicidin A peptide analog or derivative comprises an amino acid sequence of formyl-V-G-A-dL-A-dV-V-dV-W-dK-W-dL-W-dL-W—NHCH$_2$CH$_2$OH (SEQ ID NO: 3). In some embodiments of these methods and all such methods described herein, the at least one Gramicidin A peptide analog or derivative consists essentially of an amino acid sequence of SEQ ID NO: 3. In some embodiments of these methods and all such methods described herein, the at least one Gramicidin A peptide analog or derivative consists of an amino acid sequence of SEQ ID NO: 3.

In some embodiments of these methods and all such methods described herein, the at least one Gramicidin A peptide analog or derivative comprises an amino acid sequence of formyl-V-G-A-dL-A-dV-V-dV-W-dL-W-dL-W-dK-W—NHCH$_2$CH$_2$OH (SEQ ID NO: 4). In some embodiments of these methods and all such methods described herein, the at least one Gramicidin A peptide analog or derivative consists essentially of an amino acid sequence of SEQ ID NO: 4. In some embodiments of these methods and all such methods described herein, the at least one Gramicidin A peptide analog or derivative consists of an amino acid sequence of SEQ ID NO: 4.

In some embodiments of these methods and all such methods described herein, the at least one Gramicidin A peptide analog or derivative comprises an amino acid sequence of formyl-V-G-A-dL-A-dV-V-dV-W-dK-W-dL-W-dK-W—NHCH$_2$CH$_2$OH (SEQ ID NO: 5). In some embodiments of these methods and all such methods described herein, the at least one Gramicidin A peptide analog or derivative consists essentially of an amino acid sequence of SEQ ID NO: 5. In some embodiments of these methods and all such methods described herein, the at least one Gramicidin A peptide analog or derivative consists of an amino acid sequence of SEQ ID NO: 5.

In some embodiments of these methods and all such methods described herein, the at least one Gramicidin A peptide analog or derivative comprises an amino acid sequence of formyl-V-G-A-dL-A-dV-V-dV-W-dK-W-dK-W-dL-W—NHCH$_2$CH$_2$OH (SEQ ID NO: 6). In some embodiments of these methods and all such methods described herein, the at least one Gramicidin A peptide analog or derivative consists essentially of an amino acid sequence of SEQ ID NO: 6. In some embodiments of these methods and all such methods described herein, the at least one Gramicidin A peptide analog or derivative consists of an amino acid sequence of SEQ ID NO: 6.

In some embodiments of these methods and all such methods described herein, the at least one Gramicidin A peptide analog or derivative comprises an amino acid sequence of formyl-V-G-A-dL-A-dV-V-dV-W-dK-W-dK-W-dK-W—NHCH$_2$CH$_2$OH (SEQ ID NO: 7). In some embodiments of these methods and all such methods described herein, the at least one Gramicidin A peptide analog or derivative consists essentially of an amino acid sequence of SEQ ID NO: 7. In some embodiments of these methods and all such methods described herein, the at least one Gramicidin A peptide analog or derivative consists of an amino acid sequence of SEQ ID NO: 7.

In some embodiments of these methods and all such methods described herein, the at least one Gramicidin A peptide analog or derivative comprises an amino acid sequence of formyl-V-G-A-dL-A-dV-V-dV-W-dR-W-dR-W-dR-W—NHCH$_2$CH$_2$OH (SEQ ID NO: 8). In some embodiments of these methods and all such methods described herein, the at least one Gramicidin A peptide analog or derivative consists essentially of an amino acid sequence of SEQ ID NO: 8. In some embodiments of these methods and all such methods described herein, the at least one Gramicidin A peptide analog or derivative consists of an amino acid sequence of SEQ ID NO: 8.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "antimicrobial" or "antibiotic" means that a Gramicidin A peptide analog or derivative is capable of killing a microorganism and/or reducing or preventing growth of a microorganism. Methods for determining the antimicrobial activity of a peptide are known to those of ordinary skill in the art and some such methods are described herein in the Examples. The terms "antimicrobial activity," "microbicidal," and "microbistatic" refer to the ability of a Gramicidin A peptide analog or derivative described herein to modify a function or metabolic process of a target microorganism, for example so as to at least partially affect replication, vegetative growth, toxin production, survival, viability in a quiescent state, or other attribute. Bacteria to be inhibited or killed using the compositions and method described herein can include gram-negative and gram-positive bacteria, in addition to organisms classified in orders of the class Mollicutes and the like, such as species of the *Mycoplasma* and *Acholeplasma* genera. Examples of gram-positive bacteria include, but are not limited to, *Staphylococcus aureus*, *Staphylococcus epidermis*, *Streptococcus agalactiae*, Group A *streptococcus*, *Streptococcus pyogenes*, *Enterococcus faecalis*, Group B gram-positive *streptococcus*, *Corynebacterium xerosis*, and *Listeria monocytogenes*. Specific examples of gram-negative bacteria include, but are not limited to, *Escherichia coli*, *Acinetobacter baumannii*, *Pseudomonas aeruginosa*, *Salmonella*, *Hemophilus influenza*, *Neisseria*, *Vibrio cholerae*, *Vibrio parahaemolyticus* and *Helicobacter pylori*. Examples of fungi can include yeasts, such as *Candida albicans*. Examples of viruses can include measles virus, herpes simplex virus (HSV-1 and -2), herpes family members (HIV, hepatitis C, vesicular, stomatitis virus (VSV), visna virus, and cytomegalovirus (CMV). Examples of protozoa can include *Giardia*.

The terms "Gramicidin A," "wild-type Gramicidin A," "gA," or "wild-type gA," as used herein, refer to the endogenous fifteen-residue linear peptide isolated from *Bacillus brevis* having the amino acid sequence of formyl-V-G-A-dL-A-dV-V-dV-W-dL-W-dL-W-dL-W—NHCH$_2$CH$_2$OH (SEQ ID NO: 2).

As used herein, the terms "Gramicidin A analog" or "Gramicidin A variant" shall be taken to mean a Gramicidin A peptide that is modified to comprise one or more naturally-occurring and/or non-naturally-occurring amino acids, provided that the peptide analog is capable of reducing or preventing growth of a microorganism or killing a microorganism, as described herein. For example, the term "analog" encompasses an inhibitory peptide comprising one or more conservative amino acid changes. The term "analog" also encompasses a peptide comprising, for example, one or more D-amino acids, as described herein. Such an analog has the additional characteristic of, for example, protease resistance. Gramicidin A peptide analogs can be prepared by, for example, peptide synthesis. Such modifications include, for example, deletions from, and/or insertions into and/or substitutions of, residues within the amino acid sequence of the Gramicidin A peptide of SEQ ID NO: 2. Any combination of deletion, insertion, and substitution is made to arrive at the final peptide variant, provided that the final peptide variant possesses the desired characteristics, e.g., is anti-microbial, has low cellular cytotoxicity, and/or has high solubility.

As used herein the term "Gramicidin A derivative" refers to a peptide that is derived from an anti-microbial Gramicidin A peptide analog as described herein, e.g., a fragment or processed form of the peptide analog, and includes peptides which have been chemically modified by techniques such as adding additional side chains, ubiquitination, labeling, pegylation (derivatization with polyethylene glycol), and insertion, deletion or substitution of amino acids, including insertion, deletion and substitution of amino acids and other molecules (such as amino acid mimetics or unnatural amino acids) that do not normally occur in the peptide sequence of the Gramicidin A peptide analog that is basis of the derivative, for example but not limited to insertion of ornithine, which do not normally occur in human proteins. The term "derivative" is also intended to encompass all modified variants of the antimicrobial peptides analogs, functional derivatives, analogues and fragments thereof, as well as peptides with substantial identity as compared to the reference peptide to which they refer to. The term "derivative" also encompasses fusion proteins or fusion polypeptides comprising a peptide analog as described herein. The term "derivative" also encompasses a derivatized peptide, such as, for example, a peptide modified to contain one or more-chemical moieties other than an amino acid. The chemical moiety can be linked covalently to the peptide, e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide analog or derivative.

The term "amino acid," as used herein, is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g. diamino butyric acid and diamino propionic acid and the like. In the context of a peptide, an amino acid is synonymous with amino acid residue, as understood by one of ordinary skill in the art.

As used herein, by "reduced toxicity" or "reduced cytoxicity" is meant that a Gramicidin A peptide analog or derivative thereof has reduced toxicity to mammalian cells relative to the wild-type Gramicidin A peptide. As used herein, the term "reduced toxicity" indicates that a peptide or analog or derivative thereof does not induce or decreases the incidence or degree of one or more adverse response(s) in a subject or in a cell, tissue or organ of a subject to which it is administered relative to the wild-type Gramicidin A peptide. For example, ideally a Gramicidin A peptide analog or derivative described herein does not cause dysfunction of an organ or a system of organs or cause cell death. For example, an antimicrobial Gramicidin A peptide analog or derivative thereof is not nephrotoxic and/or is not neurotoxic and/or does not cause rhabdomyolysis and/or does not cause seizures and/or does not cause cardiac arrhythmia and/or does not have a myelosuppressive effect and/or does not cause diarrhea and/or does not cause anaphylaxis and/or does not cause significant levels of hemolysis, which may result in hemolytic anemia. Methods for comparing and determining toxicity of a Gramicidin A peptide analog or derivative thereof relative to the wild-type Gramicidin A peptide are known to the skilled artisan and are described herein.

The ability of a Gramicidin A peptide analog or derivative to induce lysis of red blood cells or hemolysis is an exemplary way of assessing cellular toxicity of a peptide. Accordingly, in some embodiments of the aspects described herein, a Gramicidin A peptide analog or derivative has a minimal hemolytic concentration that is greater than that that of the wild-type Gramicidin A, under the same conditions. As used herein, the terms "minimal hemolytic concentration" or "MHC" refer to the lowest concentration of a Gramicidin A peptide analog or derivative required to cause hemolysis of blood cells. MHC can be determined with red blood cells (RBC) from various species including human red blood cells (hRBC), as described herein. "$HC_{50}$," as used herein, refers to the peptide concentration that causes 50% lysis or 50% hemoglobin leakage of human red blood cells relative to cell lysis by a 1% Triton-X solution.

The ability of a Gramicidin A peptide analog or derivative to induce potassium leakage from red blood cells is another exemplary way of assessing cellular toxicity of a peptide. Accordingly, in some embodiments of the aspects described herein, a Gramicidin A peptide analog or derivative has a minimal $KC_{50}$ value that is greater than that that of the wild-type Gramicidin A peptide under the same conditions. As used herein, the terms "minimal $KC_{50}$" or "minimal potassium leakage activity" refer to the lowest concentration of a Gramicidin A peptide analog or derivative required to cause 50% $K^+$ ion leakage from red blood cells relative to $K^+$ ion leakage by a 1% Triton-X solution.

A Gramicidin A peptide analog or derivative described herein preferably has increased solubility relative to the wild-type Gramicidin A peptide of SEQ ID NO: 2. As used herein, "solubility" or "water solubility" refers to the ability of or degree to which a peptide analog or derivative can dissolve in an aqueous solution, under specific conditions. An "aqueous solution" or "aqueous environment," as used herein, is a water based environment, including salt solutions and plasma and water-based gels and pharmaceutical excipients. Such an environment may or may not include surfactants or amphiphilic compounds for solubilizing hydrophobes. Assays to measure solubility are well-known to those of ordinary skill in the art, and are described herein. For example, the solubility of a Gramicidin A peptide analog or derivative in a given aqueous buffer can be measured by monitoring tryptophan absorbance, as shown in, for example, FIG. 5.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a Gramicidin A peptide analog described herein).

Accordingly, as used herein, the phrase "inhibiting growth or replication of a microorganism" means to inhibit the replication or growth of the particular microorganism by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a Gramicidin A peptide analog described herein). Assays by which to measure and assess growth or replication of a microorganism are known to those of ordinary skill in the art, and are described herein.

As used herein, the phrase "treating or inhibiting a microbial infection" means to inhibit the replication of the particular microorganism causing the infection, to inhibit transmission of the microorganism, or to prevent the microorganism from establishing itself in its host, and to ameliorate or alleviate the symptoms of the disease caused by the infection. The treatment is considered therapeutic if there is a reduction in microorganism load, microorganism replication, microorganism counts or cell numbers, decrease in mortality, decrease in symptoms of the infection, such as a fever, and/or morbidity of a subject.

The terms "subject" and "individual" are used interchangeably herein, and refer to an animal, for example a human, that a microorganism that is inhibited by a Gramicidin A peptide analog or derivative is capable of infecting, and/or a recipient of the Gramicidin A peptide analogs and derivatives described herein, e.g., SEQ ID NO: 3-SEQ ID NO: 8. For treatment of those microbial infections that are specific for a specific animal, such as a human subject, the term "subject" refers to that specific animal. The terms 'non-human animals' and 'non-human mammals' are used interchangeably herein, and include, for example, mammals such as rats, mice, rabbits, sheep, cats, dogs, cows, pigs, and non-human primates. A subject that has a microbial infection is a subject having objectively measurable cells of the microorganism (e.g., bacterial cells, fungal cells) or cells infected with the microorganism (e.g., virus) present in the subject's body. Subjects that have increased risk for a microbial infection, or are at risk for a microbial infection include, but are not limited to, subjects with possible exposure to the microorganism, such as, for example, members of the armed or diplomatic services, a subject who has traveled recently to a region in which the microorganism is endemic, a hospitalized subject, a subject having had a surgery, etc.

The "therapeutically effective amount" of a Gramicidin A peptide analog or Gramicidin A peptide analog derivative having reduced cytotoxicity and increased solubility relative to wild-type Gramicidin A described herein is the minimum amount necessary to, for example, increase the time of survival of the subject, to inhibit or prevent gene expression of the microorganism, replication of the microorganism, transmission of the microorganism, or to treat or prevent the occurrence or recurrence of an infection by the microorganism. Accordingly, the "therapeutically effective amount" to be administered to a subject is governed by such considerations, and, as used herein, refers to the minimum amount necessary to prevent, ameliorate, or treat, or stabilize, a disorder or condition mediated by an infection by a microorganism.

The term "bacteria" as used herein is intended to encompass all variants of bacteria, for example, prokaryotic organisms and cyanobacteria. Accordingly, bacterial infections to be treated using the compositions and methods described herein include, but are not limited to, infections caused by gram-positive bacteria such as, but not limited to, *Bacillus cereus, Bacillus anbhracis, Bacillus cereus, Bacillus anthracia, Clostridium botulinum, Clostridium difficle, Clostridium tetani, Clostridium perfringens, Corynebacteria diptheriae, Enterococcus* (*Streptococcus* D), *Listeria monocytogenes*, Pneumococcal infections (*Streptococcus pneumoniae*), Staphylococcal infections and Streptococcal infections; infections caused by Gram-negative bacteria such as, but not limited to, *Bacteroides, Bordetella pertussis, Brucella,*

*Campylobacter* infections, enterohaemorrhagic *Escherichia coli* (EHEC/*E. coli* 0157:17) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp, *Pseudomonas aeruginosa, Salmonella* spp., *Shigella* spp., *Vibrio cholera* and *Yersinia*; infections caused by acid fast bacteria including, but not limited to, *Mycobacterium tuberculosis, Mycobacterium avium*-intracellulars, *Myobacterium johnei, Mycobacterium leprae,* atypical bacteria, *Chlamydia, Myoplasma, Rickettsia, Spirochetes, Treponema pallidum, Borrelia recurrentis, Borrelia burgdorfii* and *Leptospira icterohemorrhagiae* and other miscellaneous bacteria, including *Actinomyces* and *Nocardia*.

Examples of bacterial infections and situations in which such bacterial infections can occur that are not necessarily specific to a particular bacterial species, but encompassed by the term "bacterial infection," as used herein, include bacterial wound infections, such as in burn wound patients; mucosal infections, enteric infections, Bacteraemia and septic conditions, pneumonia, trachoma, onithosis, trichomoniasis and salmonellosis, especially in veterinary practice; urinary tract infections; post-surgery infections on or caused by invasive devises; endocarditis by intravenous administration of contaminated drug solutions; bacterial infections in patients with acquired immunodeficiency syndrome, cancer chemotherapy, steroid therapy, hematological malignancies, organ transplantation, renal replacement therapy, and other situations with severe neutropenia; community-acquired respiratory tract infections; meningitis; folliculitis and infections of the ear canal caused by contaminated waters; malignant otitis externa in the elderly and diabetics; osteomyelitis of the caleaneus in children; eye infections commonly associated with contaminated contact lens; Skin infections such as nail infections in people whose hands are frequently exposed to water; gastrointestinal tract infections; and muscoskeletal system infections.

The term "biological sample" as used herein refers to a cell or population of cells or a quantity of tissue or fluid from a subject or source, such as an environmental source or a food source, for example. In some embodiments the sample is isolated from or removed from a subject, but, in some embodiments, the term "biological sample" can also refer to cells or tissue analyzed in vivo, i.e. without removal from the subject. Often, a "biological sample" will contain cells from the animal, but the term can also refer to non-cellular biological material. The term biological sample encompasses cellular, tissue or fluid extracts, including, but not limited to, skin, plasma, serum, spinal fluid, lymph fluid, synovial fluid, urine, tears, blood cells, organs, tumors, and also to samples of in vitro cell culture constituents (including, but not limited to, conditioned medium resulting from the growth of cells (including prokaryotic and eukaryotic cells) in cell culture medium, recombinant cells, and cell components). Samples can comprise cellular or tissue explants obtained from an individual or organism during a medical procedure or intervention, such as a surgical procedure or biopsy. Samples from environmental sources are also included among "samples" to which the compositions and methods described herein can be applied.

The term "surface" used herein, refers to any surface whether medical or industrial, that provides an interface between a fluid, such as a liquid or air, and a solid. The interface between fluid and solid can be intermittent, and can be caused by flowing or stagnant fluid, aerosols, or other means for air-borne fluid exposure. A surface refers, in some embodiments, to a plane whose mechanical structure is compatible with the adherence of bacteria such as *S. aureus* and *Enterococcus* species. In the context of the compositions and methods described herein, the terminology "medical or veterinary surface" encompasses the inner and outer aspects of various instruments and devices, both disposable and non-disposable. Examples include the entire spectrum of medical devices.

As used herein, the terminology "surfaces found in medical environments" includes the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopaedic pins, plates and implants; catheters and other tubes (including urological and biliary tubes, endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Surfaces found in the medical environment also include the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilised drugs in nebulisers and of aesthetic agents. Also included are those surfaces intended as biological barriers to infectious organisms in medical settings, such as gloves, aprons and face-shields. Commonly used materials for biological barriers may be latex-based or non-latex based, such as vinyl. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

The practice of the methods described herein will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Polynucleotide Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). The practice of the methods described herein can also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456;

5,246,577; 5,126,025; 5,364,521; 4,985,129; as well as in U.S. patent application Ser. Nos. 10/113,034; 10/387,286; 10/719,185; 10/600,201; 10/752,123 and Ser. No. 10/719,746.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified herein, both supra and infra, are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

BRIEF DESCRIPTION OF THE DRAWINGS

FIG. 1A shows the amino acid sequence of Gramicidin A (SEQ ID NO: 2) (single letter codes, the D-amino acids were labeled by the italic "d") and cartoon representation of the β-helical dimeric channel (PDB: 1MAG, derived from solid-state NMR data in lipid bilayers), side view on the left and top view on the right. FIG. 1B depicts pore formation of Gramicidin A (gA): dimerization of gA via N-terminal hydrogen bonding in a lipid bilayer gives an open pore that spans across the bilayer.

FIG. 4A shows an apparent dissociation constants (Kd) of the gA variants presented as lipid/peptide ratios. FIG. 4B shows a concentration profile of gA-5 in inducing K+ leakage from the negative (POPC/PCPG) and neutral (POPC) vesicles.

FIG. 13A shows the amino acid sequence of wild-type gA (SEQ ID NO: 2) (single letter codes, the D-amino acids are labeled by the italic "d", the mutation positions are highlighted) and cartoon representation of the β-helical dimeric channel (PDB: 1MAG, derived from solid-state NMR data in lipid bilayers), side view on the left and top view on the right. FIG. 13B shows gA channel formation in lipids bilayer dimerization of gA via N-terminal hydrogen bonding (6 pairs) in a lipid bilayer gives an open pore that spans across the bilayer. The locations of the mutated residues were highlighted by orange side chain. The distance between the dL10 α-C and the boundary of the lipids bilayer is labeled in the left picture.

DETAILED DESCRIPTION

Figure 2:
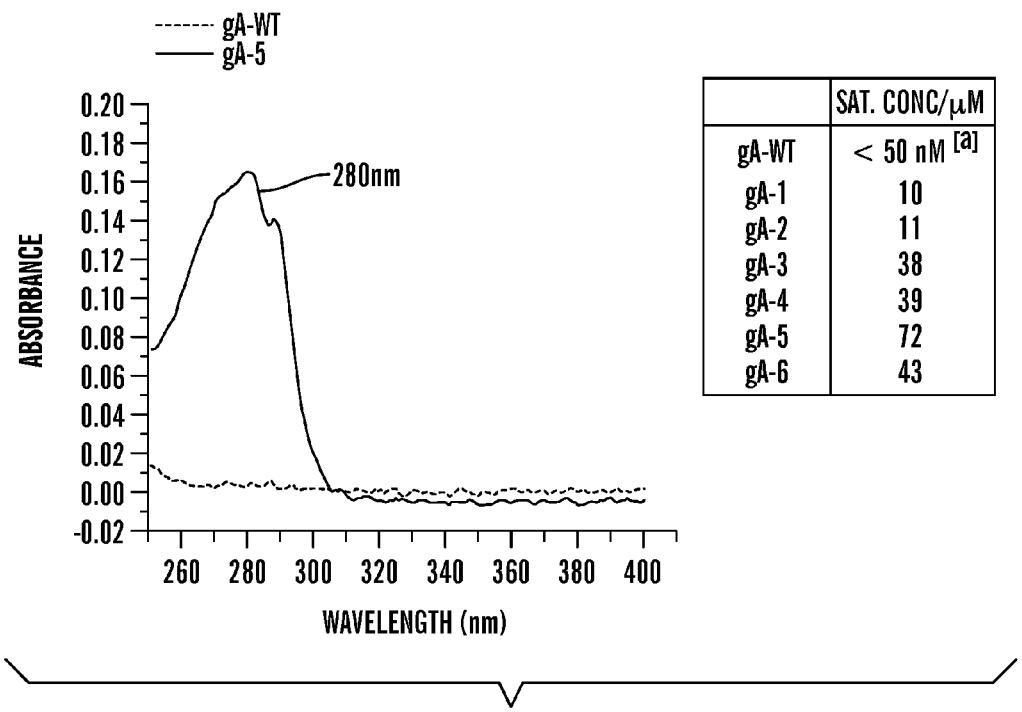
FIG. 2 demonstrates Trp absorption spectra of gA-WT and gA-5. Water solubility of gA variants is determined by Trp absorbance at 280 nm and summarized in the inserted table. Buffer used: 10 mM HEPES containing 1% DMSO. The solubility of gA-WT was obtained from reference [8].

Provided herein are novel antimicrobial peptides for use in pharmaceutical antibiotic compositions and methods of use thereof. These antimicrobial peptide are Gramicidin A (gA) peptide analogs that, in addition to having potent anti-microbial activity, have greatly increased solubility and significantly reduced toxicity in comparison to the wild-type Gramicidin A peptide. In addition, as demonstrated herein, the therapeutic utility of solubilized gramicidin A as systemic antibiotics can be further fine tuned by $N^\epsilon$-trialkylation, such as $N^\epsilon$-trimethylation, of one or more cationic residues, such as lysine. Accordingly, the gA peptide analogs provided herein can be used, for example, as systemic antibiotics in the treatment of infections mediated by, for example, gram-positive bacteria.

Gramicidin A Peptide Analogs and Derivatives Thereof

The rapid development of multidrug resistance by pathogenic bacteria poses a serious threat to the society and requires new antibiotics with different mechanisms of action. Recently, effort has been made in regard to developing membrane active peptides and their functional analogs as antibiotics. "Antimicrobial peptides" or "AMPs," as used herein, refer to a large collection of endogenous short peptides, of approximately 12-80 amino acids, that kill a wide spectrum of bacteria and serve as the frontline of the innate immune system. The majority of known AMPs display a positive net charge and an amphipathic structure. AMPs are different from conventional antibiotics, which typically target a specific step of biosynthesis, and are thought, without wishing to be bound or limited by theory, to function by disrupting the plasma membrane of bacterial cells. Because they disrupt the bacterial cell membranes, it is difficult for bacteria to acquire resistance. However, the development of AMPs into systemic antibiotics is slow and difficult because of their low efficacy, toxicity to non-bacterial cells, and limited tissue distribution.

The Gramicidins A, B, and C are a family of anti-microbial linear pentadecapeptides (i.e., 15 amino acid peptides) derived from the soil bacterial species Bacillus brevis having membrane lysis activity-collectively these peptides are known as Gramicidin D. These anti-microbial peptides act by decreasing permeability of bacterial cell membranes, thereby allowing inorganic monovalent cations (e.g., Na+) to travel through unrestricted, and hence destroying the ion gradient between the cytoplasm and the extracellular environment. The Gramicidins are polypeptides with alternating L-& D-amino acids, comprised of the general formula: formyl-X-G-A-dL-A-dV-V-dV-W-dL-Y-dL-L-W-dL-W—NHCH$_2$CH$_2$OH (SEQ ID NO: 1), where X and Y depend upon the gramicidin molecule. There exists valine and isoleucine variants of all three gramicidin species and 'X' can be either. The Y amino acid determines the nature of the three Gramicidins—in the place of Y Gramicidin A comprises Tryptophan, Gramicidin B comprises Phenylalanine, and Gramicidin C comprises Tyrosine. The alternating stereochemical configurations (in the form of D and L) of the amino acids are vital to the formation of the β-helix of these peptides. The chain of Gramicidin peptides assembles inside of the hydrophobic interior of the cellular lipid bilayer to form a β-helix. The helix itself is not long enough to span the membrane, but has been shown to dimerize to form an elongated channel needed to span the whole membrane.

Figures 1A, 1B:
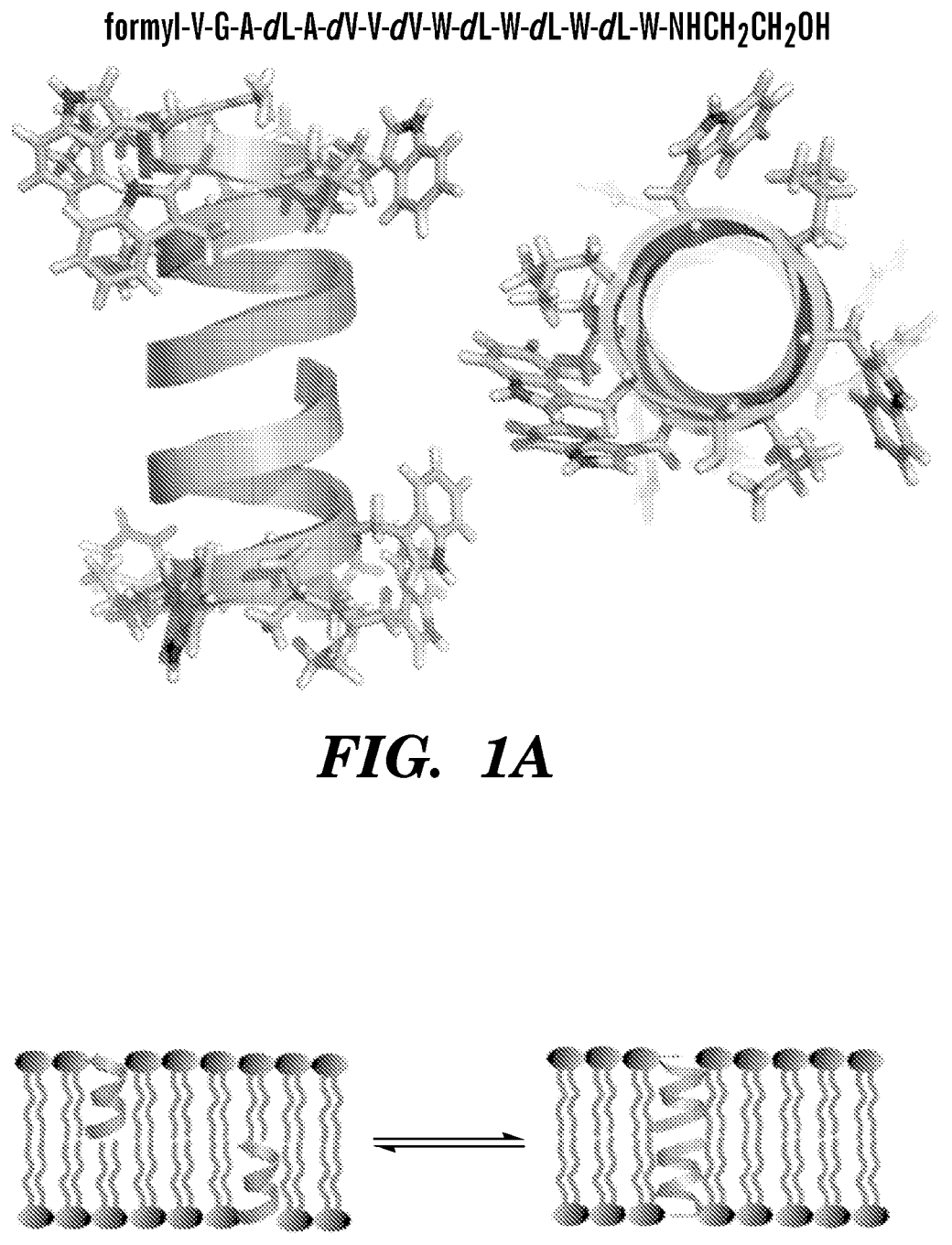

"Gramicidin A," "wild-type Gramicidin A," "gA," or "wild-type gA," as used herein, refer to the endogenous fifteen-residue linear peptide isolated from Bacillus brevis having the amino acid sequence of formyl-V-G-A-dL-A-dV-V-dV-W-dL-W-dL-W-dL-W—NHCH$_2$CH$_2$OH (SEQ ID NO: 2). Gramicidin A folds into a β-helix with an internal pore, as illustrated in FIG. 1A, and the length of the β-helix matches well with one leaflet of a membrane; inter-leaflet dimerization yields a transmembrane channel with a diameter of 4 Å (depicted in FIG. 1B). The channel formed by Gramicidin A allows facile diffusion of water and a selection of monovalent cations (e.g., Na+, K+), but it is impermeable to larger species including polyvalent cations. Due to the channel forming activity, gA has been demonstrated to have potent antibiotic activity. However, the peptide is essentially insoluble in water (<50 nM) and induces hemolysis under concentrations required to cause bacteria cell death. Consequently, its therapeutic usage has been limited, at best, to topical applications.

Provided herein are strategically designed anti-microbial peptide analogs of Gramicidin A. By analyzing the dimeric channel structure of wild-type Gramicidin A, key residues of wild-type Gramicidin A (SEQ ID NO: 2) were identified as ideal for mutation or modification. These residues, which correspond to the d-Leucines of wild-type gA (SEQ ID NO: 2), were replaced in various combinations with d-Lysines. The analyses revealed that the d-Leucine residues (amino acids 10, 12, and 14 of SEQ ID NO: 2) are highly suitable for mutation as they are located at the membrane-water interface, where charged side chains can be accommodated without altering the channel structure. By strategically incorporating cationic residues at one or more of the d-Leucines of SEQ ID NO: 2, channel formation and bacterial specificity is maintained, while providing greatly increased solubility, as demonstrated herein. Importantly, and in contrast to wild-type Gramicidin A, the Gramicidin A peptide analogs described herein have greatly increased water solubility, combined with significantly decreased cytotoxicity of non-bacterial cells.

Accordingly, the novel Gramicidin A peptide analogs described herein are useful as systemic antibiotics and in methods of use thereof.

As described herein, we have designed and developed a series of novel anti-microbial peptides that successfully mimic the function of the natural anti-microbial peptide Gramicidin A, but lack the poor water solubility and high cellular toxicity of wild-type Gramicidin A. These Gramicidin A peptide analogs not only had significant anti-bacterial activity against a variety of gram-positive bacteria, such as *B. subtilis, S. aureus*, and *S. pyogenes*, but had significantly reduced toxicity against non-bacterial membranes, as evidenced in hemolytic activity assays and toxicity assays involving mammalian cancer cells lines. Accordingly, the Gramicidin A peptide analogs and derivatives disclosed herein have potent antimicrobial activities and can be useful against, for example, bacteria, such as gram-positive bacteria, fungi, and other pathogens. These peptide analogs and derivatives are effective compounds for use in human and/or veterinary medicine, or as agents in agricultural, food science, or industrial applications. The Gramicidin A peptide analogs and derivatives described herein are useful for inhibiting the growth of bacteria such as, *Bacillus* species, *Staphylococcus* species, and *Streptococcus* species, for treating infections in humans or animals caused by these and other organisms. By substituting specific residues of wild-type gramicidin A, we have demonstrated that various parameters of Gramicidin A, such as solubility and cytotoxicity can be modulated, while maintaining anti-microbial activity. As is understood by one of ordinary skill in the art, increasing or decreasing one parameter, such as solubilty, can result in an undesired modulation of another parameter, such as anti-microbial activity. Accordingly, the Gramicidin A peptide analogs or derivatives having reduced cytotoxicity and increased solubility relative to wild-type Gramicidin A are tested for effects on all such parameters, and the Gramicidin A peptide analogs or derivatives having the desired combination of increases and decreases in the parameters necessary or optimal for therapeutic utility are selected.

Accordingly, in some aspects, provided herein are anti-microbial compositions comprising one or more Gramicidin A peptide analogs or derivatives having reduced cytotoxicity and increased solubility relative to wild-type Gramicidin A or SEQ ID NO: 2.

In some embodiments of these aspects and all such aspects described herein, one or more of the d-Leucine residues at positions 10, 12, or 14 of wild-type Gramicidin A or SEQ ID NO: 2 is replaced with a cationic residue. In some such embodiments, the cationic residue is d-Lysine. In some embodiments of these aspects and all such aspects described herein, one d-Leucine residue at any of positions 10, 12, or 14 of wild-type Gramicidin A or SEQ ID NO: 2 is replaced with a cationic residue. In some such embodiments, the cationic residue is d-Lysine. In some embodiments of these aspects and all such aspects described herein, two d-Leucine residues at any of positions 10, 12, or 14 of wild-type Gramicidin A or SEQ ID NO: 2 are replaced with a cationic residue. In some such embodiments, at least one cationic residue is d-Lysine. In some embodiments of these aspects and all such aspects described herein, each of the three d-Leucine residues at positions 10, 12, or 14 of wild-type Gramicidin A or SEQ ID NO: 2 is replaced with a cationic residue. In some such embodiments, at least one cationic residue is d-Lysine. In some other such embodiments, at least one cationic residue is arginine.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dK-W-dL-W-dL-W—NHCH$_2$CH$_2$OH (SEQ ID NO: 3 or gA-1). The gA-1 peptide analog has the d-Leucine at position 10 of SEQ ID NO: 2 replaced by d-Lysine. As described herein, the gA-1 peptide analog has a minimum inhibitory concentration (MIC) equivalent to that of wild-type Gramicidin A against *B. subtilis, S. Aureus*, and *S. Pyogenes*, while the peptide concentration required to cause 50% K$^+$ ion leakage relative to the lysis by a 1% TritonX-100 solution was ~100 fold greater than that of the wild-type Gramicidin A peptide of SEQ ID NO: 2. In addition, the water solubility of SEQ ID NO: 3 was shown to be ~200-fold higher than that of wild-type Gramicidin A (FIG. 2). In some embodiments, the Gramicidin A peptide analog having reduced cytotoxicity and increased solubility relative to wild-type Gramicidin A or SEQ ID NO: 2 consists essentially of SEQ ID NO: 3. In some embodiments, the Gramicidin A peptide analog having reduced cytotoxicity and increased solubility relative to wild-type Gramicidin A or SEQ ID NO: 2 consists of SEQ ID NO: 3.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dL-W-dK-W-dL-W—NHCH$_2$CH$_2$OH (SEQ ID NO: 4 or gA-2). The gA-2 peptide analog has the d-Leucine at position 12 of SEQ ID NO: 2 replaced by d-Lysine. As described herein, the gA-2 peptide analog has a minimum inhibitory concentration (MIC) equivalent to that of wild-type Gramicidin A against *B. subtilis, S. Aureus*, and *S. pyogenes*, while the peptide concentration required to cause 50% K$^+$ ion leakage relative to the lysis by a 1% TritonX-100 solution is ~100 fold greater than that of the wild-type Gramicidin A peptide of SEQ ID NO: 2. In addition, the water solubility of SEQ ID NO: 4 was shown to be ~200-fold higher than that of wild-type Gramicidin A (FIG. 2). In some embodiments, the Gramicidin A peptide analog having reduced cytotoxicity and increased solubility relative to wild-type Gramicidin A or SEQ ID NO: 2 consists essentially of SEQ ID NO: 4. In some embodiments, the Gramicidin A peptide analog having reduced cytotoxicity and increased solubility relative to wild-type Gramicidin A or SEQ ID NO: 2 consists of SEQ ID NO: 4.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dK-W-dL-W-dK-W—NHCH$_2$CH$_2$OH (SEQ ID NO: 5 or gA-3). The gA-3 peptide analog has the d-Leucine at positions 10 and 14 of SEQ ID NO: 2 replaced by d-Lysine. As described herein, the gA-3 peptide analog has a minimum inhibitory concentration (MIC) equivalent to ~2-fold higher that of wild-type Gramicidin A against *B. subtilis, S. Aureus*, and *S. Pyogenes*, while the peptide concentration required to cause 50% K$^+$ ion leakage relative to the lysis by a 1% TritonX-100 solution is greater than $10^5$ fold greater than that of the wild-type Gramicidin A peptide of SEQ ID NO: 2. In addition, the water solubility of SEQ ID NO: 5 was shown to be ~740-fold higher than that of wild-type Gramicidin A (FIG. 2). In some embodiments, the Gramicidin A peptide analog having reduced cytotoxicity and increased solubility relative to wild-type Gramicidin A or SEQ ID NO: 2 consists essentially of SEQ ID NO: 5. In some embodiments, the Gramicidin A peptide analog having reduced cytotoxicity and increased solubility relative to wild-type Gramicidin A or SEQ ID NO: 2 consists of SEQ ID NO: 5.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dK-W-dK-dL-W—NHCH$_2$CH$_2$OH (SEQ ID NO: 6 or gA-4). The gA-4 peptide analog has the d-Leucine at positions 10 and 12 of SEQ ID NO: 2 replaced by d-Lysine. As described herein, the gA-4 peptide analog has a minimum inhibitory concentration (MIC) equivalent to or ~2-fold higher that of wild-type Gramicidin A against *B. subtilis, S. Aureus*, and *S. Pyogenes*, while the peptide concentration required to cause 50% K$^+$ ion leakage relative to the lysis by a 1% TritonX-100 solution is over 10$^5$ fold greater than that of the wild-type Gramicidin A peptide of SEQ ID NO: 2. In addition, the water solubility of SEQ ID NO: 6 was shown to be ~740-fold higher than that of wild-type Gramicidin A (FIG. 2). In some embodiments, the Gramicidin A peptide analog having reduced cytotoxicity and increased solubility relative to wild-type Gramicidin A or SEQ ID NO: 2 consists essentially of SEQ ID NO: 6. In some embodiments, the Gramicidin A peptide analog having reduced cytotoxicity and increased solubility relative to wild-type Gramicidin A or SEQ ID NO: 2 consists of SEQ ID NO: 6.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dK-W-dK-W-dK-W—NHCH$_2$CH$_2$OH (SEQ ID NO: 7 or gA-5). The gA-5 peptide analog has the d-Leucine at positions 10, 12, and 14 of SEQ ID NO: 2 replaced by d-Lysine. As described herein, the gA-5 peptide analog has a minimum inhibitory concentration (MIC) equivalent to or ~2-fold higher that of wild-type Gramicidin A against *B. subtilis*, and *S. Pyogenes*, but a much higher MIC for *S. aureus*. However, the peptide concentration of SEQ ID NO: 7 required to cause 50% K$^+$ ion leakage relative to the lysis by a 1% TritonX-100 solution is over 10$^6$ fold greater than that of the wild-type Gramicidin A peptide of SEQ ID NO: 2. In fact, as described herein, no noticeable K$^+$ ion leakage was determined using the gA-5 peptide analog even at a high concentration of 100 μM. In addition, the water solubility of SEQ ID NO: 7 was shown to be ~1500-fold higher than that of wild-type Gramicidin A (FIG. 2). In some embodiments, the Gramicidin A peptide analog having reduced cytotoxicity and increased solubility relative to wild-type Gramicidin A or SEQ ID NO: 2 consists essentially of SEQ ID NO: 7. In some embodiments, the Gramicidin A peptide analog having reduced cytotoxicity and increased solubility relative to wild-type Gramicidin A or SEQ ID NO: 2 consists of SEQ ID NO: 7.

In some embodiments of these aspects and all such aspects described herein, the Gramicidin A peptide analog having reduced cytotoxicity and increased solubility relative to wild-type Gramicidin A or SEQ ID NO: 2 comprises an amino acid sequence of formyl-V-G-A-dL-A-dV-V-dV-W-dR-W-dR-W-dR-W—NHCH$_2$CH$_2$OH (SEQ ID NO: 8 or gA-6). The gA-6 peptide analog has the d-Leucine at positions 10, 12, and 14 of SEQ ID NO: 2 replaced by d-Arginine. As described herein, the gA-6 peptide analog has a minimum inhibitory concentration (MIC) equivalent to or ~2-fold higher that of wild-type Gramicidin A against *B. subtilis*, and *S. Pyogenes*, but a much higher MIC for *S. aureus*. The water solubility of SEQ ID NO: 8 was shown to be ~800-fold higher than that of wild-type Gramicidin A (FIG. 2). In some embodiments, the Gramicidin A peptide analog having increased solubility relative to wild-type Gramicidin A or SEQ ID NO: 2 consists essentially of SEQ ID NO: 8. In some embodiments, the Gramicidin A peptide analog having reduced cytotoxicity and increased solubility relative to wild-type Gramicidin A or SEQ ID NO: 2 consists of SEQ ID NO: 8.

As used herein, the term "antimicrobial" means that a peptide analog or derivative is capable of killing a microorganism and/or reducing or preventing growth of a microorganism. Methods for determining the antimicrobial activity of a peptide are known to those of ordinary skill in the art and some such methods are described herein in the Examples. For example, the peptide analog or derivative is applied to or contacted to a solution in which a microorganism has been previously grown and, after a suitable period of time, the level of growth inhibition and/or cell death of the microorganism is determined. The terms "antimicrobial activity," "microbicidal," and "microbistatic" refer to the ability of a peptide analog or derivative described herein to modify a function or metabolic process of a target microorganism, for example so as to at least partially affect replication, vegetative growth, toxin production, survival, viability in a quiescent state, or other attribute. In some embodiments of the aspects described herein, the terms relate to inhibition of growth of a microorganism. In some embodiments of the aspects described herein, the term antimicrobial activity relates to the ability of a peptide analog or derivative described herein to kill at least one bacterial species. In some embodiments of the aspects described herein, the bacterial species is selected from the group consisting of gram-positive and gram-negative bacteria.

Bacteria to be inhibited using the compositions and method described herein can include gram-negative and gram-positive bacteria, in addition to organisms classified in orders of the class Mollicutes and the like, such as species of the *Mycoplasma* and *Acholeplasma* genera. Examples of gram-positive bacteria include, but are not limited to, *Staphylococcus aureus, Staphylococcus epidermis, Streptococcus agalactiae*, Group A *streptococcus, Streptococcus pyogenes, Enterococcus faecalis*, Group B gram-positive *streptococcus, Corynebacterium xerosis*, and *Listeria monocytogenes*. Specific examples of gram-negative bacteria include, but are not limited to, *Escherichia coli, Acinetobacter baumannii, Pseudomonas aeruginosa, Salmonella, Hemophilus influenza, Neisseria, Vibrio cholerae, Vibrio parahaemolyticus* and *Helicobacter pylori*. Examples of fungi can include yeasts, such as *Candida albicans*. Examples of viruses can include measles virus, herpes simplex virus (HSV-1 and -2), herpes family members (HIV, hepatitis C, vesicular, stomatitis virus (VSV), visna virus, and cytomegalovirus (CMV). Examples of protozoa can include *Giardia*.

In some embodiments of the aspects described herein, a Gramicidin A peptide analog or derivative has a minimal inhibitory concentration that is equivalent to or less that that of the wild-type Gramicidin A, under the same conditions. The terms "minimal inhibitory concentration" or "MIC," as used herein, refer to the lowest concentration of an antimicrobial agent (e.g., a Gramicidin A peptide analog) required to prevent growth or otherwise modify a function of a microorganism under certain conditions, for example in liquid broth medium, and can be determined for a number of different microorganisms according to standard techniques well known in the art. For example, as described herein, MICs can be measured using the broth microdilution method. Briefly, bacteria from a single colony are grown overnight in broth at a specified temperature and agitation conditions. An aliquot of the broth is taken and diluted in fresh broth and cultured for another specified period of time until the cells reach mid-logarithmic phase. The cells are diluted to a desired concentration and the bacterial suspension is added to each well of a sterile multi-well plate, such as a 96-well microtiter plate. Serially diluted Gramicidin A peptide analog or derivatives being tested are added to the multi-well plate, and the plates are incubated overnight overnight before the absorbance is measured, for example, using a microtiter plate reader (SPECTRAMAX M5, Molecular Devices, Sunnyvale, Calif.). The viability of the bacteria was normalized as % survival=$(OD_{pep,bac}-OD_{broth}$ only$)/(OD_{DMSO,bac}-OD_{broth}$ only$)\times 100\%$. The MIC is recorded as the concentration of a Gramicidin A peptide analog or derivative required for complete inhibition of cell growth (no change in absorbance). Representative curves plotting cell viability against peptide concentration are shown, for example, in FIGS. 6A-6B.

It is preferred that the minimal inhibitory concentration of a Gramicidin A peptide analog or derivative for use in the compositions and methods described herein is less than 10-fold higher, less than 9-fold higher, less than 8-fold higher, less than 7-fold higher, 6-fold higher, less than 5-fold higher, less than 4-fold higher, less than 3-fold higher, less than 2-fold higher, less than 1.5-fold higher, less than 1.25-fold higher, or equivalent to the MIC of the wild-type Gramicidin A peptide of SEQ ID NO: 2, under the same assay conditions. It is even more preferred that the minimal inhibitory concentration of a Gramicidin A peptide analog or derivative for use in the compositions and methods described herein is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, at least 98% less, at least 99% less, at least 2-fold lower, at least 3-fold lower, at least 4-fold lower, at least 5-fold lower, at least 6-fold lower, at least 7-fold lower, at least 8-fold lower, at least 9-fold lower, at least 10-fold lower, at least 50-fold lower, at least 100-fold lower, at least 1000-fold lower, or more than the MIC of the wild-type Gramicidin A peptide of SEQ ID NO: 2, under the same assay conditions.

As used herein, the terms "analog" or "variant" shall be taken to mean a peptide that is modified to comprise one or more naturally-occurring and/or non-naturally-occurring amino acids, provided that the peptide analog is capable of reducing or preventing growth of a microorganism or killing a microorganism, as described herein. For example, the term "analog" encompasses an inhibitory peptide comprising one or more conservative amino acid changes. The term "analog" also encompasses a peptide comprising, for example, one or more D-amino acids, as described herein. Such an analog has the additional characteristic of, for example, protease resistance. Gramicidin A peptide analogs can be prepared by, for example, peptide synthesis. Such modifications include, for example, deletions from, and/or insertions into and/or substitutions of, residues within the amino acid sequence of the Gramicidin A peptide of SEQ ID NO: 2. Any combination of deletion, insertion, and substitution is made to arrive at the final peptide variant, provided that the final peptide variant possesses the desired characteristics, e.g., is anti-microbial, has low cellular cytotoxicity, and/or has high solubility.

The term "amino acid," as used herein, is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g. diamino butyric acid and diamino propionic acid and the like. In the context of a peptide, an amino acid is synonymous with amino acid residue, as understood by one of ordinary skill in the art.

Amino acid sequence insertions include intrasequence insertions of single or multiple amino acid residues. Another type of variant is an amino acid substitution analog. These variants have at least one amino acid residue in the wild-type Gramicidin A replaced by a different residue. In some embodiments, the substitution peptide variant is a conservative substitution. In some such embodiments, while the amino acids at positions 10, 12, and/or 14 of SEQ ID NO: 2 are replaced by a non-conservative substitution, for example, the replacement of the non-polar leucine with the cationic lysine, as described herein, one or more other amino acid residues of SEQ ID NO: 2 can be modified or mutated with a conservative substitution.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

The Gramicidin A peptide analogs and derivatives described herein can also comprise unnatural amino acids or modifications of N or C terminal amino acids. Examples of such unnatural or modified amino acids include, but are not limited to, acedisubstituted amino acids, N-alkyl amino acids, lactic acid, 4-hydroxyproline, γ-carboxyglutamate, ε-N,N,N-trimethyllysine, ornithine, ε-N-acetyllysine, O-phosphoserine, N-acetylserine, N-formylmethionine, 3-methylhistidine, 5-hydroxylysine, δ-N-methylarginine.

For example, as described herein, the therapeutic utility of solubilized gramicidin A as systemic antibiotics can be further fine tuned by Nε-trialkylation, such as Nε-trimethylation, of one or more cationic residues, such as lysine. The alkyl group can be a C1-C4 alkyl. Further, each alkuyl group can be different from the other alkyl groups on the same cationic amino acid, such as lysine. In some embodiments of the compositions and methods described herein, the alkyl group is selected from methyl, ethyl, propyl, isopropyl, and butryl.

As described herein, after side chain alkylation, gramicidin A analogs comprising Nε-trialkylated lysine or ornithine amino acids at positions 10, 14, and/or 10 and 14 of SEQ ID NO: 2 showed significantly decreased toxicity against human red blood cells. While their antibacterial activities were mildly affected, 2-5 fold increases were observed in therapeutic indices. Studies in model liposomal systems, as described herein, indicated that cationic amino acid side chain alkylation affects both binding affinity between peptides and vesicles, and channel formation.

Accordingly, in some embodiments of the compositions and methods described herein, one or more of the d-Leucine residues at positions 10 or 14 of wild-type Gramicidin A or SEQ ID NO: 2 is replaced with a Nε-trialkylated cationic residue. In some such embodiments, the Nε-trialkylated cationic residue is Nε-trialkylated lysine. In some embodiments of these aspects and all such aspects described herein, a d-Leucine residue at position 10 of wild-type Gramicidin A or SEQ ID NO: 2 is replaced with a Nε-trialkylated lysine. In some embodiments of these aspects and all such aspects described herein, a d-Leucine residue at position 14 of wild-type Gramicidin A or SEQ ID NO: 2 is replaced with a Nε-trialkylated lysine. In some embodiments of these aspects and all such aspects described herein, d-Leucine residues at positions 10 and 14 of wild-type Gramicidin A or SEQ ID NO: 2 are both replaced with a Nε-trialkylated lysine.

In some embodiments of the compositions and methods described herein, one or more of the d-Leucine residues at positions 10 or 14 of wild-type Gramicidin A or SEQ ID NO: 2 is replaced with a Nε-trimethylated cationic residue. In some such embodiments, the Nε-trimethylated cationic residue is Nε-trimethylated lysine. In some embodiments of these aspects and all such aspects described herein, a d-Leucine residue at position 10 of wild-type Gramicidin A or SEQ ID NO: 2 is replaced with a Nε-trimethylated lysine. In some embodiments of these aspects and all such aspects described herein, a d-Leucine residue at position 14 of wild-type Gramicidin A or SEQ ID NO: 2 is replaced with a Nε-trimethylated lysine. In some embodiments of these aspects and all such aspects described herein, d-Leucine residues at positions 10 and 14 of wild-type Gramicidin A or SEQ ID NO: 2 are both replaced with a Nε-trimethylated lysine.

In other embodiments of the compositions and methods described herein, one or more of the d-Leucine residues at positions 10 or 14 of wild-type Gramicidin A or SEQ ID NO: 2 is replaced with a Nε-trialkylated ornithine residue. In some embodiments of these aspects and all such aspects described herein, a d-Leucine residue at position 10 of wild-type Gramicidin A or SEQ ID NO: 2 is replaced with a Nε-trialkylated ornithine. In some embodiments of these aspects and all such aspects described herein, a d-Leucine residue at position 14 of wild-type Gramicidin A or SEQ ID NO: 2 is replaced with a Nε-trialkylated ornithine. In some embodiments of these aspects and all such aspects described herein, d-Leucine residues at positions 10 and 14 of wild-type Gramicidin A or SEQ ID NO: 2 are both replaced with a Nε-trialkylated ornithine.

In some embodiments of the compositions and methods described herein, one or more of the d-Leucine residues at positions 10 or 14 of wild-type Gramicidin A or SEQ ID NO: 2 is replaced with a Nε-trimethylated ornithine. In some embodiments of these aspects and all such aspects described herein, a d-Leucine residue at position 10 of wild-type Gramicidin A or SEQ ID NO: 2 is replaced with a Nε-trimethylated ornithine. In some embodiments of these aspects and all such aspects described herein, a d-Leucine residue at position 14 of wild-type Gramicidin A or SEQ ID NO: 2 is replaced with a Nε-trimethylated ornithine. In some embodiments of these aspects and all such aspects described herein, d-Leucine residues at positions 10 and 14 of wild-type Gramicidin A or SEQ ID NO: 2 are both replaced with a Nε-trimethylated ornithine.

As used herein the term "derivative" refers to a peptide that is derived from an anti-microbial Gramicidin A peptide analog as described herein, e.g., a fragment or processed form of the peptide analog, and includes peptides which have been chemically modified by techniques such as adding additional side chains, ubiquitination, labeling, pegylation (derivatization with polyethylene glycol), and insertion, deletion or substitution of amino acids, including insertion, deletion and substitution of amino acids and other molecules (such as amino acid mimetics or unnatural amino acids) that do not normally occur in the peptide sequence of the Gramicidin A peptide analog that is basis of the derivative, for example but not limited to insertion of ornithine, which do not normally occur in human proteins. The term "derivative" is also intended to encompass all modified variants of the antimicrobial peptides variants, functional derivatives, analogues and fragments thereof, as well as peptides with substantial identity as compared to the reference peptide to which they refer to. The term "derivative" also encompasses fusion proteins or fusion polypeptides comprising a peptide analog as described herein. For example, the fusion protein can comprise a label, such as, for example, an epitope, e.g., a FLAG epitope or a V5 epitope or an HA epitope. Such a tag can be useful for, for example, purifying the fusion protein. The term "derivative" also encompasses a derivatized peptide, such as, for example, a peptide modified to contain one or more-chemical moieties other than an amino acid. The chemical moiety can be linked covalently to the peptide, e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide analog or derivative.

As used herein, by "reduced toxicity" or "reduced cytoxicity" is meant that a Gramicidin A peptide analog or derivative thereof has reduced toxicity to mammalian cells relative to the wild-type Gramicidin A peptide. As used herein, the term "reduced toxicity" indicates that a peptide or analog or derivative thereof does not induce or decreases the incidence or degree of one or more adverse response(s) in a subject or in a cell, tissue or organ of a subject to which it is administered relative to the wild-type Gramicidin A peptide. For example, ideally a Gramicidin A peptide analog or derivative described herein does not cause dysfunction of an organ or a system of organs or cause cell death. For example, an antimicrobial Gramicidin A peptide analog or derivative thereof is not nephrotoxic and/or is not neurotoxic and/or does not cause rhabdomyolysis and/or does not cause seizures and/or does not cause cardiac arrhythmia and/or does not have a myelosuppressive effect and/or does not cause diarrhea and/or does not cause anaphylaxis and/or does not cause significant levels of hemolysis, which may result in hemolytic anemia. Methods for comparing and determining toxicity of a Gramicidin A peptide analog or derivative thereof are known to the skilled artisan and are described herein, and include, for example, contacting a sample of red blood cells with the peptide analog or derivative thereof and determining the level of hemolysis caused by the peptide analog or derivative thereof relative to the wild-type Gramicidin A peptide. Also, a sample of red blood cells can be contacted with the peptide analog or derivative thereof and the peptide-induced leakage of potassium from the red blood cells can be assessed using atomic emission spectroscopy, as described herein, relative to the wild-type Gramicidin A peptide.

Accordingly, in some embodiments of these aspects, the toxicity of a Gramicidin A peptide analog or derivative thereof is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, at least 98% less, at least 99% less, at least 2-fold lower, at least 3-fold lower, at least 4-fold lower, at least 5-fold lower, at least 6-fold lower, at least 7-fold lower, at least 8-fold lower, at least 9-fold lower, at least 10-fold lower, at least 50-fold lower, at least 100-fold lower, at least 1000-fold lower, or more, than that of wild-type Gramicidin A peptide under the same conditions and at the same concentration.

A Gramicidin A peptide analog or derivative described herein preferably has low or non-detectable cytotoxicity against mammalian cells e.g., red blood cells or T-lymphocytes, such as Jurkat cells. For example, a Gramicidin A peptide analog or derivative described herein induces cytotoxicity in at least 10% or less, at least 9% or less, at least 8% or less, at least 7% or less, at least 6% or less, at least 5% or less, at least 4% or less, at least 3% or less, at least 2% or less, at least 1% or less, at least 0.5% or less cells in a culture of mammalian cells, such as red blood cells or T-lymphocytes, at concentrations equal to or greater the minimum inhibitory concentration used in a prophylactic or therapeutic treatment of infection by the Gramicidin A peptide analog.

The ability of a Gramicidin A peptide analog or derivative to induce lysis of red blood cells or hemolysis is an exemplary way of assessing cellular toxicity of a peptide. Accordingly, in some embodiments of the aspects described herein, a Gramicidin A peptide analog or derivative has a minimal hemolytic concentration that is greater than that that of the wild-type Gramicidin A, under the same conditions. As used herein, the terms "minimal hemolytic concentration" or "MHC" refer to the lowest concentration of a Gramicidin A peptide analog or derivative required to cause hemolysis of blood cells. MHC can be determined with red blood cells (RBC) from various species including human red blood cells (hRBC), as described herein. For example, freshly collected human blood with heparin can be centrifuged to remove the buffy coat, and the erythrocytes obtained washed three times in, for example, 0.85% saline and stored. Serial dilutions of the Gramicidin A peptide analogs in saline can be prepared and placed in wells. Diluted red blood cells can then be diluted and added to each well. Concentration required for complete lysis can be determined visually after 4 h. "$HC_{50}$," as used herein, refers to the peptide concentration that causes 50% lysis or 50% hemoglobin leakage of human red blood cells relative to cell lysis by a 1% Triton-X solution.

Accordingly, in some embodiments, it is preferred that the minimal hemolytic concentration or the $H_{C50}$ of a Gramicidin A peptide analog or derivative for use in the compositions and methods described herein is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 98% higher, at least 99% higher, at least 2-fold higher, at least 3-fold higher, at least 4-fold higher, at least 5-fold higher, at least 6-fold higher, at least 7-fold higher, at least 8-fold higher, at least 9-fold higher, at least 10-fold higher, at least 20-fold higher, at least 30-fold higher, at least 40-fold higher, at least 50-fold higher, at least 60-fold higher, at least 70-fold higher, at least 80-fold higher, at least 90-fold higher, at least 100-fold higher, at least 500-fold higher, at least 1000-fold higher, at least 5000-fold higher, at least 10000-fold higher, at least $10^6$-fold higher, or more, than the MHC or $HC_{50}$ of the wild-type Gramicidin A peptide of SEQ ID NO: 2, under the same assay conditions.

The ability of a Gramicidin A peptide analog or derivative to induce potassium leakage from red blood cells is another exemplary way of assessing cellular toxicity of a peptide. Accordingly, in some embodiments of the aspects described herein, a Gramicidin A peptide analog or derivative has a minimal $KC_{50}$ value that is greater than that that of the wild-type Gramicidin A peptide under the same conditions. As used herein, the terms "minimal $KC_{50}$" or "minimal potassium leakage activity" refer to the lowest concentration of a Gramicidin A peptide analog or derivative required to cause 50% $K^+$ ion leakage from red blood cells relative to $K^+$ ion leakage by a 1% Triton-X solution.

Accordingly, in some embodiments, it is preferred that the $KC_{50}$ of a Gramicidin A peptide analog or derivative for use in the compositions and methods described herein is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 98% higher, at least 99% higher, at least 2-fold higher, at least 3-fold higher, at least 4-fold higher, at least 5-fold higher, at least 6-fold higher, at least 7-fold higher, at least 8-fold higher, at least 9-fold higher, at least 10-fold higher, at least 20-fold higher, at least 30-fold higher, at least 40-fold higher, at least 50-fold higher, at least 60-fold higher, at least 70-fold higher, at least 80-fold higher, at least 90-fold higher, at least 100-fold higher, at least 500-fold higher, at least 1000-fold higher, at least 5000-fold higher, at least 10000-fold higher, at least $10^6$-fold higher, or more, than the $KC_{50}$ of the wild-type Gramicidin A peptide of SEQ ID NO: 2, under the same assay conditions.

Toxicity, hemolytic activity, or potassium leakage activity of a Gramicidin A peptide analog or derivative described herein can be determined using any assay known to one of ordinary skill in the art. For example, human red blood cells can be incubated under various conditions with serial dilutions of a Gramicidin A peptide analog or derivative, and release of hemoglobin monitored, using for example, an absorbance measurement at a specific wavelength. Percentage hemolysis can be calculated using the formula: percentage hemolysis=100·(Peptide absorbance−DMSO alone absorbance)/(Absorbance for complete hemolysis−DMSO alone absorbance), where complete hemolysis is achieved, for example, by mixing RBCs with a 1% TritonX-100 solution. The peptide concentration required to cause 50% hemoglobin leakage can then suitably be determined.

To determine potassium ($K^+$) leakage activity of a Gramicidin A peptide analog or derivative described herein, human red blood cells can be incubated under various conditions with serial dilutions of a Gramicidin A peptide analog or derivative, and potassium release and potassium concentration measured using, for example, a flame-atomic emission spectrometer. The fraction of K+ leakage from RBCs can be then calculated and the peptide concentration required to cause 50% K+ leakage determined.

Toxicity can also be measured against other mammalian cell types, such as cell lines. For example, solutions comprising various concentrations of a Gramicidin A peptide analog or derivative described herein can be incubated with a desired cell population. The MTT assay can be performed on the incubated cells and absorbance at a specific wavelength recorded.

A Gramicidin A peptide analog or derivative described herein preferably has increased water solubility relative to the wild-type Gramicidin A peptide of SEQ ID NO: 2. As used herein, "water solubility" refers to the ability of or degree to which a peptide analog or derivative can dissolve in an aqueous solution, under specific conditions. An "aqueous solution" or "aqueous environment," as used herein, is a water based environment, including salt solutions and plasma and water-based gels and pharmaceutical excipients. Such an environment may or may not include surfactants or amphiphilic compounds for solubilizing hydrophobes. Accordingly, in some embodiments, it is preferred that the water solubility of a Gramicidin A peptide analog or derivative for use in the compositions and methods described herein is at least 10% higher, at least 15% higher, at least 20% higher, at least 25% higher, at least 30% higher, at least 35% higher, at least 40% higher, at least 45% higher, at least 50% higher, at least 55% higher, at least 60% higher, at least 65% higher, at least 70% higher, at least 75% higher, at least 80% higher, at least 85% higher, at least 90% higher, at least 95% higher, at least 98% higher, at least 99% higher, at least 2-fold higher, at least 3-fold higher, at least 4-fold higher, at least 5-fold higher, at least 6-fold higher, at least 7-fold higher, at least 8-fold higher, at least 9-fold higher, at least 10-fold higher, at least 20-fold higher, at least 30-fold higher, at least 40-fold higher, at least 50-fold higher, at least 60-fold higher, at least 70-fold higher, at least 80-fold higher, at least 90-fold higher, at least 100-fold higher, at least 500-fold higher, at least 1000-fold higher, at least 5000-fold higher, at least 10000-fold higher, at least $10^6$-fold higher, or more, than the water solubility of the wild-type Gramicidin A peptide of SEQ ID NO: 2, under the same assay conditions.

Figure 5:
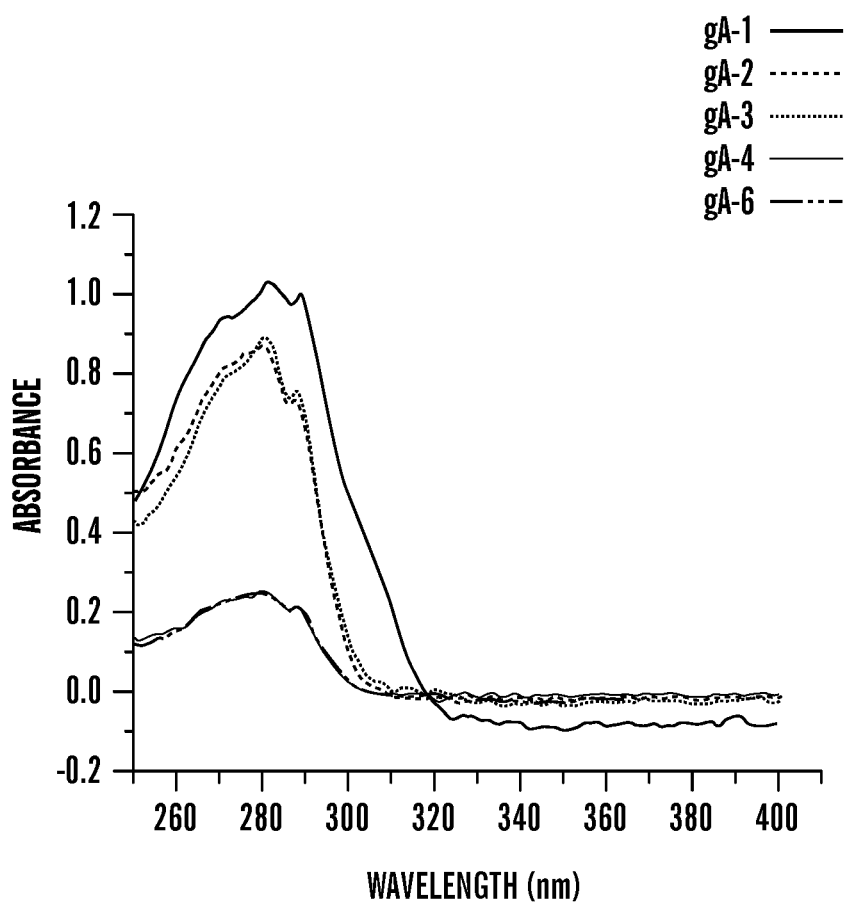
FIG. 5 shows UV/Vis spectra of saturated gA-1, 2, 3, 4, 6 in 10 mM HEPES, pH 7.0 with 1% DMSO.

Assays to measure solubility are well-known to those of ordinary skill in the art, and are described herein. For example, the solubility of a Gramicidin A peptide analog or derivative in a given aqueous buffer can be measured by monitoring tryptophan absorbance, as shown in, for example, FIG. 5.

In some embodiments of the aspects described herein, a Gramicidin A peptide analog or derivative comprises at least one (e.g., at least 1, at least 2, at least 3, at least 4, at least 5, at least 6, at least 7, at least 8, at least 9, at least 10, at least 11, at least 12, at least 13, at least 14, at least 15, or more) amino acid residue(s) selected from the group consisting of homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthy-lalanine, biphenylalanine, cyclohexylalanine, aminoisobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, desamino-Tyr, aminovaleric acid, pyroglutaminic acid, alpha-aminoisobutyric acid, gamma-aminobutyric acid, alpha-aminobutyric acid, alpha, gamma-aminobutyric acidpyridylalanine, α-napthyalanine, β-napthyalanine, Ac-β-napthyalanine, $N^\epsilon$-picoloyl-lysine, 4-halo-Phenyl, 4-pyrolidylalanine, isonipecotic carboxylic acid, and any combinations thereof.

In some embodiments of the aspects described herein, a Gramicidin A peptide analog or derivative comprises at least one (e.g., at least 1, at least 2, at least 3, at least 4, at least 5, at least 6, at least 7, at least 8, at least 9, at least 10, at least 11, at least 12, at least 13, at least 14, at least 15, or more) D-amino acid(s). Without limitations, the D-amino acid can be present at any position in the Gramicidin A peptide analog or derivative. In some embodiments, the D-amino acid is at position 1, and/or at position 2, and/or at position 3, and/or at position 4, and/or at position 5, and/or at position 6, and/or at position 7, and/or at position 8, and/or at position 9, and/or at position 10, and/or at position 11, and/or at position 12, and/or at position 13, and/or at position 14, and/or at position 15, or any combination thereof, of SEQ ID NO: 2. In those embodiments where more than one D-amino acids are present, they can be positioned next to or not next to each other. In those embodiments where three or more D-amino acids are present, some of the D-amino acids can be present next to another D-amino acid, while some of the D-amino acids are not next to another D-amino acid In some embodiments of the aspects described herein, the Gramicidin A peptide analog or derivative comprises a chemically modified amino acid. Such a chemically modified amino acid can be present at any position in the Gramicidin A peptide analog or derivative. In some embodiments, the chemically modified amino acid is at position 1, and/or at position 2, and/or at position 3, and/or at position 4, and/or at position 5, and/or at position 6, and/or at position 7, and/or at position 8, and/or at position 9, and/or at position 10, and/or at position 11, and/or at position 12, and/or at position 13, and/or at position 14, and/or at position 15, or any combination thereof, of SEQ ID NO: 2. Additionally, in those embodiments where more than one chemically modified amino acids are present, they can be positioned next to or not next to each other. In those embodiments where three or more chemically modified amino acids are present, some of the chemically modified amino acids can be present next to each other while some of the chemically modified amino are not next to another chemically modified amino acid. As used herein, the term "chemically modified amino acid" refers to an amino acid that has been treated with one or more reagents.

In some embodiments of the aspects described herein, the Gramicidin A peptide analog or derivative comprises at least one (e.g., at least 1, at least 2, at least 3, at least 4, at least 5, at least 6, at least 7, at least 8, at least 9, at least 10, at least 11, at least 12, at least 13, at least 14, at least 15, or more) beta-amino acid(s). The beta-amino acid can be present at any position in the Gramicidin A peptide analog or derivative. In some embodiments, the beta-amino acid is at position 1, and/or at position 2, and/or at position 3, and/or at position 4, and/or at position 5, and/or at position 6, and/or at position 7, and/or at position 8, and/or at position 9, and/or at position 10, and/or at position 11, and/or at position 12, and/or at position 13, and/or at position 14, and/or at position 15, or any combination thereof, of SEQ ID NO: 2. Further, in those embodiments where more than one beta-amino acids are present, they can be positioned next to or not next to each other. In those embodiments where three or more beta-amino acids are present, some of the beta-amino acids can be present next to another beta-amino acid while some of the beta-amino are not next to another beta-amino acid.

Exemplary beta-amino acids include, but are not limited to, L-β-Homoproline hydrochloride; (±)-3-(Boc-amino)-4-(4-biphenylyl)butyric acid; (±)-3-(Fmoc-amino)-2-phenylpropionic acid; (1S,3R)-(+)-3-(Boc-amino)cyclopentanecarboxylic acid; (2R,3R)-3-(Boc-amino)-2-hydroxy-4-phenylbutyric acid; (2S,3R)-3-(Boc-amino)-2-hydroxy-4-phenylbutyric acid; (R)-2-[(Boc-amino)methyl]-3-phenylpropionic acid; (R)-3-(Boc-amino)-2- methylpropionic acid; (R)-3-(Boc-amino)-2-phenylpropionic acid; (R)-3-(Boc-amino)-4-(2-naphthyl)butyric acid; (R)-3-(Boc-amino)-5-phenylpentanoic acid; (R)-3-(Fmoc-amino)-4-(2-naphthyl)butyric acid; (R)-(−)-Pyrrolidine-3-carboxylic acid; (R)-Boc-3,4-dimethoxy-β-Phe-OH; (R)-Boc-3-(3-pyridyl)-β-Ala-OH; (R)-Boc-3-(trifluoromethyl)-β-Phe-OH; (R)-Boc-3-cyano-β-Phe-OH; (R)-Boc-3-methoxy-β-Phe-OH; (R)-Boc-3-methyl-β-Phe-OH; (R)-Boc-4-(4-pyridyl)-β-Homoala-OH; (R)-Boc-4-(trifluoromethyl)-β-Homophe-OH; (R)-Boc-4-(trifluoromethyl)-β-Phe-OH; (R)-Boc-4-bromo-β-Phe-OH; (R)-Boc-4-chloro-β-Homophe-OH; (R)-Boc-4-chloro-β-Phe-OH; (R)-Boc-4-cyano-β-Homophe-OH; (R)-Boc-4-cyano-β-Phe-OH; (R)-Boc-4-fluoro-β-Phe-OH; (R)-Boc-4-methoxy-β-Phe-OH; (R)-Boc-4-methyl-β-Phe-OH; (R)-Boc-β-Tyr-OH; (R)-Fmoc-4-(3-pyridyl)-β-Homoala-OH; (R)-Fmoc-4-fluoro-β-Homophe-OH; (S)-(+)-Pyrrolidine-3-carboxylic acid; (S)-3-(Boc-amino)-2-methylpropionic acid; (S)-3-(Boc-amino)-4-(2-naphthyl)butyric acid; (S)-3-(Boc-amino)-5-phenylpentanoic acid; (S)-3-(Fmoc-amino)-2-methylpropionic acid; (S)-3-(Fmoc-amino)-4-(2-naphthyl)butyric acid; (S)-3-(Fmoc-amino)-5-hexenoic acid; (S)-3-(Fmoc-amino)-5-phenyl-pentanoic acid; (S)-3-(Fmoc-amino)-6-phenyl-5-hexenoic acid; (S)-Boc-2-(trifluoromethyl)-β-Homophe-OH; (S)-Boc-2-(trifluoromethyl)-β-Homophe-OH; (S)-Boc-2-(trifluoromethyl)-β-Phe-OH; (S)-Boc-2-cyano-β-Homophe-OH; (S)-Boc-2-methyl-β-Phe-OH; (S)-Boc-3,4-dimethoxy-β-Phe-OH; (S)-Boc-3-(trifluoromethyl)-β-Homophe-OH; (S)-Boc-3-(trifluoromethyl)-β-Phe-OH; (S)-Boc-3-methoxy-β-Phe-OH; (S)-Boc-3-methyl-β-Phe-OH; (S)-Boc-4-(4-pyridyl)-β-Homoala-OH; (S)-Boc-4-(trifluoromethyl)-β-Phe-OH; (S)-Boc-4-bromo-β-Phe-OH; (S)-Boc-4-chloro-β-Homophe-OH; (S)-Boc-4-chloro-β-Phe-OH; (S)-Boc-4-cyano-β-Homophe-OH; (S)-Boc-4-cyano-β-Phe-OH; (S)-Boc-4-fluoro-β-Phe-OH; (S)-Boc-4-iodo-β-Homophe-OH; (S)-Boc-4-methyl-β-Homophe-OH; (S)-Boc-4-methyl-β-Phe-OH; (S)-Boc-β-Tyr-OH; (S)-Boc-γ,γ-diphenyl-β-Homoala-OH; (S)-Fmoc-2-methyl-β-Homophe-OH; (S)-Fmoc-3,4-difluoro-β-Homophe-OH; (S)-Fmoc-3-(trifluoromethyl)-β-Homophe-OH; (S)-Fmoc-3-cyano-β-Homophe-OH; (S)-Fmoc-3-methyl-3-Homophe-OH; (S)-Fmoc-γ,γ-diphenyl-β-Homoala-OH; 2-(Boc-aminomethyl)phenylacetic acid; 3-Amino-3-(3-bromophenyl)propionic acid; 3-Amino-4,4,4-trifluorobutyric acid; 3-Aminobutanoic acid; DL-3-Aminoisobutyric acid; DL-β-Aminoisobutyric acid puriss; DL-β-Homoleucine; DL-β-Homomethionine; DL-β-Homophenylalanine; DL-β-Leucine; DL-β-Phenylalanine; L-β-Homoalanine hydrochloride; L-β-Homoglutamic acid hydrochloride; L-β-Homoglutamine hydrochloride; L-β-Homohydroxyproline hydrochloride; L-β-Homoisoleucine hydrochloride; L-β-Homoleucine hydrochloride; L-β-Homolysine dihydrochloride; L-β-Homomethionine hydrochloride; L-β-Homophenylalanine allyl ester hydrochloride; L-β-Homophenylalanine hydrochloride; L-(3-Homoserine; L-β-Homothreonine; L-β-Homotryptophan hydrochloride; L-β-Homotyrosine hydrochloride; L-β-Leucine hydrochloride; Boc-D-β-Leu-OH; Boc-D-β-Phe-OH; Boc-β³-Homopro-OH; Boc-β-Glu(OBzl)-OH; Boc-β-Homoarg(Tos)-OH; Boc-β-Homoglu(OBzl)-OH; Boc-β-Homohyp(Bzl)-OH (dicyclohexylammonium) salt technical; Boc-β-Homolys(Z)—OH; Boc-β-Homoser(Bzl)-OH; Boc-β-Homothr(Bzl)-OH; Boc-β-Homotyr(Bzl)-OH; Boc-β-Ala-OH; Boc-β-Gln-OH; Boc-β-Homoala-OAll; Boc-β-Homoala-OH; Boc-β-Homogln-OH; Boc-β-Homoile-OH; Boc-β-Homoleu-OH; Boc-β-Homomet-OH; Boc-β-Homophe-OH; Boc-β-Homotrp-OH; Boc-β-Homotrp-OMe; Boc-β-Leu-OH; Boc-β-Lys(Z)—OH (dicyclohexylammonium) salt; Boc-β-Phe-OH; Ethyl 3-(benzylamino)propionate; Fmoc-D-β-Homophe-OH; Fmoc-L-β³-homoproline; Fmoc-β-D-Phe-OH; Fmoc-β-Gln(Trt)-OH; Fmoc-β-Glu(OtBu)-OH; Fmoc-β-Homoarg(Pmc)-OH; Fmoc-β-Homogln(Trt)-OH; Fmoc-β-Homoglu(OtBu)-OH; Fmoc-β-Homohyp(tBu)-OH; Fmoc-β-Homolys(Boc)-OH; Fmoc-β-Homoser(tBu)-OH; Fmoc-β-Homothr(tBu)-OH; Fmoc-β-Homotyr(tBu)-OH; Fmoc-β-Ala-OH; Fmoc-β-Gln-OH; Fmoc-β-Homoala-OH; Fmoc-β-Homogln-OH; Fmoc-β-Homoile-OH; Fmoc-β-Homoleu-OH; Fmoc-β-Homomet-OH; Fmoc-β-Homophe-OH; Fmoc-β-Homotrp-OH; Fmoc-β-Leu-OH; Fmoc-β-Phe-OH; N-Acetyl-DL-β-phenylalanine; Z-D-β-Dab(Boc)-OH; Z-D-β-Dab(Fmoc)-OH purum; Z-DL-β-Homoalanine; Z-β-D-Homoala-OH; Z-β-Glu(OtBu)-OH technical; Z-β-Homotrp(Boc)-OH; Z-β-Ala-OH purum; Z-β-Dab(Boc)-OH; Z-β-Dab(Fmoc)-OH; Z-β-Homoala-OH; β-Alanine; β-Alanine BioXtra; β-Alanine ethyl ester hydrochloride; β-Alanine methyl ester hydrochloride; β-Glutamic acid hydrochloride; cis-2-Amino-3-cyclopentene-1-carboxylic acid hydrochloride; cis-3-(Boc-amino)cyclohexanecarboxylic acid; and cis-3-(Fmoc-amino)cyclohexanecarboxylic acid.

In some embodiments of the aspects described herein, the Gramicidin A peptide analog or derivative comprises at least one (e.g., at least 1, at least 2, at least 3, at least 4, at least 5, at least 6, at least 7, at least 8, at least 9, at least 10, at least 11, at least 12, at least 13, at least 14, at least 15, or more) modified peptide linkages(s), e.g., a peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. The peptide replacement linkage can be present at any position in the Gramicidin A peptide analog or derivative fragment. In some embodiments, the peptide replacement linkage is at position 1, and/or at position 2, and/or at position 3, and/or at position 4, and/or at position 5, and/or at position 6, and/or at position 7, and/or at position 8, and/or at position 9, and/or at position 10, and/or at position 11, and/or at position 12, and/or at position 13, and/or at position 14, and/or at position 15, or any combination thereof, of SEQ ID NO: 2. In those embodiments where more than peptide replacement linkages are present, they can be positioned next to (e.g., on both sides of a given amino acid) or not next to each other (e.g., only one side of a given amino acid is linked via a peptide replacement linkage to the next amino acid).

In some embodiments of the aspects described herein, the N-terminus amino group of the Gramicidin A peptide analog or derivative is conjugated with a nitrogen- or amino-protecting group. As used herein, a "nitrogen protecting group" or an "amino protecting group" refers to moieties that block or mask the NH$_2$ group. Exemplary amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Further amino protecting groups, as well as other representative protecting groups, are disclosed in Greene and Wuts, *Protective Groups in Organic Synthesis*, Chapter 2, 2d ed., John Wiley &

Sons, New York, 1991, and *Oligonucleotides And Analogues A Practical Approach*, Ekstein, F. Ed., IRL Press, N.Y, 1991, content of which is herein incorporated by reference in its entirety.

In some embodiments of the aspects described herein, the N-terminus amino acid of the Gramicidin A peptide analog or derivative is acetylated or alkylated, e.g., with acetyl, ethanoyl, propionyl, t-butanoyl, methyl, ethyl, propyl, butyl, pentyl, or hexanyl.

In some embodiments, the Gramicidin A peptide analog or derivative is conjugated with polyethylene glycol (PEG). Without wishing to be bound by theory, such conjugation can increase the in vivo half life of the Gramicidin A peptide analog or derivative. As used herein, "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof. Methods of conjugating PEGs to peptides are well known in the art. A Gramicidin A peptide analog or derivative can comprise a PEG at the N-terminus, C-terminus, or at an internal amino acid. The PEG can be linked to the N-terminus amino group, C-terminus carboxyl group, or to an amino, hydroxyl or thiol group on the side chain of an amino acid.

In various embodiments of the aspects described herein, any of the peptide analogs or derivatives described herein, can bear or comprise one or more protecting groups. In some embodiments, certain termini and/or side chains bear one or more blocking groups. Thus, for example, the carboxyl terminus can be amidated. In some such embodiments, the C-terminus, and/or N-terminus, and/or internal residues can be blocked with one or more blocking groups.

A wide number of protecting groups are suitable for use with the peptide analogs and derivatives described herein. Such groups include, but are not limited to acetyl, amide, and alkyl groups with acetyl and alkyl groups being particularly preferred for N-terminal protection, and amide groups being preferred for carboxyl terminal protection. In certain embodiments, the protecting groups can include, but are not limited to, alkyl chains as in fatty acids, propeonyl, formyl, and others. Certain carboxyl protecting groups include, but are not limited to, amides, esters, and ether-forming protecting groups. In some embodiments, an acetyl group can be used to protect the amino terminus of a peptide analog or derivative described herein and an amide group can be used to protect the carboxyl terminus. These blocking groups can, for example, enhance the β-helix-forming tendencies of the peptides. Certain particularly preferred blocking groups include alkyl groups of various lengths, e.g., groups having the formula: $CH_3—(CH_2)_n—CO—$, where n can range from about 1 to about 20, from about 1 to about 16, from about 1-18, from about 3 to about 13, and from about 3 to about 10.

Other suitable protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA), and the like.

Protecting/blocking groups are well known to those of skill as are methods of coupling such groups to the appropriate residue(s) comprising the peptides described herein (see, e.g., Greene et al., (1991) Protective Groups in Organic Synthesis, 2nd ed., John Wiley & Sons, Inc. Somerset, N.J.). In some embodiments, for example, acetylation is accomplished during the synthesis when the peptide is on the resin using acetic anhydride. Amide protection can be achieved by the selection of a proper resin for the synthesis. For example, synthesis of the peptides described herein can be performed using rink amide resin as the solid support. After the completion of the synthesis, the semipermanent protecting groups on acidic bifunctional amino acids, such as Asp and Glu and basic amino acid Lys, hydroxyl of Tyr can be simultaneously removed. The peptides released from such a resin using acidic treatment come out with the n-terminal protected as acetyl and the carboxyl protected as $NH_2$ and with the simultaneous removal of all of the other protecting groups.

In other embodiments, pegylated forms of the various peptide analogs and derivatives described herein are contemplated. Pegylation can be used in improve biocompatibility of the peptides and/or to improve serum half-life. Methods of pegylating peptides are well known to those of skill in the art (see, e.g., U.S. Pat. Nos. 7,256,258, 6,552,170, and 6,420,339, and the references cited therein).

In some embodiments of the aspects described herein, an anti-microbial Gramicidin A analog or derivative has one or more modifications to enhance stability. For example, a cleavage site of a protease active in a subject to which a peptide is to be administered is mutated and/or deleted to produce a stable derivative of an anti-microbial Gramicidin A analog or derivative described herein.

Also provided herein are fusion proteins or peptide comprising one or more Gramicidin A peptide analogs or derivatives described herein. Such a fusion protein can comprise a plurality of the same Gramicidin A peptide analogs or derivatives, or a plurality of different Gramicidin A peptide analogs or derivatives, or both a plurality of the same Gramicidin A peptide analogs or derivatives and different Gramicidin A peptide analogs or derivatives. In the case of an antimicrobial peptide that acts by forming a dimmer or multimer, e.g., to form a channel in a membrane of a microorganism, such a fusion protein can assist with formation of the channel. For example, a fusion protein can comprise one or more Gramicidin A peptide analogs or derivatives as described herein as SEQ ID NOs: 3-8 and one or more antimicrobial peptides, analogs or derivatives comprising a sequence other than that set forth in any one of SEQ ID NOs: 3-8. In other embodiments, a fusion protein can comprise one or more Gramicidin A peptide analogs or derivatives as described herein conjugated to a pheromone, e.g., a pheromone produced by a microorganism, such as for targeting the antimicrobial moiety selectively or specifically to a bacterial cell.

Gramicidin A Peptide Analog Synthesis and Preparation.

The Gramicidin A peptide analogs described herein can be chemically synthesized using standard chemical peptide synthesis techniques, such as, for example, those described herein in the Examples. In those aspects and embodiments, where the peptides comprise "D" amino acids, the peptides can be recombinantly expressed if a host organism (e.g. bacteria, plant, fungal cells, etc.) are cultured in an environment where one or more of the amino acids is provided to the organism exclusively in a D form. Recombinantly expressed peptides in such a system then incorporate those D amino acids. In some such embodiments, D amino acids can be incorporated in a recombinantly expressed peptide analog using modified amino acyl-tRNA synthetases that recognize D-amino acids.

In certain embodiments of the aspects described herein, the Gramicidin A peptide analogs are chemically synthesized by any of a number of fluid or solid phase peptide synthesis techniques known to those of ordinary skill in the art. Solid phase synthesis, refers to a synthesis method in which the C-terminal amino acid of the sequence is attached to an insoluble support followed by sequential addition of the remaining amino acids in the sequence. Techniques for solid phase synthesis are well known to those of skill in the art and are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc., 85: 2149-2156, and Stewart et al. (1984) Solid Phase Peptide Synthesis, 2nd ed. Pierce Chem. Co., Rockford, Ill., as well as in the Examples section herein.

For example, in one exemplary embodiment, a Gramicidin A peptide analog can be synthesized on Fmoc-Trp-Wang resin using standard Fmoc/tBu chemistry. Five equivalents of each amino acid can be used for the coupling reaction. The peptide analogs can be cleaved off the resin by treating the resin with eolamine. Then resin can then be filtered, for example, through a medium fritted plastic funnel, and rinsed, for example, three times with DCM and meol, to release the peptide analog completely into solvent. The filtrate containing the peptide analog can be dried, for example, by rotary evaporation to a minimal volume. The peptide analog is then precipitated and the precipitation separated out, typically by centrifugation, and dried on, for example, a lyophilizer to receive the side-chain protected peptide. The Boc protecting group on d-lysine of a peptide analog and/or the Pbf protecting group on arginine can be removed by treating the pellet with an appropriate reagent or mixture, as described elsewhere herein. It is noted that in the chemical synthesis of peptides, particularly peptides comprising D amino acids, the chemical synthesis steps usually produce a number of truncated peptides in addition to the desired full-length product. Thus, the peptides are typically purified using, e.g., HPLC, as described herein.

D-amino acids, β amino acids, non-natural amino acids, and the like can be incorporated at one or more positions in a peptide analog simply by using the appropriately derivatized amino acid residue in the chemical synthesis. Modified residues for solid phase peptide synthesis are commercially available from a number of suppliers (see, e.g., Advanced Chem Tech, Louisville; Nova Biochem, San Diego; Sigma, St Louis; Bachem California Inc., Torrance, etc.). The D-form and/or otherwise modified amino acids can be completely omitted or incorporated at any position in the peptide as desired. Thus, for example, in certain embodiments, the peptide can comprise a single modified acid, while in other embodiments, the peptide comprises at least two, generally at least three, more generally at least four, most generally at least five, preferably at least six, more preferably at least seven or even all modified amino acids. In certain embodiments, a peptide analog comprises at least 1, at least 2, at least 3, at least 4, at least 5, at least 6, at least 7, at least 8, at least 9, at least 10, at least 12, or more D-form amino acids.

In some embodiments, the anti-microbial peptide analogs or derivatives described herein can be synthesized using recombinant expression systems. This typically involves creating a DNA sequence that encodes the desired peptide or fusion protein, placing the DNA in an expression cassette under the control of a particular promoter, expressing the peptide or fusion protein in a host, isolating the expressed peptide or fusion protein and, if required, renaturing the peptide or fusion protein.

DNA encoding the anti-microbial peptide analogs or derivatives or fusion protein(s) thereof described herein can be prepared by any suitable method as described above, including, for example, cloning and restriction of appropriate sequences or direct chemical synthesis.

The nucleic acid can be ligated into an appropriate vector comprising appropriate expression control sequences (e.g., promoter, enhancer, etc.), and, optionally, containing one or more selectable markers (e.g., antibiotic resistance genes).

The nucleic acid sequences encoding the peptide analogs or derivatives or fusion proteins thereof described herein can be expressed in a variety of host cells, including, but not limited to, E. coli, other bacterial hosts, yeast, fungus, and various higher eukaryotic cells such as insect cells (e.g. SF3), the COS, CHO and HeLa cells lines and myeloma cell lines. A recombinant protein gene is typically operably linked to appropriate expression control sequences for each host. For E. coli this can include a promoter such as the T7, trp, or lambda promoters, a ribosome binding site and preferably a transcription termination signal. For eukaryotic cells, control sequences can include a promoter and often an enhancer (e.g., an enhancer derived from immunoglobulin genes, SV40, cytomegalovirus, etc.), and a polyadenylation sequence, and can include splice donor and acceptor sequences.

The plasmids can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant peptide(s) or fusion protein(s) can be purified according to standard procedures of the art, including ammonium sulfate precipitation, affinity columns, column chromatography, gel electrophoresis and the like (see, generally, R. Scopes, (1982) Protein Purification, Springer-Verlag, N.Y.; Deutscher (1990) Methods in Enzymology Vol. 182: Guide to Protein Purification., Academic Press, Inc. N.Y.). Substantially pure compositions of at least about 90 to 95% homogeneity are preferred, and 98 to 99% or more homogeneity are most preferred.

After chemical synthesis, biological expression, or purification, the peptide analogs or fusion proteins thereof described herein can possess a conformation substantially different than the desired native conformation. In such cases, it may be necessary to denature and reduce the peptide analog or fusion protein thereof and then to cause the molecule to re-fold into the preferred conformation. Methods of reducing and denaturing proteins and inducing re-folding are well known to those of skill in the art (see, e.g., Debinski et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski et al., for example, describes the denaturation and reduction of inclusion body proteins in guanidine-DTE. The protein is then refolded in a redox buffer containing oxidized glutathione and L-arginine.

In some embodiments, modifications can be made to the peptide analogs and/or fusion proteins thereof described herein to facilitate their recombinant expression, without diminishing their anti-microbial activity and other properties. Some modifications can be made to facilitate the cloning, expression, or incorporation of the peptide analog into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Antibiotic activity of the Gramicidin A peptide analogs and variants thereof described herein can be tested against resistant bacteria strains in vitro or using animal models. One of the most common methods of measuring anti-microbial effect of a given agant is the Kirby-Bauer method. The Kirby-Bauer method measures the zone of inhibition (ZOI) created when an agent, such as any of the Gramicidin A peptide analogs described herein, is placed on a bacterial lawn grown onto agar. A relatively small or no ZOI (e.g., less than 1 mm) indicates either a non useful anti-microbial effect or low solubility of the active agent in the media of study, while a larger ZOI (e.g., greater than 5 mm) indicates a highly useful anti-microbial effect and effective solubility of the Gramicidin A peptide analog. Also, liquid-broth method assays can be used to measure the antibiotic properties of the Gramicidin A peptide analogs. Minimum Inhibitory Concentration (MIC) can be determined using a standard microtitre dilution method in, for example, LB media with no salt. Briefly, cells are grown overnight at 37 C in LB and diluted in the same medium. Serial dilutions of Gramicidin A peptide analogs can be added followed by the appropriate amount of the desired bacteria strain, for example. Plates are incubated and MICs determined as the lowest antibiotic concentration that inhibited growth.

In vivo assays can also be used for testing the efficacy of the Gramicidin A peptide analogs described herein. For example, healthy mice can be administered a bacterial strain, such as MRSA, into the abdominal cavity, followed by tail vein administration of a Gramicidin A peptide analog being tested, once or multiple times, depending on the experimental design. Following the inoculation with the bacterial strain, survival rate and morbidity rate (associated with, for example, body weight loss etc.) can be determined various days after inoculation, comparing animals injected with the test Gramicidin A peptide analog(s) against control animals that were only inoculated and administered a control formulation. Also provided herein are in vivo assays for testing efficacy of oral administration of the Gramicidin A peptide analogs described herein. For example, mice can be colonized with a clinical isolate of a desired microbial species or strain isolated from a patient. Test mice can be provided drinking water comprising one or more test Gramicidin A peptide analogs, while control mice will receive drinking water comprising a control agent or no agent. Following the colonization with the bacterial strain, survival rate and morbidity rate (associated with, for example, body weight loss etc.) and other parameters (e.g., presence of bacteria in the feces) can be determined various days after inoculation, comparing animals receiving drinking water comprising one or more test Gramicidin A peptide analogs, with the control mice. In vivo assays can also be used for comparing oral availability of the Gramicidin A peptide analogs described herein by comparing, for example, a 1000 mg/kg oral dose with a 5 mg/kg intravenous dose in the rat. Parameters that can be measured and compared in such assays include, for example, bioavailability (or fraction (F) of the orally administered dose that reaches the systemic circulation), mean absorption time, maximum observed serum concentrations, terminal elimination half-lives, volume of the distribution at steady state, etc.

Gramicidin A Peptide Analog and Derivative Pharmaceutical Compositions and Therapeutic Methods Thereof Described herein are pharmaceutical compositions comprising novel Gramicidin A peptide analogs and derivatives and methods thereof for treating a subject having or at risk for developing a microbial infection. These Gramicidin A peptide analogs and derivatives have potent antimicrobial activity combined with increased solubility and decreased toxicity, as demonstrated herein, thereby making them effective agents for use in, for example, systemic administration. The Gramicidin A peptide analogs and derivatives, such as, for example, SEQ ID NO: 3-8, can be administered to a subject in need thereof by any appropriate route which results in an effective treatment in the subject.

Accordingly, in some aspects, provided herein are methods of inhibiting or treating an infection in a subject. Such methods comprise administering to a subject having or at risk for an infection a therapeutically effective amount of a Gramicidin A peptide analog or Gramicidin A peptide analog derivative having reduced cytotoxicity and increased solubility relative to wild-type Gramicidin A or SEQ ID NO: 2, as described herein.

In some embodiments of these methods, the Gramicidin A peptide analog has one or more of the d-Leucine residues at positions 10, 12, or 14 of wild-type Gramicidin A or SEQ ID NO: 2 replaced with a cationic residue. In some such embodiments, the cationic residue is d-Lysine. In some embodiments of these methods, the Gramicidin A peptide analog has one d-Leucine residue at any of positions 10, 12, or 14 of wild-type Gramicidin A or SEQ ID NO: 2 replaced with a cationic residue. In some such embodiments, the cationic residue is d-Lysine. In some embodiments of these methods, the Gramicidin A peptide analog has two d-Leucine residues at any of positions 10, 12, or 14 of wild-type Gramicidin A or SEQ ID NO: 2 replaced with a cationic residue. In some such embodiments, at least one cationic residue is d-Lysine. In some embodiments of these methods, the Gramicidin A peptide analog has each of the three d-Leucine residues at positions 10, 12, or 14 of wild-type Gramicidin A or SEQ ID NO: 2 is replaced with a cationic residue. In some such embodiments, at least one cationic residue is d-Lysine. In some other such embodiments, at least one cationic residue is arginine.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 3 or gA-1. In some embodiments, the Gramicidin A peptide analog having reduced cytotoxicity and increased solubility relative to wild-type Gramicidin A or SEQ ID NO: 2 consists essentially of SEQ ID NO: 3. In some embodiments, the Gramicidin A peptide analog having reduced cytotoxicity and increased solubility relative to wild-type Gramicidin A or SEQ ID NO: 2 consists of SEQ ID NO: 3.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 4 or gA-2. In some embodiments, the Gramicidin A peptide analog having reduced cytotoxicity and increased solubility relative to wild-type Gramicidin A or SEQ ID NO: 2 consists essentially of SEQ ID NO: 4. In some embodiments, the Gramicidin A peptide analog having reduced cytotoxicity and increased solubility relative to wild-type Gramicidin A or SEQ ID NO: 2 consists of SEQ ID NO: 4.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 5 or gA-3. In some embodiments, the Gramicidin A peptide analog having reduced cytotoxicity and increased solubility relative to wild-type Gramicidin A or SEQ ID NO: 2 consists essentially of SEQ ID NO: 5. In some embodiments, the Gramicidin A peptide analog having reduced cytotoxicity and increased solubility relative to wild-type Gramicidin A or SEQ ID NO: 2 consists of SEQ ID NO: 5.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 6 or gA-4. In some embodiments, the Gramicidin A peptide analog having reduced cytotoxicity and increased solubility relative to wild-type Gramicidin A or SEQ ID NO: 2 consists essentially of SEQ ID NO: 6. In some embodiments, the Gramicidin A peptide analog having reduced cytotoxicity and increased solubility relative to wild-type Gramicidin A or SEQ ID NO: 2 consists of SEQ ID NO: 6.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 7 or gA-5. In some embodiments, the Gramicidin A peptide analog having reduced cytotoxicity and increased solubility relative to wild-type Gramicidin A or SEQ ID NO: 2 consists essentially of SEQ ID NO: 7. In some embodiments, the Gramicidin A peptide analog having reduced cytotoxicity and increased solubility relative to wild-type Gramicidin A or SEQ ID NO: 2 consists of SEQ ID NO: 7.

In some embodiments of these methods, the Gramicidin A peptide analog having reduced cytotoxicity and increased solubility relative to wild-type Gramicidin A or SEQ ID NO: 2 comprises an amino acid sequence of SEQ ID NO: 8 or gA-6. In some embodiments, the Gramicidin A peptide analog having reduced cytotoxicity and increased solubility relative to wild-type Gramicidin A or SEQ ID NO: 2 consists essentially of SEQ ID NO: 8. In some embodiments, the Gramicidin A peptide analog having reduced cytotoxicity and increased solubility relative to wild-type Gramicidin A or SEQ ID NO: 2 consists of SEQ ID NO: 8.

The terms "subject" and "individual" are used interchangeably herein, and refer to an animal, for example a human, that a microorganism that inhibited by a Gramicidin A peptide analog or derivative is capable of infecting, and/or a recipient of the Gramicidin A peptide analogs and derivatives described herein, e.g., SEQ ID NO: 3-SEQ ID NO: 8. For treatment of those microbial infections that are specific for a specific animal, such as a human subject, the term "subject" refers to that specific animal. The terms 'non-human animals' and 'non-human mammals' are used interchangeably herein, and include, for example, mammals such as rats, mice, rabbits, sheep, cats, dogs, cows, pigs, and non-human primates.

In some aspects, provided herein are methods of treatment of a subject having a microbial infection, or at risk for a microbial infection, the methods comprising administering to a subject having an a microbial infection, or at risk for a microbial infection, a therapeutically effective amount of a Gramicidin A peptide analog or derivative described herein. In some embodiments of these aspects and all such aspects described herein, the Gramicidin A peptide analog comprises a sequence of SEQ ID NO: 3-SEQ ID NO: 8. In some embodiments, the Gramicidin A peptide analog comprises a sequence of SEQ ID NO: 7.

As used herein, the term "treating or inhibiting a microbial infection" means to inhibit the replication of the particular microorganism causing the infection, to inhibit transmission of the microorganism, or to prevent the microorganism from establishing itself in its host, and to ameliorate or alleviate the symptoms of the disease caused by the infection. The treatment is considered therapeutic if there is a reduction in microorganism load, microorganism replication, microorganism counts or cell numbers, decrease in mortality, decrease in symptoms of the infection, such as a fever, and/or morbidity of a subject. In some such embodiments of the aspects described herein, the microorganism is a gram-positive bacteria.

In some embodiments of the aspects described herein, a subject refers to a human subject having a microbial infection, or at risk for a microbial infection. A subject that has a microbial infection is a subject having objectively measurable cells of the microorganism (e.g., bacterial cells, fungal cells) or cells infected with the microorganism (e.g., virus) present in the subject's body. Subjects that have increased risk for a microbial infection, or are at risk for a microbial infection include, but are not limited to, subjects with possible exposure to the microorganism, such as, for example, members of the armed or diplomatic services, a subject who has traveled recently to a region in which the microorganism is endemic, a hospitalized subject, a subject having had a surgery, etc. In some such embodiments of the aspects described herein, the microorganism is a bacteria. In some such embodiments of the aspects described herein, the microorganism is a gram-positive bacteria.

In some embodiments of the aspects described herein, the methods of treating an subject having a microbial infection further comprise the step of selecting, diagnosing, or identifying a subject having a microbial infection or who is at increased risk for a microbial infection. In such embodiments, a subject is identified as having a microbial infection by objective determination of the presence of cells of the microorganism or virally infected cells in the subject's body by one of skill in the art. Such objective determinations can be performed through the sole or combined use of assays suitable for detection of cells of the microorganism. Preferably, such assays should be microorganism specific, and can allow for detection of exposure to the microorganism before the active stages of the disease. Such assays for use in identifying a subject as having or having had a microorganism infection include, but are not limited to, blood or other biological sample bacterial or fungal cultures, PCR-based assays that detect specific polynucleotides that are present during the infection and replication; ELISA-based assays that detect microbial antigens present or neutralizing antibodies present in a subject sample; plaque-reduction assays, for viral infections, which can be used to determine the serum dilution at which 50% of the infectious virus is neutralized ($NT_{50}$), in addition to the monitoring of specific symptoms associated with the infection.

Bacterial Infections

The term "bacteria" as used herein is intended to encompass all variants of bacteria, for example, prokaryotic organisms and cyanobacteria. In some embodiments of the therapeutic compositions and methods described herein, a subject having or at risk for a microbial infection has a bacterial infection or is infected with one or more bacteria. In some embodiments, the bacteria are gram-positive, gram-negative bacteria, or a combination thereof. In some embodiments, the bacteria are multi-drug resistant bacterium. Examples of gram-positive bacteria include, but are not limited to, *Bacillus cereus, Bacillus anbhracis, Bacillus cereus, Bacillus anthracis, Clostridium botulinum, Clostridium difficle, Clostridium tetani, Clostridium perfringens, Corynebacteria diptheriae, Enterococcus (Streptococcus* D), *Listeria monocytogenes,* Pneumococcal species, Streptococcal species, such as *Streptococcus pneumoniae,* and Staphylococcal species. Examples of gram-negative bacteria include, but are not limited to *P. aeruginosa, A. bumannii, Salmonella* spp, *Klebsiella pneumonia, Shigeila* spp., *Stenotrophomonas maltophilia, Bacteroides, Bordetella pertussis, Brucella, Campylobacter* infections, enterohaemorrhagic *Escherichia coli* (EHEC/*E. coli* 0157:17), enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp., *Pseudomonas aeruginosa, Shigella* spp., *Vibrio cholera* and *Yersinia.* Examples of acid fast bacteria include, but are not limited to, *Mycobacterium tuberculosis, Mycobacterium avium*-intracellulars, *Myobacterium johnei, Mycobacterium leprae,* atypical bacteria, *Chlamydia, Myoplasma, Rickettsia, Spirochetes, Treponema pallidum, Borrelia recurrentis, Borrelia burgdoifii* and *Leptospira icterohemorrhagiae, Actinomyces, Nocardia, P. aeruginosa, A. bumannii, Salmonella* spp., *Klebsiella pneumonia, Shigeila* spp. and/or *Stenotrophomonas maltophilia* and other miscellaneous bacteria.

Accordingly, bacterial infections to be treated using the compositions and methods described herein include, but are not limited to, infections caused by gram-positive bacteria such as, but not limited to, *Bacillus cereus, Bacillus anbhracis, Bacillus cereus, Bacillus anthracis, Clostridium botulinum, Clostridium difficle, Clostridium tetani, Clostridium perfringens, Corynebacteria diptheriae, Enterococcus (Streptococcus* D), *Listeria monocytogenes,* Pneumococcal infections (*Streptococcus pneumoniae*), Staphylococcal infections and Streptococcal infections; infections caused by Gram-negative bacteria such as, but not limited to, *Bacteroides, Bordetella pertussis, Brucella, Campylobacter* infections, enterohaemorrhagic *Escherichia coli* (EHEC/*E. coli* 0157:17) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonnorrhoeae, Neisseria meningitidis, Proteus* spp, *Pseudomonas aeruginosa, Salmonella* spp., *Shigella* spp., *Vibrio cholera* and *Yersinia;* infections caused by acid fast bacteria including, but not limited to, *Mycobacterium tuberculosis, Mycobacterium avium*-intracellulars, *Myobacterium johnei, Mycobacterium leprae,* atypical bacteria, *Chlamydia, Myoplasma, Rickettsia, Spirochetes, Treponema pallidum, Borrelia recurrentis, Borrelia burgdorfii* and *Leptospira icterohemorrhagiae* and other miscellaneous bacteria, including *Actinomyces* and *Nocardia.*

Examples of bacterial infections and situations in which such bacterial infections can occur that are not necessarily specific to a particular bacterial species, but encompassed by the term "bacterial infection," as used herein, include bacterial wound infections, such as in burn wound patients; mucosal infections, enteric infections, Bacteraemia and septic conditions, pneumonia, trachoma, onithosis, trichomoniasis and salmonellosis, especially in veterinary practice; urinary tract infections; post-surgery infections on or caused by invasive devises; endocarditis by intravenous administration of contaminated drug solutions; bacterial infections in patients with acquired immunodeficiency syndrome, cancer chemotherapy, steroid therapy, hematological malignancies, organ transplantation, renal replacement therapy, and other situations with severe neutropenia; community-acquired respiratory tract infections; meningitis; folliculitis and infections of the ear canal caused by contaminated waters; malignant otitis externa in the elderly and diabetics; osteomyelitis of the caleaneus in children; eye infections commonly associated with contaminated contact lens; Skin infections such as nail infections in people whose hands are frequently exposed to water; gastrointestinal tract infections; and muscoskeletal system infections. Of the cocci bacteria, *micrococcus* and *staphylococcus* species are commonly associated with the skin, and *Streptococcus* species are commonly associated with tooth enamel and contribute to tooth decay. Of the rods family, bacteria *Bacillus* species produce endospores seen in various stages of development in the photograph and *B. cereus* cause a relatively mild food poisoning, especially due to reheated fried food. Of the *vibrio* species, *V. cholerae* is the most common bacteria and causes cholera, a severe diarrhea disease resulting from a toxin produced by bacterial growth in the gut. Of the spiral bacteria, rhodospirillum and *Treponema pallidum* are the common species to cause infection (e.g., *Treponema pallidum* causes syphilis). Spiral bacteria typically grow in shallow anaerobic conditions and can photosynthesize to obtain energy from sunlight.

Selection of Subjects Administered Gramicidin A Peptide Analogs and Derivatives Compositions In some embodiments, a subject amenable for the methods described herein, or for the administration with a composition comprising at least one Gramicidin A peptide analog or Gramicidin A peptide analog derivative having reduced cytotoxicity and increased solubility relative to wild-type Gramicidin A or SEQ ID NO: 2, as described herein. is selected based on the desired treatment regime. For instance, a subject is selected for treatment if the subject has a bacterial infection where the bacteria is, for example, a gram-positive bacteria, or where the subject has been non-responsive to prior therapy or administration with an antimicrobial agent.

In some embodiments, a subject is selected for the treatment methods and administration of the therapeutic compounds described herein, based on having a particular condition or being in a situation in which there is increased risk of development of a bacterial infection or likelihood of being exposed to a infectious bacterium Such situations and subjects include, but are not limited to burn wound patients; post-surgical subjects; post-surgical subjects having an invasive device; HIV positive or AIDs patients; subjects having or having had cancer chemotherapy; subjects having or having had steroid therapy; subjects having a hematological malignancy; subject having or having had an organ transplantation, renal replacement therapy, and/or other situations with severe neutropenia; elderly subjects; and/or newborn infants.

In some embodiments, a subject is selected for the administration with the compositions comprising Gramicidin A peptide analogs or Gramicidin A peptide analog derivatives having reduced cytotoxicity and increased solubility relative to wild-type Gramicidin A or SEQ ID NO: 2 as disclosed herein by identifying a subject that needs a specific treatment regimen, and is administered a Gramicidin A peptide analog or Gramicidin A peptide analog derivative concurrently with, or prior to, or after administration with one or more additional therapeutic agents.

In some embodiments, the methods and compositions described herein can be used prophylactically as a means to prevent the development of an infection caused or contributed to by MRSA, MRSE, VISA, VRSA, VRE and Clostridia, or to reduce the likelihood of the development of VISA or VRSA, e.g. from an MRSA infection. Medicaments and/or methods for prophylactic use can be administered or applied to any person or mammal at risk of developing an infection caused or contributed to by MRSA, MRSE, VISA, VRSA, VRE and Clostridia. For example, people working in care homes, nursing homes, sports centres, community centres, shops, restaurants, cafes, nurseries and/or schools may require prophylactic treatments.

The compositions and methods described herein can also be useful in institutions housing, sheltering, caring or otherwise holding people or patients vulnerable to or "at risk" of developing or contracting an antibiotic-resistant bacterial strain, such as, for example, MRSA, MRSE, VISA, VRSA, VRE and Clostridia. The compositions and methods can be particularly useful in hospitals, nursing homes, nurseries and/or schools. More generally, an elderly, young or immunocompromised person or patient can particularly benefit from the medicaments and methods described herein. Moreover, the methods and compositions described herein can be particularly useful to those undergoing a prolonged stay in hospital, for example in an intensive care facility.

Administration, Dosages, and Durations

A Gramicidin A peptide analog or Gramicidin A peptide analog derivative having reduced cytotoxicity and increased solubility relative to wild-type Gramicidin A can be formulated, dosed, and administered in a fashion consistent with good medical practice for use in the treatment of the infections described herein. Factors for consideration in this context include the particular bacterial, fungal, or viral species being treated, the particular subject being treated, the clinical condition of the individual subject, the site of delivery of the agent, the method of administration, the scheduling of administration, and other factors known to medical practitioners.

Accordingly, the "therapeutically effective amount" of a Gramicidin A peptide analog or Gramicidin A peptide analog derivative having reduced cytotoxicity and increased solubility relative to wild-type Gramicidin A to be administered is governed by such considerations, and, as used herein, refers to the minimum amount necessary to prevent, ameliorate, or treat, or stabilize, a disorder or condition mediated by an infection by a microorganism. Thus, the therapeutically effective amount of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, or SEQ ID NO: 7, is the minimum amount necessary to, for example, increase the time of survival of the subject, to inhibit or prevent gene expression of the microorganism, replication of the microorganism, transmission of the microorganism, or to treat or prevent the occurrence or recurrence of an infection by the microorganism.

An effective amount as used herein also includes an amount sufficient to delay the development of a symptom of the microbial infection, alter the course of the microbial infection (for example, but not limited to, slow the progression of a symptom of the microbial infection), or reverse a symptom of the microbial infection. Thus, it is not possible to specify the exact "effective amount." However, for any given case, an appropriate "effective amount" can be determined by one of ordinary skill in the art using only routine experimentation.

Effective amounts, toxicity, and therapeutic efficacy of the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be determined by standard pharmaceutical procedures in cell cultures or experimental animals, and as described herein, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the Gramicidin A peptide analog), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Depending on the type and severity of the disease, about 1 µg/kg to 100 mg/kg (e.g., 0.1-20 mg/kg) of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, is an initial candidate dosage range for administration to the subject, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until the infection is treated or cleared, as measured by the methods described above or known in the art. However, other dosage regimens can be useful. The progress of the therapeutic methods described herein is easily monitored by conventional techniques and assays, such as those described herein, or known to one of skill in the art.

The duration of the therapeutic methods described herein can continue for as long as medically indicated or until a desired therapeutic effect (e.g., those described herein) is achieved. In certain embodiments, administration of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, is continued for at least 1 month, at least 2 months, at least 4 months, at least 6 months, at least 8 months, at least 10 months, at least 1 year, at least 2 years, at least 3 years, at least 4 years, at least 5 years, at least 10 years, at least 20 years, or for at least a period of years up to the lifetime of the subject.

The Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be administered to a subject, e.g., a human subject, in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration can be used if, for example, extensive side effects or toxicity is associated with the particular peptide analog. An ex vivo strategy can also be used for therapeutic applications.

Exemplary modes of administration of the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, include, but are not limited to, injection, infusion, inhalation (e.g., intranasal or intratracheal), ingestion, rectal, and topical (including buccal and sublingual) administration. The phrases "parenteral administration" and "administered parenterally" as used herein, refer to modes of administration other than enteral and topical administration, usually by injection. As used herein, "injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, other than directly into a target site, tissue, or organ, such as the lung, such that it enters the subject's circulatory system and, thus, is subject to metabolism and other like processes.

In some embodiments, the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, are administered by intravenous infusion or injection. In some embodiments, where local treatment is desired, for example, at or near a site of an infection or lymph node, the Gramicidin A peptide analog or Gramicidin A peptide analog derivative having reduced cytotoxicity and increased solubility relative to wild-type Gramicidin A, such as a peptide analog of SEQ ID NO: 3-SEQ ID NO: 8, can be administered by a local method of administration. Additionally, in some embodiments, the Gramicidin A peptide analogs or Gramicidin A peptide analog derivatives, such as a peptide analog of SEQ ID NO: 3-SEQ ID NO: 8, described herein can be administered by pulse infusion. Preferably the dosing is given by injections, most preferably intravenous or subcutaneous injections, depending in part on whether the administration is brief or chronic.

Pharmaceutical Formulations

Therapeutic formulations of Gramicidin A peptide analogs or Gramicidin A peptide analog derivatives having reduced cytotoxicity and increased solubility relative to wild-type Gramicidin A described herein can be prepared, in some aspects, by mixing a, for example, Gramicidin A peptide analog having the desired degree of purity with one or more pharmaceutically acceptable carriers, excipients or stabilizers (Remington's Pharmaceutical Sciences 16th edition, Osol, A. Ed. (1980)), in the form of lyophilized formulations or aqueous solutions. Such therapeutic formulations of the Gramicidin A peptide analogs or Gramicidin A peptide analog derivatives described herein include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the Gramicidin A peptide analogs or Gramicidin A peptide analog derivatives described herein, from one organ, or portion of the body, to another organ, or portion of the body.

Some non-limiting examples of acceptable carriers, excipients, or stabilizers that are nontoxic to recipients at the dosages and concentrations employed, include pH buffered solutions such as phosphate, citrate, and other organic acids; antioxidants, including ascorbic acid and methionine; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, HDL, LDL, or immunoglobulins; hydrophilic polymers, such as polyvinylpyrrolidone; amino acids such as glycine, glutamine, asparagine, histidine, arginine, or lysine; monosaccharides, disaccharides, and other carbohydrates including mannose, starches (corn starch or potato starch), or dextrins; cellulose, and its derivatives, such as sodium carboxymethyl cellulose, methylcellulose, ethyl cellulose, microcrystalline cellulose and cellulose acetate; chelating agents such as EDTA; sugars such as sucrose, glucose, lactose, mannitol, trehalose or sorbitol; salt-forming counter-ions such as sodium; metal complexes (e.g. Zn-protein complexes); glycols, such as propylene glycol; polyols, such as glycerin; esters, such as ethyl oleate and ethyl laurate; agar; buffering agents, such as magnesium hydroxide and aluminum hydroxide; alginic acid; pyrogen-free water; isotonic saline; Ringer's solution; polyesters, polycarbonates and/or polyanhydrides; C2-C12 alcohols, such as ethanol; powdered tragacanth; malt; and/or non-ionic surfactants such as TWEEN™, PLURONICS™ or polyethylene glycol (PEG); and/or other non-toxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments, the therapeutic formulations comprising Gramicidin A peptide analogs or Gramicidin A peptide analog derivatives having reduced cytotoxicity and increased solubility relative to wild-type Gramicidin A described herein comprise a pharmaceutically acceptable salt, typically, e.g., sodium chloride, and preferably at about physiological concentrations. Optionally, the formulations described herein can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

In some embodiments of the aspects described herein, a Gramicidin A peptide analog or Gramicidin A peptide analog derivative having reduced cytotoxicity and increased solubility relative to wild-type Gramicidin A described herein can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, a Gramicidin A peptide analog or Gramicidin A peptide analog derivative having reduced cytotoxicity and increased solubility relative to wild-type Gramicidin A described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and 35 U.S. Pat. No. 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, parenteral dosage forms of the Gramicidin A peptide analogs or Gramicidin A peptide analog derivatives having reduced cytotoxicity and increased solubility relative to wild-type Gramicidin A described herein can be administered to a subject with an infection or at increased risk for infection by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Topical dosage forms of the Gramicidin A peptide analogs or Gramicidin A peptide analog derivatives having reduced cytotoxicity and increased solubility relative to wild-type Gramicidin A described herein, are also provided in some embodiments, and include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990). and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer a Gramicidin A peptide analog or Gramicidin A peptide analog derivative having reduced cytotoxicity and increased solubility relative to wild-type Gramicidin A described herein, include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the peptide analogs and derivatives described herein are well known to those skilled in the pharmaceutical arts, and depend on the particular tissue or organ to which a given pharmaceutical composition or dosage form will be applied. In addition, depending on the specific tissue to be treated, additional components may be used prior to, in conjunction with, or subsequent to treatment with a Gramicidin A peptide analogs or Gramicidin A peptide analog derivative described herein. For example, penetration enhancers can be used to assist in delivering the active ingredients to or across the tissue.

In some embodiments, the Gramicidin A peptide analogs or Gramicidin A peptide analog derivatives having reduced cytotoxicity and increased solubility relative to wild-type Gramicidin A described herein, are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and can be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

Typical oral dosage forms of the compositions are prepared by combining the pharmaceutically acceptable salt of a Gramicidin A peptide analog or Gramicidin A peptide analog derivative having reduced cytotoxicity and increased solubility relative to wild-type Gramicidin A in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the Gramicidin A peptide analogs or Gramicidin A peptide analog derivatives having reduced cytotoxicity and increased solubility relative to wild-type Gramicidin A described herein, such as those of SEQ ID NO: 3-SEQ ID NO: 8. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the orthopoxvirus inhibitors described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the Gramicidin A peptide analogs or Gramicidin A peptide analog derivatives having reduced cytotoxicity and increased solubility relative to wild-type Gramicidin A described herein, such as the peptide analogs of SEQ ID NO: 3-SEQ ID NO: 8, further encompass, in some embodiments, anhydrous pharmaceutical compositions and dosage forms comprising the orthopoxvirus inhibitors described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

A Gramicidin A peptide analog or Gramicidin A peptide analog derivative having reduced cytotoxicity and increased solubility relative to wild-type Gramicidin A described herein, can be administered directly to the airways in the form of an aerosol or by nebulization. Accordingly, for use as aerosols, in some embodiments, a Gramicidin A peptide analog or Gramicidin A peptide analog derivative having reduced cytotoxicity and increased solubility relative to wild-type Gramicidin A described herein, can be packaged in a pressurized aerosol container together with suitable propellants, for example, hydrocarbon propellants like propane, butane, or isobutane with conventional adjuvants. In other embodiments, the orthopoxvirus inhibitor can be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the small molecule pyridomyrimidone orthopoxvirus inhibitors of Formula (I), e.g., 4-acetyl-2,3,7,8-tetrahydro-3-phenylpyrido[1,2-f]pyrimidin-1-one or CMLDBU6128. Exemplary gases include, but are not limited to, nitrogen, argon or helium.

In other embodiments, a Gramicidin A peptide analog or Gramicidin A peptide analog derivative having reduced cytotoxicity and increased solubility relative to wild-type Gramicidin A described herein, can be administered directly to the airways in the form of a dry powder. For use as a dry powder, a Gramicidin A peptide analog or Gramicidin A peptide analog derivative can be administered by use of an inhaler. Exemplary inhalers include metered dose inhalers and dry powdered inhalers.

Suitable powder compositions include, by way of illustration, powdered preparations of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

In some embodiments of the aspects described herein, the pharmaceutical formulations comprising the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can further comprise more than one active compound as necessary for the particular indication being treated, preferably those with complementary activities that do not adversely affect each other. For example, in some embodiments, it can be desirable to further provide antibodies that bind to and/or neutralize the microorganism being treated or inhibited in the formulation comprising the peptide analog or peptide analog derivative.

In other embodiments, the formulations comprising the Gramicidin A peptide analogs or Gramicidin A peptide analog derivatives having reduced cytotoxicity and increased solubility relative to wild-type Gramicidin A described herein, can further comprise an antibiotic, cytokine, growth inhibitory agent and/or nucleoside analog. Such molecules are suitably present in combination in amounts that are effective for the purpose intended.

In some embodiments, the active ingredients of the formulations comprising Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments of these aspects, the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be administered to a subject by controlled- or delayed-release means. Ideally, the use of an optimally designed controlled-release preparation in medical treatment is characterized by a minimum of drug substance or agent being employed to cure or control the condition in a minimum amount of time. Advantages of controlled-release formulations include: 1) extended activity of the agent; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control an peptide analog's or derivative's onset of action, duration of action, plasma levels within the therapeutic window, and peak blood levels. In particular, controlled- or extended-release dosage forms or formulations can be used to ensure that the maximum effectiveness of the Gramicidin A peptide analog or Gramicidin A peptide analog derivative having reduced cytotoxicity and increased solubility relative to wild-type Gramicidin A, such as a peptide analog of SEQ ID NO: 3-SEQ ID NO: 8, is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated ins entirety herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm & Haas, Spring House, Pa. USA).

In some embodiments of the aspects, the Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, for use in the various therapeutic formulations and compositions, and methods thereof, described herein, is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic infections, as each pulse dose can be reduced and the total amount of a peptide analog or derivative administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations comprising the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, to be used for in vivo administration are preferably sterile. This is readily accomplished by filtration through, for example, sterile filtration membranes, and other methods known to one of skill in the art.

Efficacy of the Treatment

One key advantage of the methods, uses and compositions comprising the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, is the ability of producing marked antimicrobial effects in a human subject without causing significant toxicities or adverse effects, as demonstrated herein. The efficacy of the treatments described herein can be measured by various parameters commonly used in evaluating treatment of infections, including but not limited to, microbial load, rate of microbial replication, time to symptoms of infection, duration of survival, overall response rate, duration of response, and quality of life.

As used herein, the terms "treat," "treatment," "treating," or "amelioration" refer to therapeutic treatments, wherein the object is to reverse, alleviate, ameliorate, inhibit, slow down or stop the progression or severity of a condition associated with, an infection, disease or disorder. The term "treating" includes reducing or alleviating at least one adverse effect or symptom of a condition, disease or disorder associated with a orthopoxvirus infection, such as, but not limited to, fevers or skin lesions. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, to a subject in order to alleviate a symptom of a microbial infection, such as an infection with a gram-positive bacteria, or other such disorder. As used herein, "alleviating a symptom of an infection" is ameliorating or reducing any condition or symptom associated with the infection. As compared with an equivalent untreated control, such reduction or degree of prevention is at least 5%, 10%, 20%, 40%, 50%, 60%, 80%, 90%, 95%, or 100% as measured by any standard technique. Ideally, the infection is completely cleared as detected by any standard method known in the art. A patient who is being treated for an infection is one who a medical practitioner has diagnosed as having such a condition. Diagnosis can be by any suitable means. Diagnosis and monitoring can involve, for example, detecting the level of infected cells or microbial cells in a biological sample (for example, a tissue or lymph node sample, blood test, or urine test), using, for example, PCR assays for detection of microbial genome, ELISA assays for detection of microbial antigens, detecting the level of a surrogate marker of the infection in a biological sample, detecting symptoms associated with the specific infection, or detecting immune cells involved in the immune response typical of such infections.

Combination Therapies

In some embodiments, the compositions and methods comprising the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, further comprise administration or treatment with one or more additional therapies specific for the microorganism being treated, or any broad-spectrum therapy, such as a broad spectrum antibiotic. Examples of such additional therapies include, without limitation, neutralizing antibodies specific for the infectious agent, such as a gram-positive bacteria, vaccination, antibiotic therapies, 4'-thio-2'-deoxynucleosides, therapeutic cytokine agents, such as interferon (IFN), interferon α-2a, interferon α-2b, consensus interferon (CIFN), and interleukin-12, ursodeoxycholic acid (UDCA), Nevirapine, ribavirin, amantadine, remantadine, and glycyrrhizin, or any combination of these therapies.

For the treatment or prevention of orthopoxvirus infections in such embodiments comprising combination therapies, the appropriate dosage of Gramicidin A peptide analog or Gramicidin A peptide analog derivative described herein, such as a peptide analog of SEQ ID NO: 3-SEQ ID NO: 8, will depend on the type of infection to be treated, as defined above, the severity and course of the infection, whether the Gramicidin A peptide analog or Gramicidin A peptide analog derivative is administered for preventive or therapeutic purposes, previous therapy, the subject's clinical history and response to the Gramicidin A peptide analog or Gramicidin A peptide analog derivative, and the discretion of the attending physician. The Gramicidin A peptide analog or Gramicidin A peptide analog derivative is suitably administered to the subject at one time or over a series of treatments.

In those embodiments where a combination therapy regimen is applied, a Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, and one or more anti-microbial therapeutic agents as described herein are administered in a therapeutically effective or synergistic amount. As used in such embodiments encompassing combination therapies, a therapeutically effective amount is such that co-administration of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, and one or more other anti-microbial therapeutic agents, results in reduction or inhibition of the infection as described herein. A "therapeutically synergistic amount" is that amount of a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, and one or more other anti-microbial therapeutic agents necessary to synergistically or significantly reduce or eliminate conditions or symptoms associated with a particular infection In some embodiments, a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, and one or more other anti-microbial therapeutic agents can be administered simultaneously or sequentially in an amount and for a time sufficient to reduce or eliminate the occurrence or recurrence of an infection. In some embodiments, the Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, and one or more other anti-microbial therapeutic agents can be administered as maintenance or prophylactic therapy to prevent or reduce the likelihood of infection.

As will be understood by those of ordinary skill in the art, the appropriate doses of additional anti-microbial therapeutic agents will be generally around those already employed in clinical therapies, e.g., where the therapeutics are administered alone or in combination with other therapeutics. Variation in dosage will likely occur depending on the condition being treated. The physician administering treatment will be able to determine the appropriate dose for the individual subject.

The term "cytokine" is a generic term for proteins released by one cell population which act on another cell as intercellular mediators. Examples of such cytokines are lymphokines, monokines, and traditional polypeptide hormones. Included among cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12, IL-15, IL-17, IL-18, IL-21, IL-22, IL-23, IL-25, IL-27, IL-33; a tumor necrosis factor such as TNFalpha or TNF-beta; and other polypeptide factors including LIF and kit ligand (KL). As used herein, the term cytokine includes proteins from natural sources or from recombinant cell culture and biologically active equivalents of the native sequence cytokines.

In some embodiments, a Gramicidin A peptide analog or Gramicidin A peptide analog derivative having reduced cytotoxicity and increased solubility relative to wild-type Gramicidin A described herein, such as a peptide analog of SEQ ID NO: 3-SEQ ID NO: 8, can be administered together with at least one known antibacterial agent, antifungal agent, or anti-inflammatory agent selected from chloroxylenol (parachlorometaxylenol), acedapsone; acetosulfone sodium; alamecin; alexidine; amdinocillin; amdinocillin; pivoxil; amicycline; amifloxacin; amifloxacinmesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin, methylenedisalicylate; bacitracin zinc; bambermycins; benzoylpas calcium; berythromycin; betamicin sulfate; biapenem; biniramycin; biphenamine hydrochloride; bispyrithionemagsulfex; butikacin; butirosin sulfate; capreomycin sulfate; carbadox; carbenicillin disodium; carbenicillin, indanyl sodium; carbenicillin phenyl sodium; carbenicillin potassium; carumonam sodium; cefaclor; cefadroxil; cefamandole; cefamandolenafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime; proxetil; cefprozil; cefroxadine; cefsulodin sodium; ceftazidime; ceftibuten; ceftizoxime sodium; ceftriaxone sodium; cefuroxime; cefuroximeaxetil; cefuroximepivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicolpalmitate; chloramphenicolpantothenate complex; chloramphenicol sodium succinate; chlorhexidinephosphanilate; chlorhexidinediacetate, chlorhexidinedihydrochloride, chlorhexidinedigluconate, chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycinpalmitate hydrochloride; clindamycin phosphate; clofazimine; cloxacillinbenzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycyclinefosfatex; doxycyclinehyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycintromethamine; fumoxicillin; furazolium chloride; furazoliumtartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacinmesylate; loracarbef; mafenide; meclocycline; meclocyclinesulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensinsodiumr; monovalent silver salts, nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; octenidinedihydrochloride, octenidinediacetate, octenidinedigluconate, ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacinmesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillinpamoate; pivampicillinprobenate; polyhexamethylenebiguanide (polyhexanide hydrochloride, PHMB); polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicinstearate; rosoxacin; roxarsone; roxithromycin; sancycline; sanfetrinem sodium; sarmoxicillin; sarpicillin; scopafungin; silver acetate; silver nitrate, nanocrystalline silver, silver polystyrene sulfonate (cross-linked" and non-cross-linked); silver carboxymethyl cellulose, silver polysaccharides (such as silver chondroitin sulfate and the like), silver carbene compounds, sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadiazine silver; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazolediolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillincresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin and/or zorbamycin.

Other Applications and Uses of the Gramicidin A Peptide Analogs and Derivatives

Provided herein are novel Gramicidin A peptide analogs and derivatives having potent anti-microbial activity, increased water solubility and decreased cytotoxicity relative to the wild-type Gramicidin A peptide of SEQ ID NO: 2. As described herein, in some aspects, these Gramicidin A peptide analogs and derivatives are useful in therapeutic compositions and methods thereof for treating subjects or patients having or at risk for an infection. However, the Gramicidin A peptide analogs or Gramicidin A peptide analog derivatives described herein having reduced cytotoxicity and increased solubility relative to wild-type Gramicidin A, such as a peptide analog of SEQ ID NO: 3-SEQ ID NO: 8, are also useful in applications and methods for inhibiting growth and replication of a microorganism outside of an organism or outside the body, such as, for example, on various surfaces, or for example, in a food product.

Accordingly, in some aspects provided herein are Gramicidin A peptide analogs or Gramicidin A peptide analog derivatives described herein having reduced cytotoxicity and increased solubility relative to wild-type Gramicidin A, for use in methods of inhibiting or preventing formation of a biofilm on a surface, such methods comprising contacting or applying to a surface a Gramicidin A peptide analog or derivative to the surface. In some embodiments of such methods, the Gramicidin A peptide analog or Gramicidin A peptide analog derivative described herein having reduced cytotoxicity and increased solubility relative to wild-type Gramicidin A is contacted to the surface via a bacteriophage engineered to express the analog or derivative. Such bacteriophages are well known in the art and are encompassed for use in the methods and compositions as disclosed herein. In other such embodiments, the Gramicidin A analog or derivative is directly contacted with the surface in which bacterial film formation is to be inhibited. In some such embodiments, the bacterial biofilm is in a medical, or industrial, or biotechnological setting. A biofilm is typically resistant to phagocytosis by host immune cells and the effectiveness of antibiotics at killing bacteria in biofilm structures can be reduced by 10 to 1000 fold. Biofilm production and arrangement is governed by quorum sensing systems. The disruption of the quorum sensing system in bacteria such as *P. aeruginosa* is an important anti-pathogenic activity as it disrupts the biofilm formation and also inhibits alginate production The methods and compositions as disclosed herein comprising a Gramicidin A peptide analog or Gramicidin A peptide analog derivative having reduced cytotoxicity and increased solubility relative to wild-type Gramicidin A, such as a peptide analog of SEQ ID NO: 3-SEQ ID NO: 8, can also be used in various fields as where antiseptic treatment or disinfection of materials it required, for example, surface disinfection, including for use in bioremediation, such as industry settings, including cleaning of heating and cooling systems, such as HVAC systems and the like.

The methods and compositions as disclosed herein comprising a Gramicidin A peptide analogs or Gramicidin A peptide analog derivatives having reduced cytotoxicity and increased solubility relative to wild-type Gramicidin A, such as a peptide analog of SEQ ID NO: 3-SEQ ID NO: 8, can be used to treat microorganisms infecting a cell, group of cells, or a multi-cellular organism.

The compositions comprising Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be used to treat and reduce bacterial infections in transmitting parts of HVAC systems likely to be contaminated, as well as the entire water distribution and storage system.

In some embodiments, the compositions comprising Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be used in methods reduce the rate of growth and/or kill either gram positive, gram negative, or mixed flora bacteria or other microorganisms.

In some embodiments, the compositions comprising Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, can be used to treat an already drug resistant bacterial strain such as Methicillin-resistant *Staphylococcus aureus* (MRSA) or Vancomycin-resistant *enterococcus* (VRE) of variant strains thereof. In some such embodiments, the compositions and methods of use comprising Gramicidin A peptide analogs or Gramicidin A peptide analog derivatives having reduced cytotoxicity and increased solubility relative to wild-type Gramicidin A described herein, such as a peptide analog of SEQ ID NO: 3-SEQ ID NO: 8, are contemplated for use with or in methods with one or more combinations of other agents, such as other antimicrobial agents and/or antibiotics to fight gram-positive bacteria that maintain resistance to certain drugs.

The compositions provided herein can also be used as sterilizing or cleaning aids for use, for example, on surfaces to reduce and/or eliminate contamination by MRSA, MRSE, VISA, VRSA, VRE and/or Clostridia. By way of example, combinations comprising a Gramicidin A peptide analog or derivatives, with an agent active on a bacterial cell surface selected from the group consisting of colistin, nisin, D-cycloserine, fosfomycin or polymixin B, and derivatives thereof, can be administered, or can be prepared for application to any surface suspected of being contaminated by MRSA, MRSE, VISA, VRSA, VRE and/or Clostridia. For example, the compositions described herein can be added to or diluted in an appropriate excipient or solution prior to use as a sterilizing or cleaning agent. Exemplary excipients are described above. Such sterilizing or cleaning solutions can be used to decontaminate, for example, furniture, floors, equipment including for example specialised hospital equipment and/or surgical equipment.

The term "surface" used herein, refers to any surface whether medical or industrial, that provides an interface between a fluid and a solid. The interface between fluid and solid can be intermittent, and can be caused by flowing or stagnant fluid, aerosols, or other means for air-borne fluid exposure. The surface described herein, refers more specifically to a plane whose mechanical structure is compatible with the adherence of bacteria such as *S. aureus* and *Enterococcus* species. In the context of the compositions and methods described herein, the terminology "medical or veterinary surface" encompasses the inner and outer aspects of various instruments and devices, both disposable and non-disposable. Examples include the entire spectrum of medical devices.

As used herein, the terminology "surfaces found in medical environments" includes the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopaedic pins, plates and implants; catheters and other tubes (including urological and biliary tubes, endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Surfaces found in the medical environment also include the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilised drugs in nebulisers and of aesthetic agents. Also included are those surfaces intended as biological barriers to infectious organisms in medical settings, such as gloves, aprons and face-shields. Commonly used materials for biological barriers may be latex-based or non-latex based, such as vinyl. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Additionally, or alternatively, the compositions and methods described herein can be useful in community centres, sports facilities, shops, restaurants, cafes or other places where transmission of bacteria, such as antibiotic resistant bacteria, for example, MRSA, MR SE, VISA, VRSA, VRE and Clostridia, is likely.

Embodiments of the various aspects described herein can be illustrated by the following numbered paragraphs.

1. An anti-microbial composition comprising at least one Gramicidin A peptide analog or derivative having reduced cytotoxicity and increased solubility relative to wild-type Gramicidin A having the amino acid sequence of SEQ ID NO: 2.
2. The anti-microbial composition of paragraph 1, wherein the at least one Gramicidin A peptide analog or derivative comprises the amino acid sequence of SEQ ID NO: 2 having one or more of the d-Leucine amino acids at positions 10, 12, or 14 replaced or substituted.
3. The anti-microbial composition of paragraph 1, wherein the at least one Gramicidin A peptide analog or derivative comprises the amino acid sequence of SEQ ID NO: 2 having at least two of the d-Leucine amino acids at positions 10, 12, or 14 replaced or substituted.
4. The anti-microbial composition of paragraph 1, wherein the at least one Gramicidin A peptide analog or derivative comprises the amino acid sequence of SEQ ID NO: 2 having all three of the d-Leucine amino acids at positions 10, 12, and 14 replaced or substituted.
5. The anti-microbial compositions of any one of paragraphs 2-4, wherein the amino acids d-Leucine amino acids at positions 10, 12, 14 are replaced or substituted with a cationic amino acid.
6. The anti-microbial compositions of paragraph 5, wherein the cationic amino acid is d-lysine or d-arginine.
7. The anti-microbial compositions of any one of paragraphs 2-6, wherein the solubility of the Gramicidin A peptide analog or derivative is increased relative to wild-type Gramicidin A by at least 10-fold.
8. The anti-microbial compositions of any one of paragraphs 2-7, wherein the cytotoxicity of the Gramicidin A peptide analog or derivative is reduced relative to wild-type Gramicidin A by at least 2-fold.
9. The anti-microbial composition of paragraph 1, wherein the at least one Gramicidin A peptide analog or derivative comprises an amino acid sequence of SEQ ID NO: 3.
10. The anti-microbial composition of paragraph 1, wherein the at least one Gramicidin A peptide analog or derivative comprises an amino acid sequence of SEQ ID NO: 4.
11. The anti-microbial composition of paragraph 1, wherein the at least one Gramicidin A peptide analog or derivative comprises an amino acid sequence of SEQ ID NO: 5.
12. The anti-microbial composition of paragraph 1, wherein the at least one Gramicidin A peptide analog or derivative comprises an amino acid sequence of SEQ ID NO: 6.
13. The anti-microbial composition of paragraph 1, wherein the at least one Gramicidin A peptide analog or derivative comprises an amino acid sequence of SEQ ID NO: 7.
14. The anti-microbial composition of paragraph 1, wherein the at least one Gramicidin A peptide analog or derivative comprises an amino acid sequence of SEQ ID NO: 8.
15. The anti-microbial compositions of any one of paragraphs 2-8, wherein the d-Leucine amino acid at position 10 is replaced or substituted with Nε-trimethylated lysine.
16. The anti-microbial compositions of any one of paragraphs 2-8, wherein the d-Leucine amino acid at position 14 is replaced or substituted with Nε-trimethylated lysine.
17. The anti-microbial compositions of any one of paragraphs 2-8, wherein the d-Leucine amino acid at positions 10 and 14 are replaced or substituted with Nε-trimethylated lysine.
18. The anti-microbial composition of any one of paragraphs 1-17, further comprising a pharmaceutically acceptable carrier.
19. A method of inhibiting growth or replication of a microorganism, the method comprising contacting a biological sample or a surface found in a medical environment with the anti-microbial composition of any one of paragraphs 1-18 in an amount sufficient to inhibit growth or replication of the microorganism.
20. The method of paragraph 19, wherein the microorganism is a bacteria.
21. The method of paragraph 20, wherein the bacteria is a Gram-positive bacteria.

22. A method of treating or inhibiting a microbial infection in a subject having or at risk for a microbial infection, comprising administering to the subject a therapeutically effective amount of the anti-microbial composition of any one of paragraphs 1-18.
23. The method of paragraph 22, wherein the microbial infection is a bacterial infection.
24. The method of paragraph 23, wherein the bacterial infection is caused by a Gram-positive bacteria.
25. The method of any one of paragraphs 22-24, further comprising the step of selecting the subject having or at risk for a microbial infection.

EXAMPLES

The rapid development of multidrug resistance by pathogenic bacteria poses a serious threat to the society and demands new antibiotics with different mechanisms of action.[1] Within the past decade, a significant amount of effort has been paid to developing membrane active peptides [2] and their functional analogues[3] as novel antibiotics. These effort were based on studies that came from antimicrobial peptides (AMPs), a large collection of short peptides (12-80 amino acids) that kill a wide spectrum of bacteria and serve as the frontline of the innate immune system.[4] The majority of AMPs display a positive net charge and an amphipathic structure. Different from conventional antibiotics, which often target a specific step of biosynthesis, AMPs are thought, without wishing to be bound or limited by theory, to function by disrupting the plasma membrane of bacterial cells. [5] This unique mechanism makes it difficult for bacteria to acquire resistance. [6] However, the development of AMPs into systemic antibiotics has been slow because of their low efficacy, toxicity, and limited tissue distribution. Rational improvement of AMPs has been difficult largely due to lack of detailed mechanistic understanding. For instance, it remains unclear whether AMPs form permanent pores in membranes; the underlying reasons of bacterial specificity of AMPs are still being further investigated as well.[7]

In contrast to the majority of AMPs, a small number of peptides do have clearly defined mechanisms of membrane lysis. A prominent example of such peptides is gramicidin A (gA), a fifteen-residue linear peptide isolated from *Bacillus brevis*. [8] Composed of alternating D- and L-amino acids, gA folds into a β-helix with an internal pore (FIG. 1A).[9] The length of the β-helix matches well with one leaflet of a membrane; inter-leaflet dimerization yields a transmembrane channel with a diameter of 4 Å (FIG. 1B). The channel allows facile diffusion of water and a selection of monovalent cations (e.g. Na+, K+), but it is impermeable to larger species including polyvalent cations. The ion-selective channel activity has made gA a popular model membrane protein and a blueprint for engineering functional channel sensors.[10] Also due to the channel activity, gA displays potent antibiotic activity. [11] In fact, it is used as one of the active ingredients of the commercialized antibiotic ointment Polysporin in Canada. However, the peptide is essentially insoluble in water (<50 nM) and induces hemolysis under concentrations required to cause bacteria cell death (vide infra). Consequently, its therapeutic usage has been limited to topical applications. Provided herein, are novel gA mutants that have reduced toxicity and increased solubility and their use in therapeutic applications as systemic antibiotics.

It is well known that bacterial cell membranes comprise a large fraction of negatively charged lipids, and therefore display greater affinity to cationic peptides. This is why most AMPs carry a positive charge. We designed novel gA mutant peptides based on strategic incorporation of cationic residues into wild-type gA in order to provide bacterial specificity by retaining channel forming potential. In addition, the charged residues greatly improve the water solubility of gA mutants.

A close examination of the dimeric channel structure revealed that the D-leucines at positions 10, 12 and 14 are suitable for mutation/modification because they locate at the membrane-water interface, where charged side chains can be accommodated without altering the channel structure. [12] Accordingly, a series of gA mutants were synthesized with one or multiple D-leucines replaced with D-lysines (as shown at Table 1). All peptides were synthesized through solid phase peptide synthesis, cleaved off the resin with eolamine, and then treated with TFA to remove the side chain protecting groups. Interestingly, incorporation of D-lysines into the gA sequence made the peptides much easier to synthesize and purify. All peptides are characterized with LC-MS for purity (>95%) and integrity. As demonstrated herein, D-lysine incorporation dramatically improves water solubility of gA mutant peptide. In contrast to wild type gA that is not detectable by Trp absorption, the mutants in aqueous media display characteristic Trp absorption spectrum with no indication of aggregation (FIG. 2). Peptide solubility increases with the number of D-lysine and does not depend on the position of the lysine residues. The triple lysine peptide, termed herein as "gA-5" is readily soluble at concentrations close to 100 µM, the solubility of which is better than the wild type by three orders of magnitude.

Antimicrobial activity of the gA mutants described herein was evaluated on four bacterial strains and the results compared to the wild type gA (Table 2). The bacteria strains tested included the gram-negative *E. coli* (BL 21), and gram-positives *B. subtilis* (ATCC 663), *S. aureus* (ATCC 6538) and *S. pyogenes* (ATCC 19615). The minimum inhibitory concentration (MIC) was determined by a standard microdilution procedure.[13] None of the peptides, including gA-WT, is effective in killing the gram-negative *E. coli*.[14] In sharp contrast, potent antimicrobial activity was observed against all three strains of gram-positive bacteria, with MIC values ranging from high nM to low µM. Interestingly, all gA mutants described herein, except gA-5, display MIC values essentially identical to that of gA-WT, indicating the charged residues do not compromise the channel forming potential of gA in bacterial membranes. A reduced potency against *S. aureus* was observed for the triple D-lysine mutant gA-5, with the MIC value greater 10 µM. However, gA-5 remained highly potent against *B. subtilis* and *S. Pyogenes*. The antimicrobial potency of the gA mutants described herein is equivalent to or better the best antimicrobial peptides reported to date.[2b, 15]

TABLE 1

Sequences of gA Mutants (SEQ ID NOS 2-8, respectively, in order of appearance)

| | |
|---|---|
| gA-WT | formyl-V-G-A-dL-A-dV-V-dV-<br>W-dL-W-dL-W-dL-W-NHCH$_2$CH$_2$OH |
| gA-1 | formyl-V-G-A-dL-A-dV-V-dV-<br>W-dK-W-dL-W-dL-W-NHCH$_2$CH$_2$OH |
| gA-2 | formyl-V-G-A-dL-A-dV-V-dV-<br>W-dL-W-dL-W-dK-W-NHCH$_2$CH$_2$OH |
| gA-3 | formyl-V-G-A-dL-A-dV-V-dV-<br>W-dK-W-dL-W-dK-W-NHCH$_2$CH$_2$OH |

TABLE 1-continued

Sequences of gA Mutants (SEQ ID NOS 2-8, respectively, in order of appearance)

| | |
|---|---|
| gA-WT | formyl-V-G-A-dL-A-dV-V-dV-<br>W-dL-W-dL-W-dL-W-NHCH$_2$CH$_2$OH |
| gA-4 | formyl-V-G-A-dL-A-dV-V-dV-<br>W-dK-W-dK-W-dL-W-NHCH$_2$CH$_2$OH |
| gA-5 | formyl-V-G-A-dL-A-dV-V-dV-<br>W-dK-W-dK-W-dK-W-NHCH$_2$CH$_2$OH |
| gA-6 | formyl-V-G-A-dL-A-dV-V-dV-<br>W-dR-W-dR-W-dR-W-NHCH$_2$CH$_2$OH |

To evaluate toxicity of the gA peptide analogs described herein, membrane activity against human red blood cells (hRBCs) was measuring using two complementary approaches (Table 2). A typical hemolytic assay [3e] monitors leakage of hemoglobin as a consequence of the peptide-induced membrane damage. In addition, specific evaluation of gA peptide analog-induced K+ leakage from red blood cells was performed using atomic emission spectroscopy,[16] in which K+ concentration can be assessed by its characteristic emission at 766.5 nm. The results show gA-WT is highly efficient in folding into hRBC membranes to give transmembrane channels. Half K+ leakage was observed with the peptide concentration of only 140 pM (KC$_{50}$, 140 pM). Hemoglobin release from hRBCs was observed with gA-WT at low μM concentrations (HC50, 5 μM), consistent with a lack of membrane selectivity of gA channel formation. Importantly, there is a concentration gap for the gA-triggered K+ leakage and hemoglobin release, indicating that gA-WT predominantly forms K+ specific channels (FIGS. 1A-1B) at low concentrations (<5 μM).

TABLE 2

Antibacterial and haemolytic activity (haemoglobin and K+ leakage) activity of gA

| | MICs [a], [b]/μM | | | | |
|---|---|---|---|---|---|
| | B. Subtilius | S. Aureus | S. Pyogenes | HC$_{50}$ [c] | KC$_{50}$ [d] |
| gA-WT | 2.5 | 2.5 | 0.16 | 5 | 1.40E-04 |
| gA-1 | 5 | 2.5 | 0.16 | 5~10 | 0.01 |
| gA-2 | 5 | 2.5 | 0.16 | 5~10 | 0.01 |
| gA-3 | 5 | 5 | 0.32 | >70 | 5~10 |
| gA-4 | 2.5 | 5 | 0.16 | >100 | 5~10 |
| gA-5 | 5 | >10 [e] | 0.62 | >100 | >100 |
| gA-6 | 2.5~5 | >10 [e] | 1.25 | 20 | nd |

Figure 7:
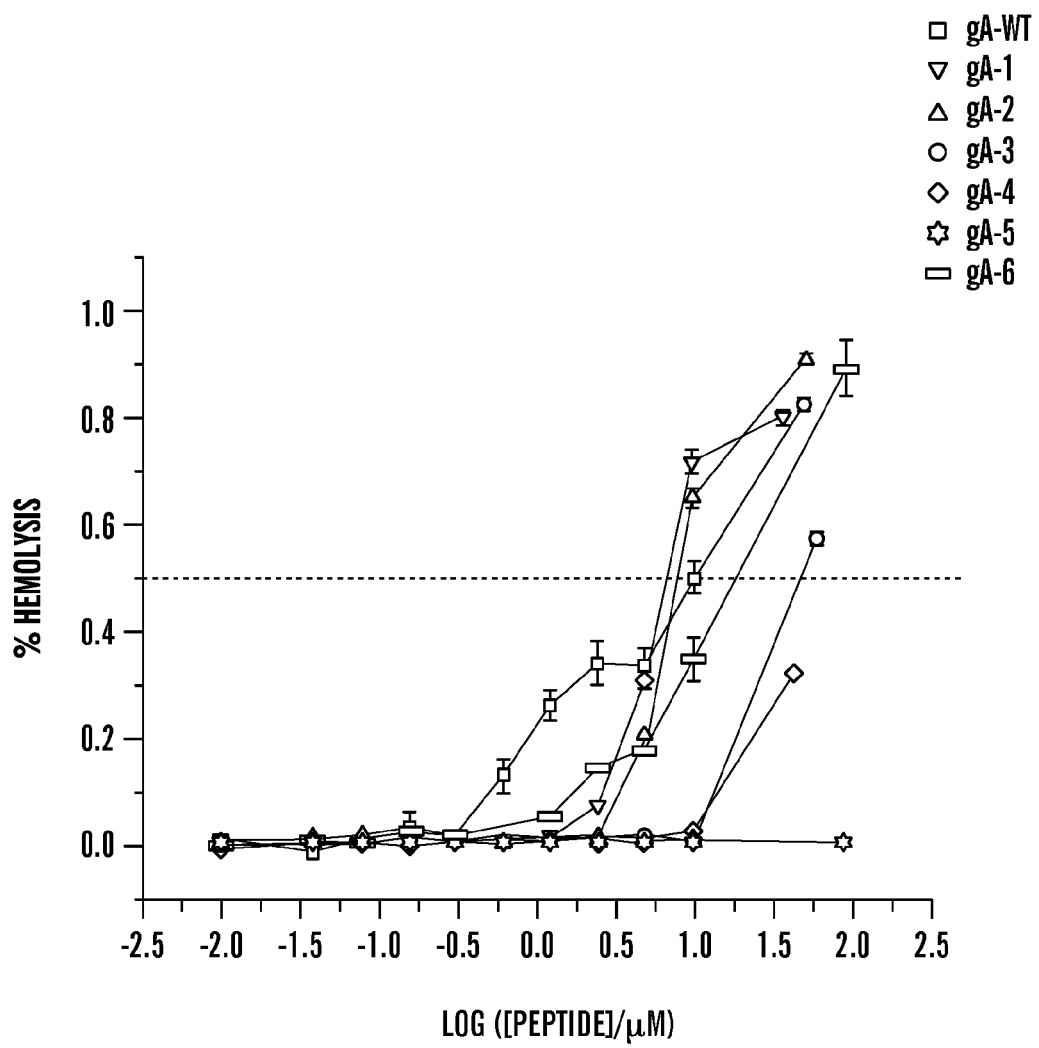
FIG. 7 shows concentration profiles of all gA variants in inducing hemoglobin leakage from hRBCs.
Figure 8:
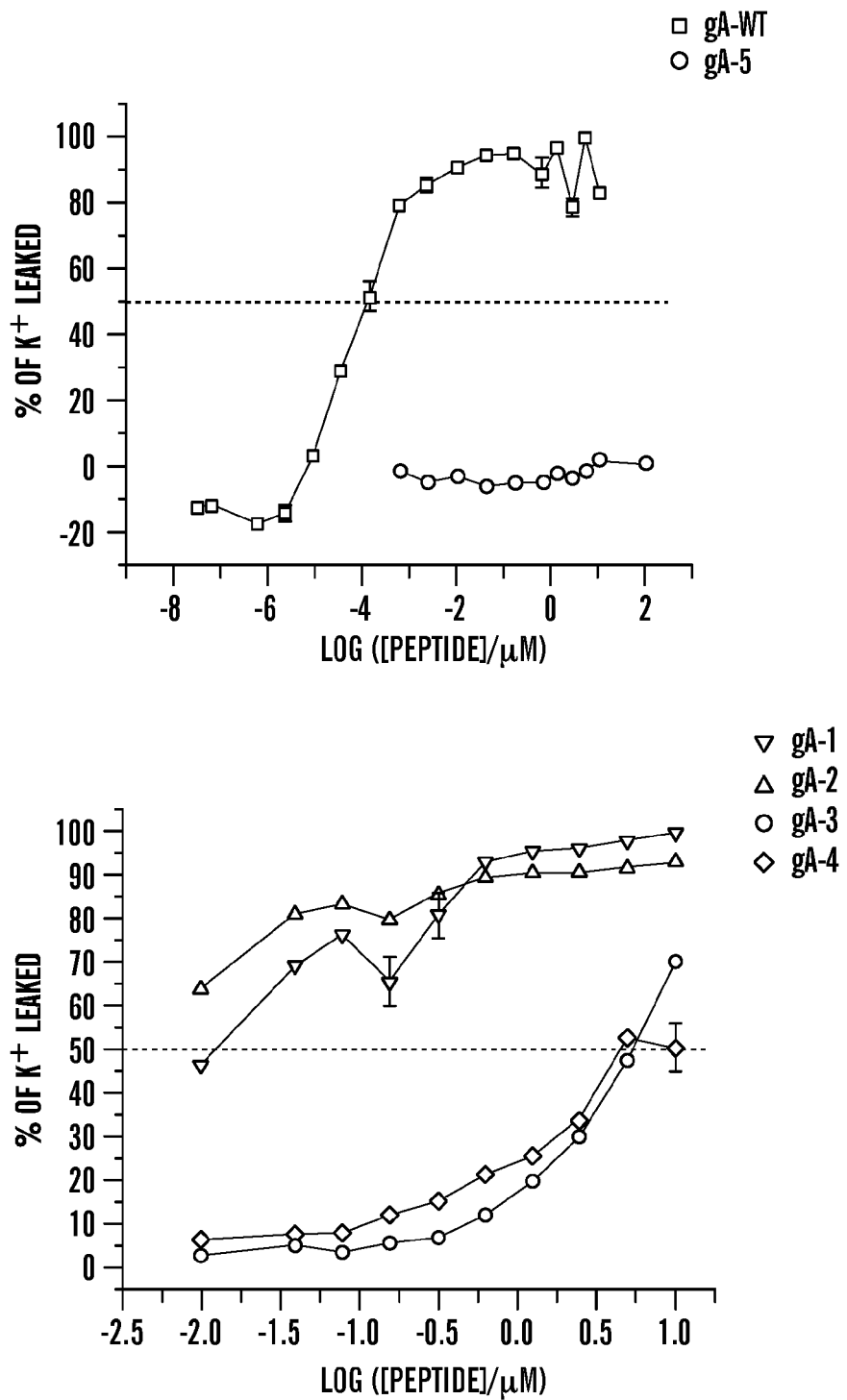
FIG. 8 shows concentration profiles of gA variants in inducing $K^+$ leakage from hRBCs.

MIC is the minimum inhibition concentration determined by a standard micro-dilution procedure;[13] Some representative MIC measurement traces are shown in FIG. 6.
[b] None of the peptides tested was active against E. coli (FIG. 6).
[c] HC$_{50}$ is the peptide concentration required to cause 50% of the haemoglobin leakage relative to cell lysis by 1% TritonX-100. The original data are presented in FIG. 7. For gA-3/4 the highest concentration tested are not enough to cause 50% haemoglobin leakage. And for gA-5 there is no noticeable haemoglobin leakage at 100 μM.
[d] KC$_{50}$ is the peptide concentration required to cause 50% K+ Ion leakage relative to the cell lysis by 1% TritonX-100 (FIG. 8); gA-5 does not cause noticeable K+ ion leakage from the hRBCs at the highest concentration tested 100 μM. nd stands for not determined
[e] gA-5/6 do not show complete inhibition of S. Aureus growth at the concentration range tested, and the IC$_{50}$ for both peptides against S. Aureus are 2.5-5 μM.

Figure 3:
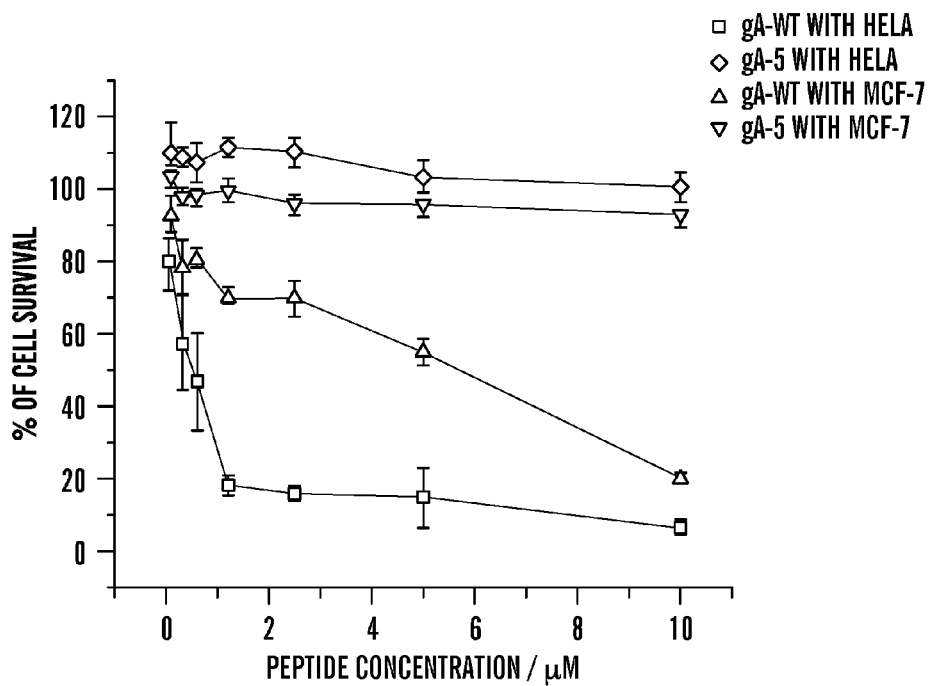
FIG. 3 shows distinct toxicity profiles of gA-WT and gA-5 against two human cancer cell lines (HeLa and MCF-7), demonstrating D-lysine incorporation abolishes gA's toxicity against mammalian cells.

As demonstrated herein, D-lysine incorporation reduces the membrane lytic potency of gA towards hRBCs. The KC$_{50}$ values correlate well with the number of lysine residues incorporated: the single lysine mutants display KC$_{50}$ values higher by ~100 folds that of gA-WT. Again the channel-forming potential appears to be independent of the position of the D-lysine residue. Incorporation of the second D-lysine residue reduces the peptides' potential of K+ leakage by another three orders of magnitude to give KC50 values of ~10 μM. For the triple D-lysine analog peptide gA-5, no K+ leakage is observed even at concentrations as high as 100 μM. Similarly, the peptide-induced hemoglobin release requires gA mutants at higher concentrations as well. While the single D-lysine mutants display hemolytic potency comparable to gA-WT, the double mutants afford significantly higher HC50 values (>70 μM). Again, triple D-lysine gA-5 induces no detectable hemoglobin leakage with the concentrations tested. These results demonstrate that introducing D-lysine residues effectively eliminates gA toxicity towards hRBCs. The toxicity of the gA mutants against two commonly used human cancer cell lines (HeLa and MCF-7) was further examined. Specifically, the percentages of cell survival under varied peptide concentrations through the MTT assay was measured.[17] Similar to the results for hRBCs, gA-WT effectively kills both types of cells with a low μM potency. In sharp contrast, cell growth is essentially unaffected by the triple D-lysine mutant gA-5 (FIG. 3). Comparison of the bacterial and mammalian cell toxicity data reveals a remarkable therapeutic window (at least three orders of magnitude in concentration) for gA-5, which is equivalent to or greater the best amphipathic antimicrobial peptides reported to date.[2b, 15]

Given the high abundance of arginines in natural antimicrobial peptides, the gA analog peptide (gA-6) that incorporates three D-Arg residues instead of the three D-Lys in gA-5 was also prepared and evaluated. While gA-6 keeps low μM potency against bacterial cells, it displays hemolytic activity with an HC50 value of 20 μM, which compares less favorably gA analog peptides with two or three D-Lys residues. The higher hemolytic activity is presumably, without wishing to be bound or limited by theory, because arginine, in comparison to lysine, better facilitates the peptide to partition into mammalian cell membranes.[18]

Figure 4A:
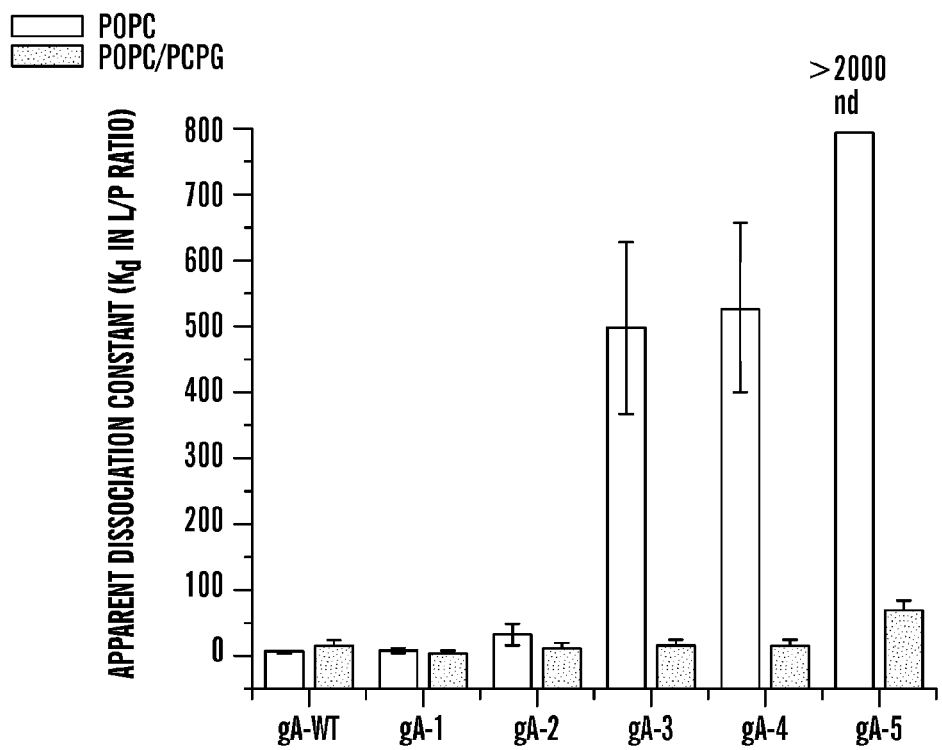
FIGS. 4A-4B show biophysical studies of the gA variants with large unilamellar vesicles as model membranes.
Figure 4B:
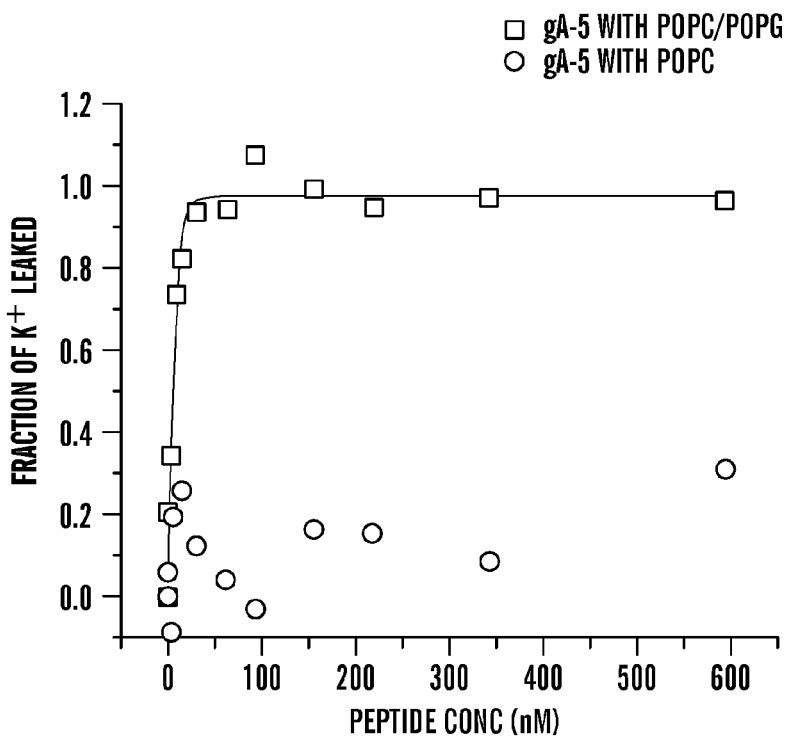

To further understand the microbial selectivity of the D-Lys mutants, binding affinities of the gA analogs peptides to membranes of different compositions were measured. Large unilamellar vesicles (LUVs, ~100 nm in diameter) made of POPC were used as a mimic of hRBCs, while vesicles composed of POPC/POPG (1:1) were prepared to represent bacterial membranes. The peptide-vesicle association was evaluated via a titration experiment, in which LUVs were titrated into peptide solutions and the spectral shift of Trp fluorescence was recorded. Fitting the titration curves yielded the apparent dissociation constants (K$_d$) that are presented in lipid/peptide ratios (FIG. 4A). The single D-Lys mutants gA-1 and gA-2 display no discrimination against neutral and negative membranes, yielding apparent Kd values close to that of gA-WT. In contrast, the double D-Lys variants gA-3 and gA-4 exhibit a much reduced affinity (by ~70 folds) to POPC vesicles, while their affinity to POPC/POPG vesicles remains comparable to that of gA-WT. Under the same experimental conditions, the triple D-Lys analog peptide gA-5 shows no detectable binding to neutral POPC vesicles, while its Kd value toward the negatively charged membrane dropped by a marginal four fold. The preferential association of gA-3, gA-4, and gA-5 with negatively charged membranes presumably accounts, without wishing to be bound or limited by theory, for their bacteria-selective membrane activity. This is further supported by the lack of K+ leakage when the negatively charged liposomes were treated with gA-5, which contrasts sharply to the neutral vesicles (FIG. 4B).

Figure 10:
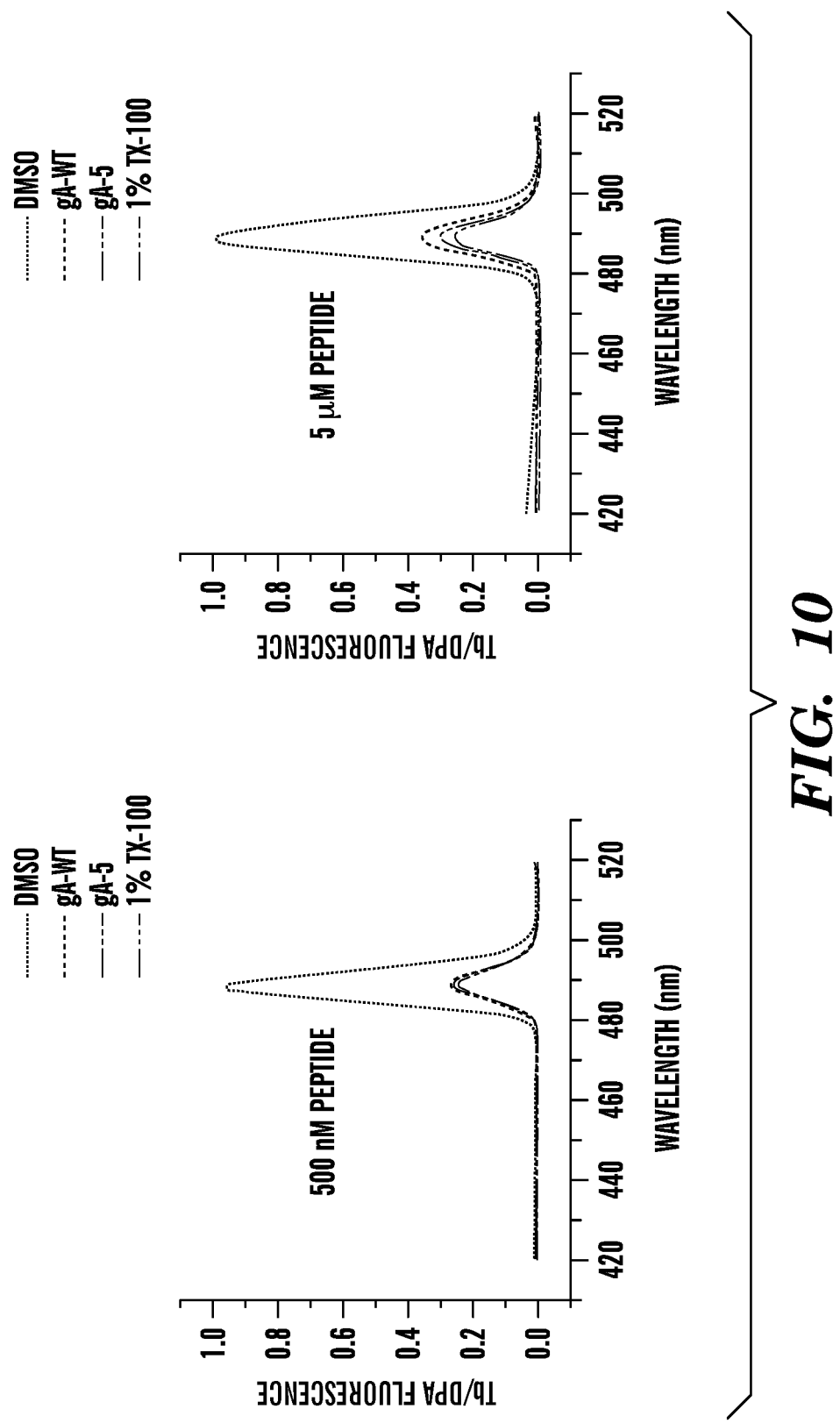
FIG. 10 shows representative luminescence spectra from the $Tb^{3+}$ leakage assay. There is little to no difference in the spectra of gA-WT, gA-5 and DMSO addition, yet both peptides cause complete $K^+$ leakage at these concentrations. The peptides gA-3 and gA-4 behave similarly to gA-5.
Figure 11A:
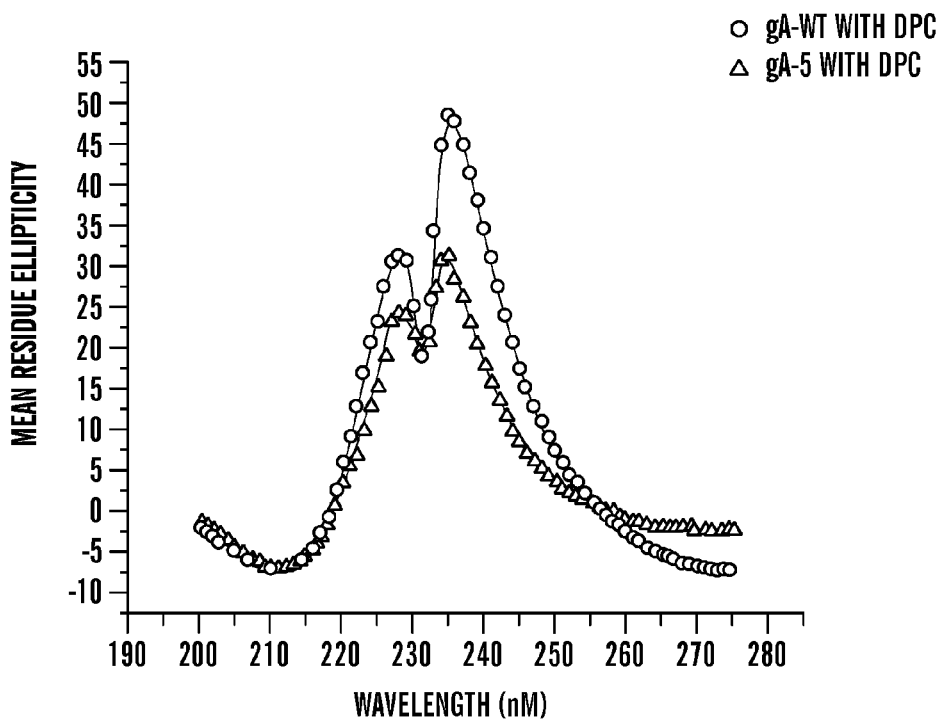
FIGS. 11A-11B show CD spectra of gA-WT and gA-5 in DPC (FIG. 11A) or SDS micelles (FIG. 11B) at 1:50 gA:lipids ratio. (The spectra shown are the averaged signal of three scans after subtracting the DPC or SDS micelle signal).
Figure 11B:
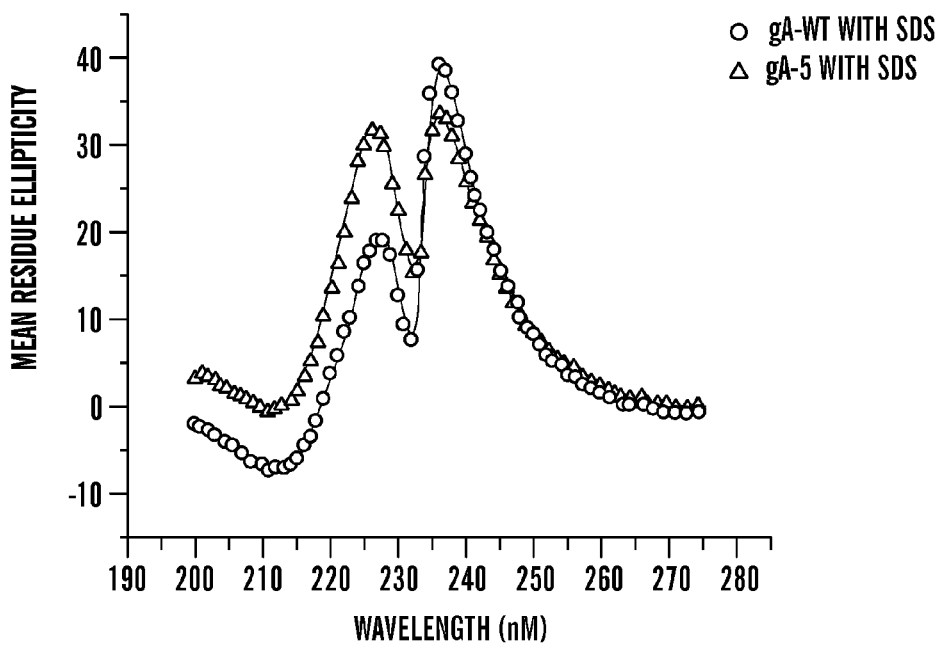
Figure 12:
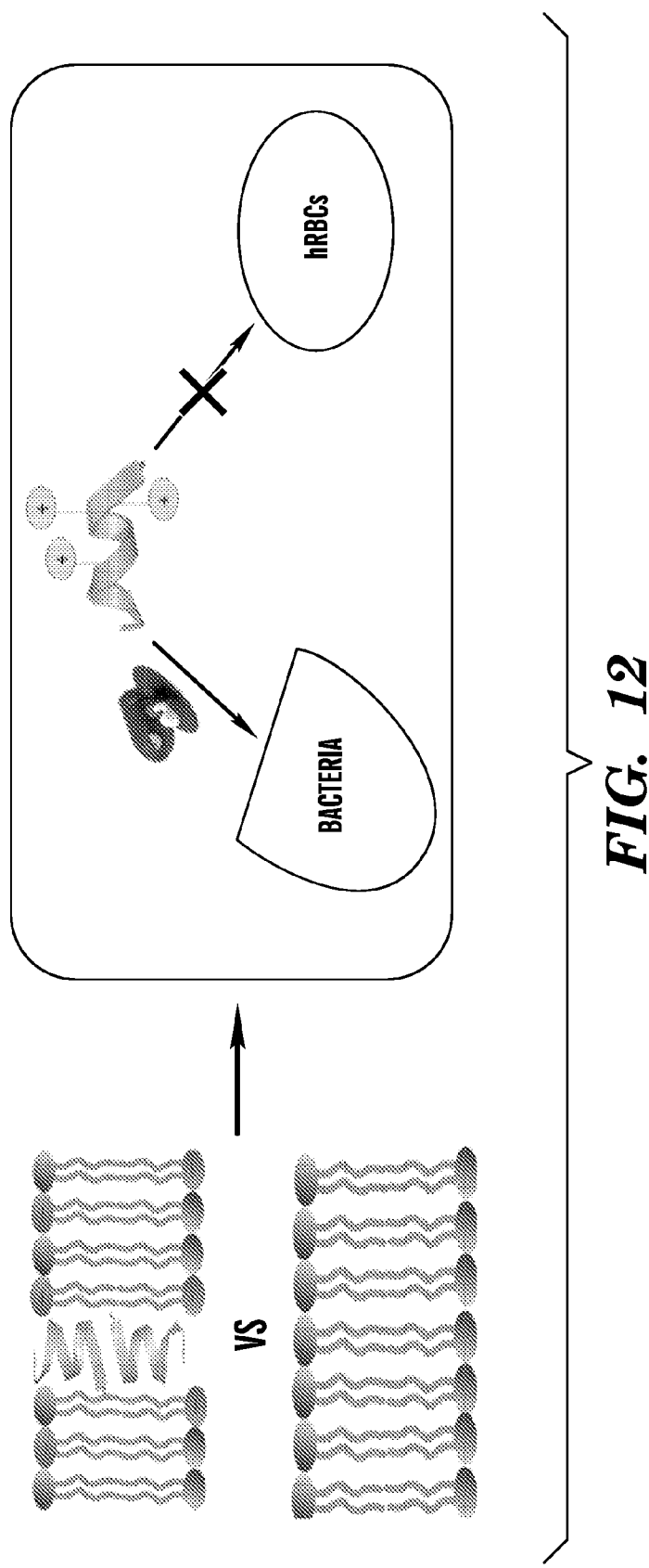
FIG. 12 depicts makeover of an antibiotic, as described herein. A channel forming toxin gramicidin A (gA) is successfully converted into agents that selectively chase after bacterial cells. These novel gA mutants, with D-Lys residues incorporated, display potent antimicrobial activity and remarkable therapeutic indices of >1000 folds.

With the D-Lys residues incorporated towards the C-terminus, the gA peptide analogs described herein display amphipathic sequences. Since many amphipathic peptides are known to cause membrane damage through a detergentlike mechanism instead of forming specific channels,[19] it was further examined whether it is the case with the gA peptide analogs provided herein. Toward this end, the ion selectivity of gA-3, 4, and 5 was assessed by using liposomes encapsulating K+ and Tb3+ respectively. All three peptides showed potent activity in K+ release, yet essentially no Tb3+ leakage was observed at the peptide concentrations that cause complete K+ release from the LUVs (FIG. 10). The selective transport of K+ ions indicates that these gA peptide analogs fold into wild type-like structures, which selectively transport monovalent cations and result in bacteria cell death. The wild type like channel structure of the D-Lys mutants is further supported by the fact that gA-5 and gA-WT share similar signatures in their circular dichroism spectra (FIG. 11). This exclusive leakage of monovalent cations presents a great advantage of the gA analog peptides described herein in comparison to the majority of AMPs, which often cause catastrophic membrane collapse to release all bacterial cellular content, leading to potential complications of over-stimulated immune response.

In summary, demonstrated herein is successful conversion of nonselective channel-forming toxin gA to bacteria-specific ion channels. The gA peptide analogs described herein are highly potent against gram-positive bacteria, yet nontoxic toward at least three mammalian cell lines. The design strategy described herein introduces cationic residues into the gA sequence in order to target the negatively charged membranes of bacteria. The charged residues are strategically placed towards the C-terminus of gA, where they appear to be easily accommodated without compromising gA channel formation. The gA peptide analogs reported here are novel because they form well-defined channels only permeable to water and monovalent cations, while the big family of known amphipathic AMPs cause nonspecific membrane damage, the mechanism of which remains largely unknown. The well defined mechanism of action, in addition to the remarkable bacteria-selectivity, makes the gA peptide analogs described herein highly valuable for use as systemic antibiotics.

Methods

Fmoc-Trp-Wang resin and all Fmoc-protected amino acids were purchased from either Advanced Chemtech (Louisville, KL) or Chem Impex Int. Inc (Wood Dale, Ill.). Unprotected valine and other chemicals were obtained from Sigma-Aldrich unless otherwise indicated. 1-palmitoyl-2-oleoyl-sn¬glycero-3-phosphocholine (POPC) and 1-palmitoyl-2-oleoyl-sn-glycero-3-phospho-(1'-rac-glycerol) sodium salt (POPG) were purchased from Avanti Polar Lipids (Alabaster, Ala.). Peptide synthesis was carried out on a Tribute peptide synthesizer (Protein Technologies, Tucson, Ariz.). PBS buffer, DMEM/High glucose media, Pen/Strep were purchased from Thermo Scientific (Amarillo, Tex.). Fatty acid-free bovine serum albumin (BSA), 0.25% Trypsin-EDTA solution, MTT cell proliferation Assay Kit were purchased from Invitrogen (Carlsbad, Calif.). $^1$HNMR data were collected on a VARIAN GEMINI 500 MHz NMR spectrometer. LC/MS (ESI+) data were generated by the Boston College Mass-Spectrometry facility. The protein concentration of all samples used in this study was determined by measuring their absorbance at 280 nm ($\epsilon$=22760 M−1·cm−1 total of four tryptophan residues) on a NANODROP 2000c UV/Vis spectrometer. The liposomes were prepared by using LIPOSOFAST Mini Extrusion system (Avanti Polar Lipids, Alabaster, Ala.). All three gram-positive negative bacteria (*B. subtilis* (ATCC 663), *S. aureus* (ATCC 6538) and *S. pyogenes* (ATCC 19615)) used in antibiotic activity tests were purchased from Microbiologics (Cloud, Minn.) as lyophilized cell pellet. *E. coli* (BL21) was a gift from the lab of Professor Mary. F. Roberts at Boston College.

Peptide Synthesis and Characterization

1. Synthesis of Formyl-L-Valine [1]

Acetic anhydride (4 mL, 0.04 mol) was added dropwise to a solution of L-Valine (1 g, 8.35 mmol) in formic acid (12 mL, 0.32 mol) while stirring on ice. The mixture was then warmed up to RT and kept stirring for 24 hours before the solvent was removed by rotary evaporation under high vacuum. The formyl-valine was recrystallized from ethyl acetate and the desired product was obtained as a white solid. Yield: 0.78 g (64%) 1HNMR (500 MHz, [D6]Acetone, 25° C., TMS): $\delta$=8.22 (s, 1H), 7.41 (b, 1H), 4.50 (m, 1H), 2.22 (m, 1H), 0.98 (m, 6H).

2. Peptide Synthesis

All peptides were synthesized on Fmoc-Trp-Wang resin (64 mg, 0.79 mmol/g, 0.05 mmol) using standard Fmoc/tBu chemistry. Five equivalents of each amino acid were used for the coupling reaction. The peptides were cleaved off the resin by treating the resin with eolamine (40% (v/v) in degassed DMF, 55° C., 5 hours).[1] Then the resin was filtered through a medium fritted plastic funnel and rinsed three times with DCM and meol to release the peptide completely into solvent. The filtrate containing peptide was dried by rotary evaporation to a minimal volume. Then six to seven times in volume of water was added to precipitate the peptide and the precipitation was separated out by centrifugation (14,000 rpm, 1 hr) and the pellet was dried on lyophilizer to receive the side-chain protected peptide. The Boc protecting group on d-lysine was removed by treating the pellet with a mixture of 95% TFA, 2.5% TIS and 2.5% H2O at RT for 2 hours. The Pbf protecting group on arginine was removed by reagent K (80% TFA, 5% H2O, 2.5% EDT, 5% Thioanisole and 7.5% Phenol, 2 hours at RT). Once the reaction is finished, cold diethyl ether was added to give the crude peptide as white precipitate. The precipitate was again pelleted by centrifugation. The crude material was purified by RP-HPLC (Waters Prep LC, Jupiter 10 jtm C4 300A Column). The identity and purity of each peptide was confirmed by analytical RP¬ HPLC-MS (ESI+) (Waters e2695, Phenomenex, Jupiter 5 jtm C4 300R). All peptides were confirmed to have purity of 95% or higher.

TABLE 3

MS characterization of gA analog peptides

| Peptides | m/z calculated | m/z found |
| --- | --- | --- |
| gA-1 | 1899[M]$^+$ | 949.8/950.2 [M + 2H]$^{2+}$ |
| gA-2 | 1899 [M]$^+$ | 1900 [M + H]$^+$, 948.8/950.2[M + 2H]$^{2+}$ |
| gA-3 | 1913 [M]$^+$ | 957.3/957.8 [M + 2H]$^{2+}$ |
| gA-4 | 1913 [M]$^+$ | 957.8/958.3 [M + 2H]$^{2+}$ |
| gA-5 | 1927 [M]$^+$ | 964.7 [M + 2H]$^{2+}$ |
| gA-6 | 201 2[M]$^+$ | 671.4/671.8/672.1 [M + 3H]$^{3+}$, 1006.9/1007.4/1007.9 [M + 2H]$_{2+}$ |

Peptide Solubility Test

Peptide solubility in 10 mM HEPES buffer with 1% DMSO was measured by monitoring tryptophan absorbance. A concentrated (6.0-8.0 mM) peptide stock solution in DMSO was diluted 100 times (5 μL of the stock into 500 jtl of 10 mM HEPES buffer, pH 7.0). The mixture was sonicated for 30 mins and then subject to centrifugation (14,000 rpm, 10 mins) to remove possible precipitate. The supernatant (400 μL) was transferred to a quartz cuvette and the peptide concentration was determined by tryptophan absorbance at 280 nm ($\epsilon$=22760 M−1 cm-1). The UV/Vis spectra of the supernatant can be seen in FIG. 1 and FIG. 5.

Antimicrobial Activity
1. Minimal Inhibitory Concentration Measurements

Figure 6A:
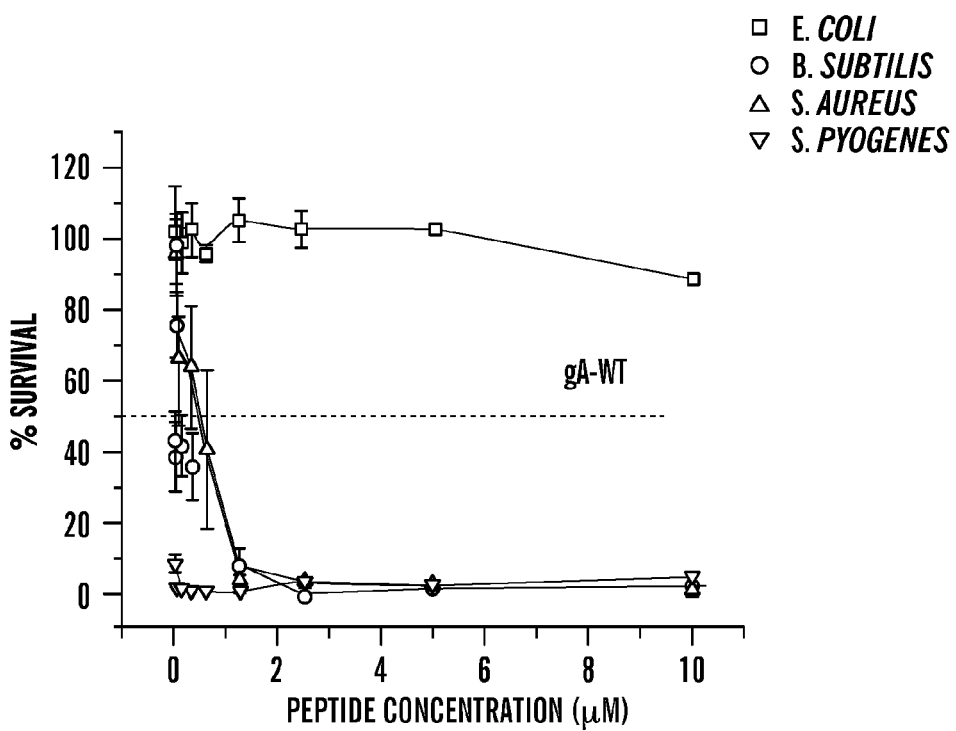
FIGS. 6A-6B show antibiotic activity of gA-WT (FIG. 6A) and gA-5 (FIG. 6B) against the bacteria strains tested
Figure 6B:
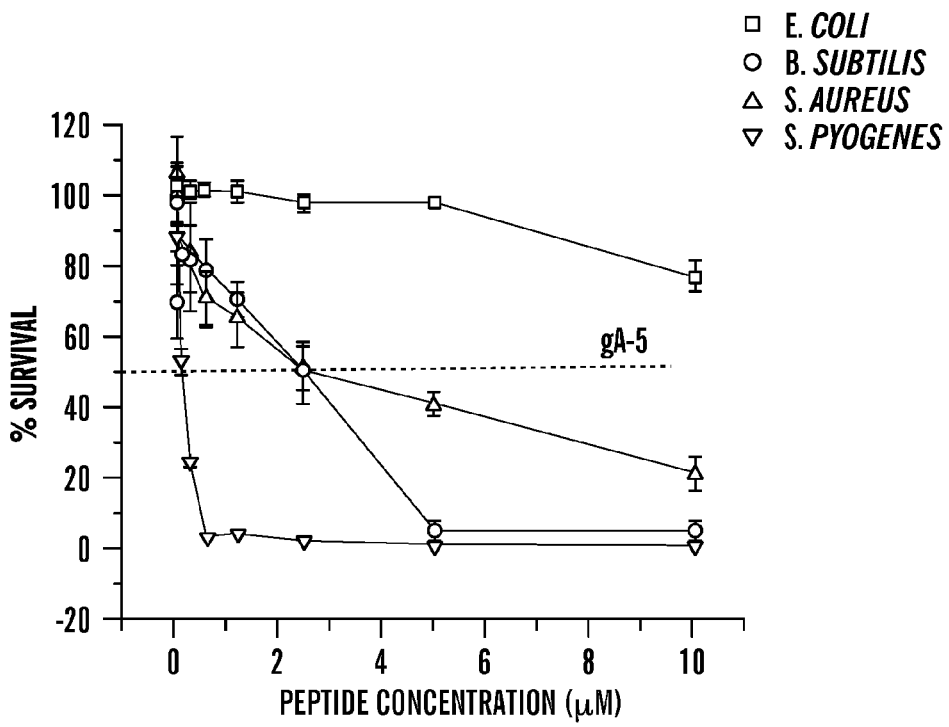

Minimal Inhibitory Concentrations (MICs) were measured against Gram-negative *Escherichia coli* (BL21) and Gram-positive *Bacillus subtilis* (ATCC 663), *Staphylococcus aureus* (ATCC 6538), *Streptococcus pyogenes* (ATCC 19615) using the broth microdilution method.[2] Specifically, bacteria from a single colony were grown overnight in LB broth at 37° C. with agitation. An aliquot was taken and diluted (1:50 for *E. coli*, 1:20 for *B. subtilis*, 1:200 for *S. aureus*, 1:10 for *S. pyogenes*) in fresh broth and cultured for another ~3 hours until the cells reach mid-logarithmic phase (OD590-0.6). The cells were diluted to a concentration of ~5×10$^5$ Colony Forming Units/ml (CFU/ml) and the bacteria suspension (200 µL) was added to each well of a sterile 96-well plate. Serial diluted (2-fold) peptides in DMSO (2 µL) were added in triplicates. The plates were shaken for 30 seconds to mix the peptide solution well with the broth, and then incubated at 37° C. overnight before the absorbance at 590 nm was monitored using a microtiter plate reader (SPECTRAMAX M5, Molecular Devices, Sunnyvale, Calif.). The viability of the bacteria was normalized as % survival= ($OD_{pep,bac}$−$OD_{broth}$ only)/(ODDMSO, bac-ODbroth only)× 100%. The effect of 1% DMSO is negligible as the bacterial cell density with DMSO addition is comparable with that of bacterial suspension in LB Broth. The MIC was recorded as the peptide concentration required for complete inhibition of cell growth (no change in absorbance). Representative curves plotting the cell viability against the peptide concentration are shown in FIGS. 6A-6B.

Toxicity Against Mammalian Cells
1. Haemoglobin Release from Human Red Blood Cells[3]

Fresh human red blood cells (hRBCs) were centrifuged at 3500 rpm and washed with PBS buffer until the supernatant was clear. The hRBCs were then resuspended and diluted to a final concentration of 1% (v/v) in PBS and used immediately. 15 µL of serial dilution (2-fold) of peptides in DMSO or DMSO alone as a negative control were added to 1.5 mL of hRBCs in PBS. The resulting mixture was gently shaken to mix well and incubated at 37° C. for 1 hr, followed by centrifugation at 3500 rpm for 10 min using tabletop centrifuge. Aliquots (50 µL) of the supernatant (in triplicates) were transferred into a sterile 96-well plate containing 50 µL of H$_2$O in each well. Release of hemoglobin was monitored at 415 nm using a microtiter plate reader. Percentage hemolysis was calculated using percentage hemolysis=100·(A415, peptide-A415,DMSO)/(A415, complete hemolysis-A415, DMSO), where complete hemolysis is achieved by mixing hRBCs with 1% TritonX-100. The peptide concentration required to cause 50% hemoglobin leakage was read out from the graph and listed in Table 2 as $HC_{50}$.

2. K+ Leakage from hRBCs[4]

The rest of supernatant (1.2 mL) from each sample prepared as described in the hemoglobin leakage assay was transferred into a new sterile eppendorf tube and subject to the K+ concentration measurement using a flame-atomic emission spectrometer ($\lambda_{em}$=766.5 nm, Perkin Elmer Atomic absorption Spectrometer 3100, acetylene/air flame). Three readings were taken for each sample and averaged as final results. The fraction of K+ leakage from hRBCs was calculated as percentage K+ leaked=100·($I_{776.5,peptide}$−$I_{776.5,DMSO}$)/($I_{776.5,complete\ lysis}$−$I_{776.5,DMSO}$). The peptide concentration required to cause 50% K+ leakage was read out from the graph (FIG. 8) and listed in Table 2 as $KC_{50}$.

3. Toxicity Against Human Cell Lines

Toxicity of gA-WT and gA-5 was tested against two human cancer cell lines, HeLa and MCF-7 (gifts from Professor Eranthie Weerapana at Boston College) by using the MTT assay as described in the protocol provided by Invitrogen.[5] HeLa cells (in DMEM high glucose media with 10% FBS, 1% Pen/Strep, 37° C., 5% CO$_2$) and MCF-7 cells (in RPMI media with 10% FBS and 1% Pen/Strep, 37° C., 5% CO$_2$) were grown to about 80% confluent before removed from the surface of a 20 cm petri-dish with 25% Trypsin with EDTA (3-5 mins, 37° C., 5% CO$_2$). Cells were pelleted (3,500 rpm, 5 mins at 4° C.), and plated at 15,000 cells per well (100 µL per well), then incubated for 48 hrs before peptide addition.

Stock solutions of gA in DMSO with varied concentrations were prepared so that for each peptide concentration the total volume of DMSO addition was kept constant at 1% (v/v). For each peptide concentration, samples were set up as four replicates. Control wells were loaded with 1 µL of DMSO. After overnight incubation, cells were washed once with PBS before being incubated for 4 hrs with 110 µL of 12 mM 3-(4,5-Dimethylthiazol-2-yl)-2,5-diphenyltetrazolium bromide (MTT) dissolved in RPMI media. The MTT assay was quenched with 100 µL of 10% SDS in 0.01 M HCl and allowed to incubate overnight before absorbance at 570 nm was recorded. Wells were averaged and standard deviations determined for each peptide concentration. Data were normalized to the DMSO control to give % cell survival (see FIG. 3).

Model Membrane Studies of gA Channel Activity

Buffer A: 10 mM HEPES, 150 mM NaCl, pH 7.0; Buffer B: 10 mM TES, 150 mM sodium citrate, pH 7.0

1. Liposome Preparation

A chloroform solution containing 76 mg of POPC (for POPC LUVs) or a chloroform/meol (1/1) containing 38 mg of POPC and 38.5 mg POPG sodium salt (for POPC/POPG LUVs, POPC:POPG=1:1) was dried under reduced pressure to form a thin film, which was then hydrolyzed with 2 mL aqueous buffer: (1) 10 mM HEPES, 150 mM KCl, pH 7.0 for K+ leakage assay; (2) 10 mM TES, 100 mM sodium citrate, 50 mM TbCl3, pH 7.0 for Tb3+ leakage assay; (3) 10 mM HEPES, 150 mM NaCl, pH 7.0 for peptide binding assay. After 20 cycles of freezing and thawing, the liposome suspension was extruded 21 times through a 100 nm polycarbonate membrane (LIPOSOFAST Mini Extrusion system, Avanti Polar Lipids; Whatman Nuclepore Track-Etch Membrane) at RT. Free K+ or Tb3+ were removed by gel filtration (ÄKTA FPLC with HiPREP™ 16/60 Sephacryl TM-S-500HR column) using Buffer A for (1) and (3) or Buffer B for (2) as the eluents. The lipid concentration was determined by the Stewart assay [6] and the size of liposome was confirmed by Dynamic Light Scattering (DLS, DYNAPRO NANOSTAR, Wyatt, Santa Barbara, Calif.). After gel filtration the polydispersity of all liposome are below 20%. The total lipids concentration in POPC/POPG LUVs was calculated by doubling the measured POPC concentration, as the Stewart assay does not report the amount of POPG.

2. K+ Leakage Assay

The K+ leakage from liposomes was determined by a potassium ion selective electrode (K-ISE, Cole-Parmer, Vernon Hills, Ill.). The electrode was calibrated each day before experiments. A liposome solution in Buffer A (2 mL, 500 µM POPC or POPC/POPG ⊃ 10 mM HEPES, 150 mM KCl, pH 7.0) was stirred at constant speed and peptide at various concentration (1 µL in DMSO) was added accumulatively. Three minutes after each peptide addition, the K+ concentration was measured and reported as the K-ISE potential. At the end of each experiment, gA-WT stock (1 µL, 1 mM) was added to induce 100% K+ leakage. The potential reported by the K-ISE was plotted against peptide concentration after the background noise (caused by DMSO addition) was subtracted and normalized to 0-100%.

3. Peptide Binding onto Membranes

Figure 9:
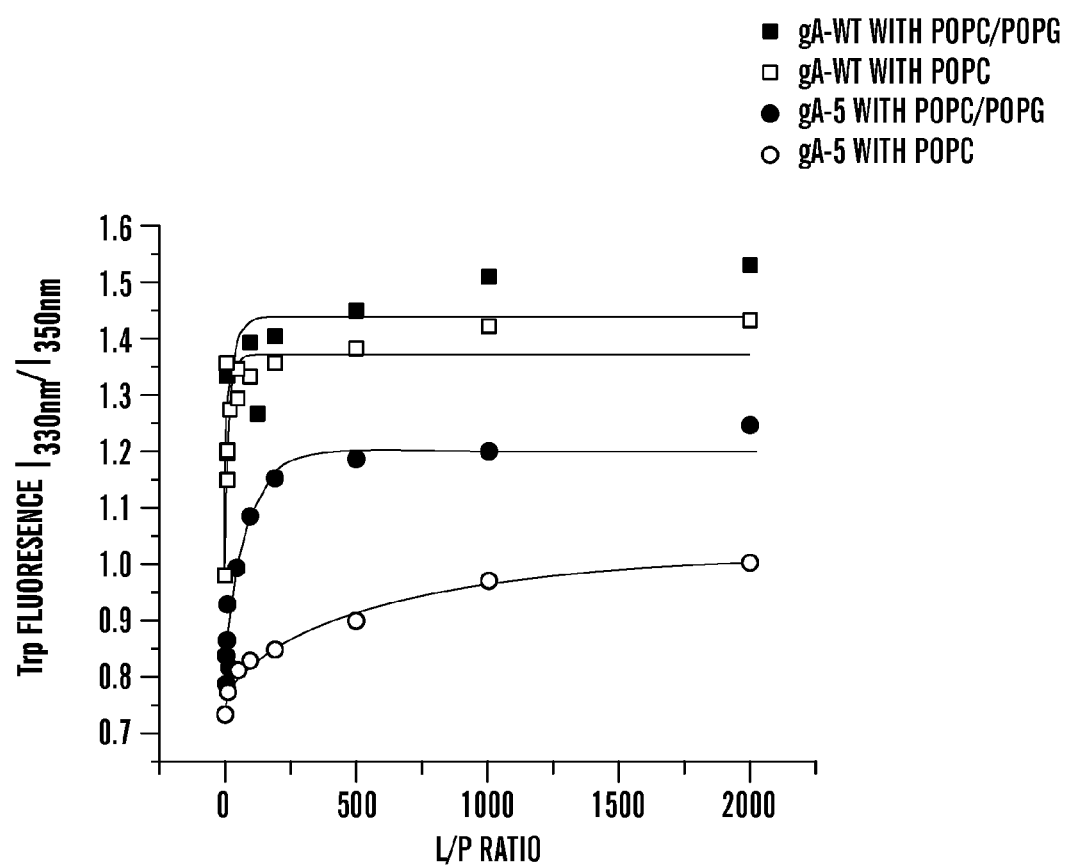
FIG. 9 shows representative binding curves of gA peptides, fitted with exponential function.

Peptide partitioning into lipid bilayers was monitored by fluorescence enhancement of tryptophan upon addition of liposomes. gA mutants (500 nM) was mixed with various amounts of liposome in Buffer A (POPC ⊃ 10 mM HEPES, 150 mM NaCl, pH 7.0 or POPC/POPG ⊃ 10 mM HEPES, 150 mM NaCl, pH 7.0). The mixture was agitated gently for 30 mins before the tryptophan fluorescence spectra were scanned from 320 nm to 360 nm on a SPECTRAMAX M5 spectrometer (Molecular Devices, Sunnyvale, Calif.). For each peptide, the ratio of fluorescence intensity at 330 nm and 350 nm (I330 nm/I350 nm) was calculated and plotted against the Lipid/Peptide ratio (L/P ratio). The curve was fitted into an exponential function to give an apparent binding constant. FIG. 9 shows representative binding curves acquired.

4. Tb3+ Leakage Assay

The leakage of Tb3+ from liposomes was monitored by the luminescence of the Tb/DPA complex[7]. To a mixture of vesicles (500 μM POPC or POPC/POPG ⊃ 10 mM TES, 100 mM sodium citrate, 50 mM TbCl3) and DPA (50 μM) in Buffer B was add the gA peptide at 0.5 μM and 5 μM respectively. The peptide liposome mixture was incubated at RT for 30 mins before the fluorescence intensity of Tb/DPA complex ($\lambda_{ex}$=270 nm, $\lambda_{em}$ 490 nm) was recorded ($I_c$) in a quartz cuvette on a fluorescence spectrometer (Jobin Yvon, Horiba Scientific). The results are shown in FIG. 10. Complete Tb3+ leakage was assessed by TritonX-100 lysis of liposomes ($I_f$). A sample with pure DMSO addition was used as blank ($I_0$) and the fraction of Tb3+ leakage can be calculated as fraction=$(I_c-I_0)/(I_f-I_0)$.

5. Peptide Secondary Structure Characterized by Circular Dichroism (CD) Spectroscopy The gA variants (0.2 μmol) dissolved in DMSO were mixed with Fos-phosphatidylcholine-C12 (DPC, 10 μmol) or sodium dodecyl sulfate (SDS, 10 μmol) in meol (L/P ratio 50). Then the mixture was dried by rotary evaporation and lyophilized overnight to remove all possible solvent. Next, dry gramicidin/DPC or SDS films were resuspended in N2-flushed H$_2$O before the incubation (55° C., 15 mins) and ultrasonication (RT, 1 min) cycles (three times) were performed[8]. The micelles (with peptides) were centrifuged at 12,500 rpm for 5 mins to remove possible aggregation and other residues generated in ultrasonication. The supernatant was transferred into a quartz cuvette and CD spectra were recorded (RT, 1 cm path length, scan 200-275 nm, integration time 3 s) on the AVIV Model 420 Circular Dichroism Spectrometer (Biomedical Inc, Lakewood, N.J., FIG. 11).

Lysine N$^\epsilon$-Trimethylation as Tool to Fine Tune the Solubilized Gramicidin A Activity The rapid development of multidrug resistant pathogenic bacteria poses serious threats to the society and demands new antibiotics function through different mechanisms. Within the past decade, a significant amount of effort has been paid to optimizing naturally occurring antimicrobial peptides (AMPs) and developing their functional analogues as novel antibiotics. AMPs are a large collection of short peptides (12-80 amino acids) that kill a wide spectrum of bacteria and serve as the frontline of the innate immune system. Different from conventional antibiotics, which often target a specific protein involved in biosynthesis, AMPs are believed to work by disrupting the plasma membrane of bacterial cells. This unique mechanism makes it difficult for bacteria to acquire resistance and provides AMPs longer effective shelf-life. However, the development of AMPs into systemic antibiotics has been slow because of their low efficacy, toxicity, and limited tissue distribution. Rational improvement of AMPs has been difficult largely due to lack of detailed understanding about the mechanism and the structure activity relationships. For instance, it remains unclear whether AMPs form permanent pores in membranes; the underlying reasons of bacterial specificity and activity still need further investigation as well.

Figures 13A, 13B:
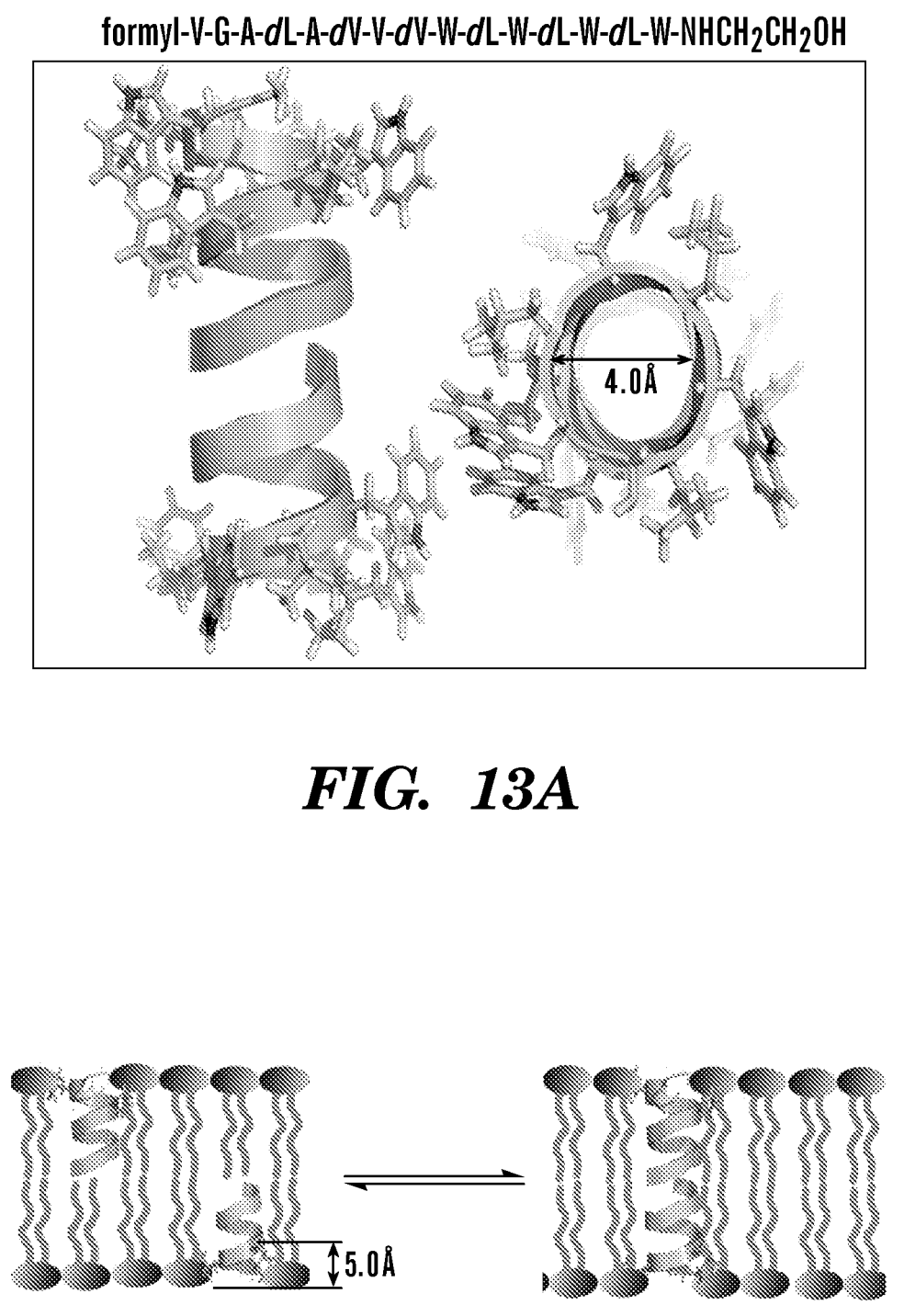

In contrast to the majority of AMPs, a small number of peptides do have clearly defined toxicity mechanisms. A prominent example of such peptides is gramicidin A (gA), a fifteen-residue linear peptide isolated from *Bacillus brevis*. Composed of alternating D- and L-amino acids, gA folds into a β-helix with an internal pore (FIG. 13A). The length of the β-helix matches well with one leaflet of a membrane; inter-leaflet dimerization yields a trans-membrane channel with a diameter of 4 Å (FIG. 13A). The channel allows free diffusion of water and a selection of monovalent cations (e.g. Na$^+$, K$^+$), but it is impermeable to larger species including polyvalent cations. The ion-selective channel activity has made gA a popular model membrane protein and a blueprint for engineering functional channel sensors.

Also due to the channel activity, gA displays potent antibiotic activity. In fact, it is used as one of the active ingredients of the commercialized antibiotic ointment POLYSPORIN in Canada. However, the peptide is essentially insoluble in water (<50 nM) and induces hemolysis under concentrations required to cause bacteria cell death. Consequently, its therapeutic usage has been limited to topical applications.

As described herein, we have demonstrated that incorporating cationic residues like lysine (Lys) significantly increases gA water solubility and decreases mammalian cell toxicity. Furthermore, mutation of all three D-Leu (dL 10, 12, 14 dK) converts the non-selective channel forming toxin gA-WT to having the ability to behave as bacteria-specific systemic antibiotics. The selectivity was proven mainly from the preferentially binding between cationic gA analogous and anionic bacteria membrane over the neutral mammalian cell membrane. Moreover, all Lys containing gA analogous exhibited similar structure and bacteria killing mechanism as that of the gA-WT. The work described herein demonstrates that diffusion of positive charges across a lipid bilayer is highly efficient in the gA system. Structure analysis showed that the protonated amino group can be exposed to the aqueous environment easily as the deepest buried dK 10 in gA is 5 Å away from the boundary of bilayer (Lys side chain length is 5 Å, FIG. 13B). The research described herein on AMPs showed that increasing peptide hydrophobicity boosts the antimicrobial activity. Accordingly, we tested whether increasing peptide hydrophobicity while maintaining the positive charge can selectively increase bacterial cell but not mammalian cell toxicity, as described herein.

Lys N$^\epsilon$-methylation recently received attention for its in vivo role in regulating the transcriptional status of chromatin through the histone proteins. In contrast, little is known about the effect of Lys methylation in the AMP field. It is known that Lys N$^\epsilon$-trimethylation increases hydrophobicity while keeping the same charge as Lys at physiological pH. A simple Spartan calculation showed consistent results. Trimethyl ethylamine is more hydrophobic and has 100 kJ/mol lower desolvation energy (Table 4). Therefore, Lysine N$^\epsilon$-trimethylation could achieve the two goals simultaneously. Herein we report the effect of Lys N$^\epsilon$-trimethylation on gramicidin A.

showed less antimicrobial activity compared to the Lys version. Despite that Lys trimethylation increased the peptides hydrophobicity, decreased their water solubility, it failed to boost the antibacterial activity—in particular, the 10, 12, 14 MeK and 10, 12 MeK analogs lost their antibacterial activity against all four bacteria strains in the concentration range we tested (Table 6).

TABLE 6

Antibacterial activity and preliminary toxicity on human red blood cells (hRBCs) of gA analogous containing N$^\epsilon$-trimethylated Lys

| Peptide | Minimum Inhibition Concentration/μM | | | Toxicity/μM | |
| --- | --- | --- | --- | --- | --- |
| | B. Subtilius | S. Aureus | S. Pyogenesis | HC$_{50}$ | KC$_{50}$ |
| gA-WT | 2.5 | 2.5 | 0.16 | 5 | 1.40E−04 |
| 10M | 2.5 | 2.5 | 0.15 | 19 | 0.04 |
| 14M | 2.5 | 1.25-2.5 | 0.078 | 24 | 0.015 |
| 10, 14M | 2.5 | >10 (HC$_{50}$ = 1.25) | 1.25 | >24 | 20 |
| 10, 12M | na | na | >10 (EC$_{50}$ = 1.25) | >10 | >10 |
| 10, 12, 14M | na | na | na | >95 | >95 |

[a] The minimum inhibition concentration is determined by the standard micro-dilution methods, all tests were repeated at least three times to confirm the reproducibility. None of the peptides tested was active against the gram-negative E. Coli.
[b] na (not active) as no noticeable bacteria growth inhibition were observed in the concentration tested.
[c] HC$_{50}$ is the peptide concentration required to cause 50% of haemoglobin leakage from human red blood cells compared to the lysis of same amount cells by 1% TritonX-100. No haemoglogin leakage was observed in the cases of 10, 14M, 10, 12M or 10, 12, 14M at the concentration range tested.
[d] KC$_{50}$ is the peptide concentration required to cause 50% K$^+$ ion leakage from human red blood cells relative to the cell lysis by TritonX-100.

TABLE 4

Calculated solvation energy

| Molecules | The solvation energy (kJ/mol) |
| --- | --- |
| Ethylamine (neutral) | −18.66 |
| Trimethylethylamine (single cation) | −202.09 |

We synthesized a series of gA mutants with N$^\epsilon$-trimethylated lysine. Consistent with increased hydrophobicity, compared to the original version gA analogous with N$^\epsilon$-trimethylated Lys showed slightly decreased solubility (Table 5).

TABLE 5

Nomenclature and solubility comparison of gA analogs comprising Lys or N$^\epsilon$-trimethylated Lys

| Lys series[a] | Sat. Conc/ μM[b] | N$^\epsilon$-trimethylated Lys series | Sat. Conc/ μM |
| --- | --- | --- | --- |
| 10K | 10 | 10M | 4.3 |
| 14K | 11 | 14M | 3.6 |
| 10, 14K | 38 | 10, 14M | 30 |
| 10, 12K | 39 | 10, 12M | 27 |
| 10, 12, 14K | 72 | 10, 12, 14M | 55 |

Figure 14A:
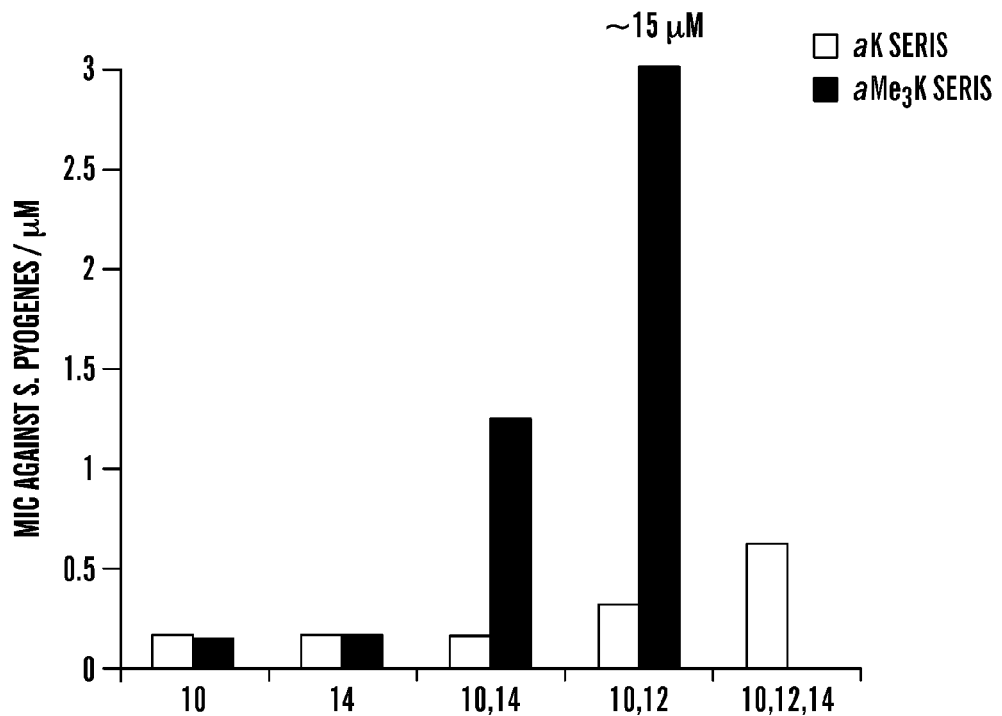
FIG. 14A shows antibacterial activity comparisons of gA analogs comprising Lys and $N^\epsilon$-trimethylated Lys modification; the 10, 12, 14M peptide analog lost antibacterial activity completely, therefore, no bar is shown.
Figure 14B:
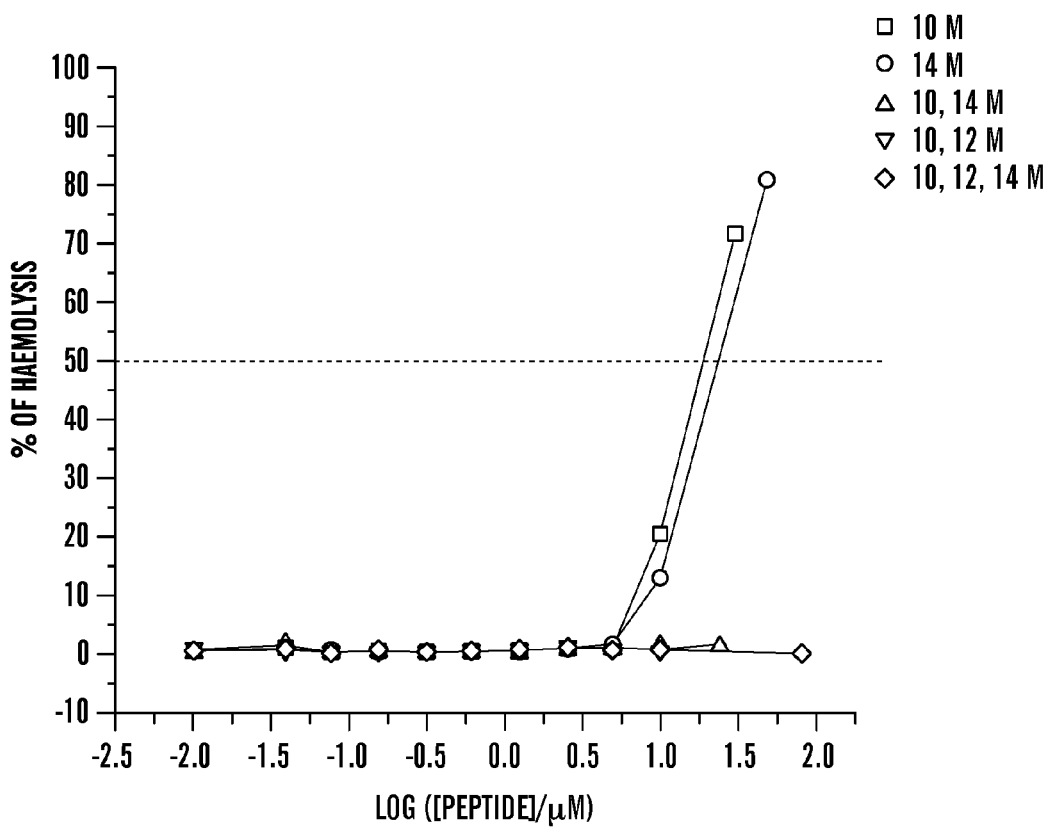
FIG. 14B shows haemoglobin leakage with gA analogs comprising $N^\epsilon$-trimethylated Lys. The therapeutic indices were calculated as $HC_{50}$/MIC in which the MIC and $HC_{50}$ values were acquired from graphs above.

[a]the number in the label refers to the position of modified amino acid(s)
[b]solubility was determined by measuring the tryptophan absorbance @ 280 nm. All peptides were dissolved in 10 mM PBS, pH 7.0 containing 1% DMSO, and centrifuged at 14,000 rpm for 20 mins before the supernatant were taken for UV-Vis measurement. Values for Lys series were taken from ref Then the antibacterial activities of these gA analogs were tested against four different bacteria strains and the results were compared to the relative Lys containing peptides. The bacteria strains tested include the gram-negative E. coli (BL 21), and gram-positives B. subtilis (ATCC 663), S. aureus (ATCC 6538) and S. pyogenes (ATCC 19615). The minimum inhibitory concentration (MIC) was determined by the standard microdilution procedure. Surprisingly, all analogs Then, the preliminary toxicities were evaluated on human red blood cells (hRBCs) through two complementary assays. The typical haemolytic assay monitors leakage of haemoglobin as a consequence of the peptide-induced membrane damage. In addition, considering functional mechanism of gA, we specifically evaluated the peptide-induced K+ leakage from the hRBCs under identical condition of haemolytic assay by using atomic emission spectroscopy, in which K+ concentration can be assessed by its characteristic emission at 766.5 nm. Fortunately, the toxicities of these peptides decreased even more compared to the loss in antibiotic efficacy (FIGS. 14A-14B). The peptides containing more than one N$^\epsilon$-trimethylated Lys lost their toxicity against hRBCs completely. We were able quantify activities and the toxicities of the two peptides containing single residue modification and a moderate gain (2-5 folds, Table 7) in therapeutic index were observed. As for the nontoxic gA analogous, no HC50 value is available to quantify the therapeutic indexes. In general, Lys N$^\epsilon$-trimethylation decreases membrane activities of gA analogous in a membrane dependent manner.

TABLE 7

Folds of therapeutic indices increases by Lys N$^\epsilon$-trimethylation

| | B. Subtilius | S. Aureus | S. Pyogenes |
| --- | --- | --- | --- |
| 10M vs 10K | 5 | 2 | 3 |
| 14M vs 14K | 3 | 3 | 4 |

[a] therapeutic index was calculated as HC$_{50}$/MIC, and the folds were round to integral

TABLE 8

Activities of Methylated Lysine series gA analogs on cells

| | Gram-negative | Gram-positive | | | | |
|---|---|---|---|---|---|---|
| | E. coli | B. Subtillus | S. Aureus | S. Pyogenesis | HC50 | KC50 |
| gA-WT | na | 2.5 | 2.5 | 0.16 | 5 | 1.40E–04 |
| 10MeK | na | 2.5 | 2.5 | 0.15 | 19 | 0.04 |
| 12MeK | nd | 5 | 2.5 | 0.16 | >10 | 0.2 |
| 14MeK | na | 2.5 | 1.25-2.5 | 0.078 | 24 | 0.015 |
| 1014MeK | na | 2.5(mgjump from 1.25) | >10 (HC$_{50}$ = 1.25) | 1.25 | >24 | 20 |
| 1012MeK | na | na | na | >10 (EC$_{50}$ = 1.25) | >10 | >10 |
| 1214MeK | nd | 5 | >10 | 2.5 | | >10 |
| Tri-MeK | na | na | na | na | >95 | >95 |

Figure 15:
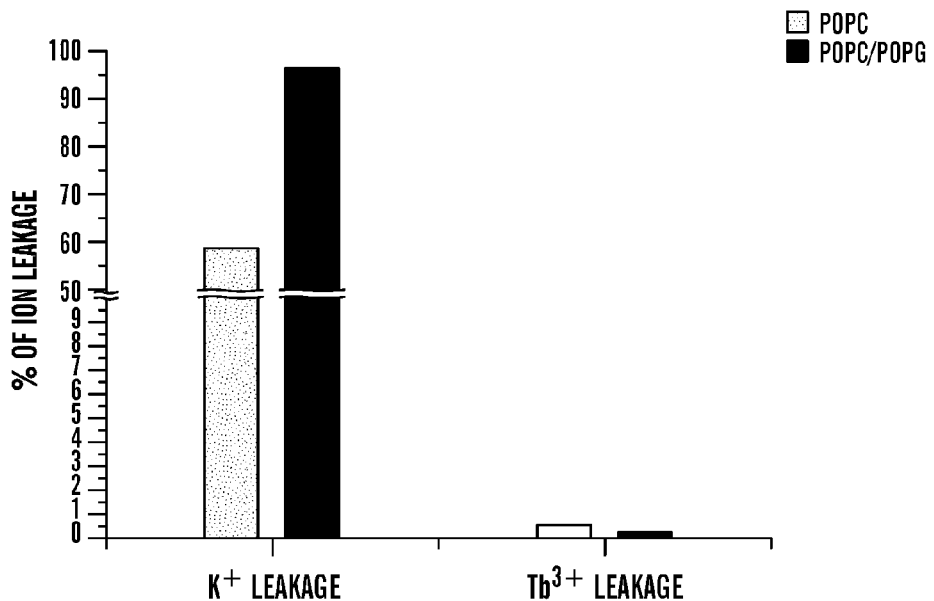
FIG. 15 shows ion leakage propensities induced by the 10, 14M gA analog as an example. Data were normalized against 500 nM WT-gA (100% K+ leakage) and 0.1% TX-100 (100% Tb3+ leakage) lysed vesicles and DMSO treated vesicles (0% leakage).
Figure 16:
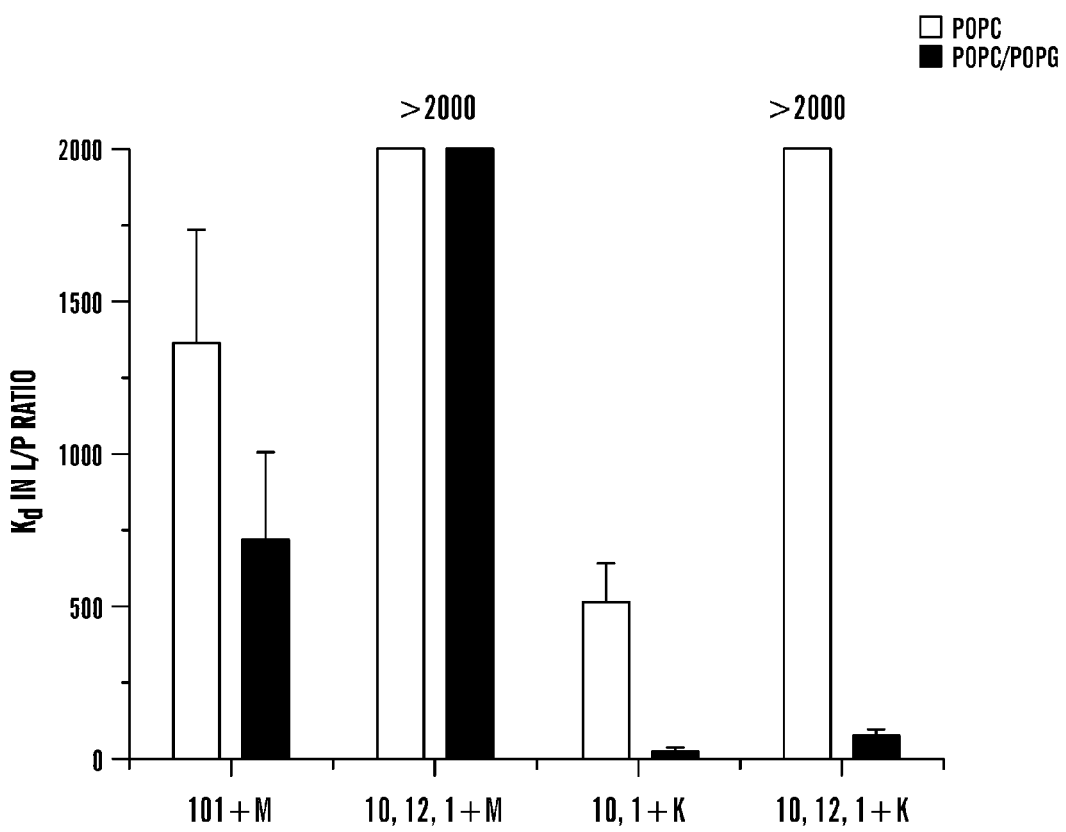
FIG. 16 shows a comparison of apparent dissociation constants of peptides and liposomes binding before and after peptides Lys methylation. The Trp fluorescence signal (I330/350 nm) were plotted against L/P ratio, and each set of data were fitted into exponential function to calculate the apparent dissociation constant (Kd), The graph shows two sets of peptides as examples.

To better understand our observation that the more hydrophobic versions of the gA analogs showed less membrane activity, a series of mechanistic studies on model liposomes were carried out. Two kinds of liposomes were used in all characterization. Large unilamellar vesicles (LUVs, ~100 nm in diameter) made of POPC were used as a mimic of hRBCs, while vesicles composed of POPC/POPG (1:1) were prepared to represent bacterial membranes. Firstly, the functional mechanism of gA analogous on vesicles was confirmed by two sets of leakage assay comparatively. As shown in FIGS. 13A-13B, gA forms well defined channel structure in the lipid bilayer which only allows small monovalent cation ($K^+$) to pass through but not big ions ($Tb^{3+}$). We measured and compared the leakage propensity of the two ions from LUVs (FIG. 15, Table 9). As expected, $K^+$ ion readily leaked out from vesicles at peptide concentration of 100 nM, while less than 1% of $Tb^{3+}$ leakage was observed at a much higher concentration (500 nM). It indicated that, similar to that of gA-WT, all gA analogs functioned as a well-defined channel. Consistent with the selectivity observed in the cell based experiments, the peptides induce ion leakage more readily on the negatively charged vesicles than on the neutral ones.

TABLE 9

Comparison of ion leakage (K+ vs Tb3+) at specified peptide concentration form LUVs

| | $K^+$ from POPC/POPG (95 nM) | $K^+$ from POPC (95 nM) | $Tb^{3+}$ 500 nM P with POPC | $Tb^{3+}$ 500 nM P with POPC/POPG |
|---|---|---|---|---|
| WT | 96 | 70 | 4.5 | 3.4 |
| 10MeK | 93 | 66 | 0.8 | 1.0 |
| 14MeK | 95 | 86 | 1.2 | 1.8 |
| 1012MeK | 90 | 73 | 2.2 | 3.6 |
| 1014MeK | 97 | 59 | 0.5 | 0.2 |
| triMeK | 30 | –2.7 | –1.5 | –1.5 |

Figure 20:
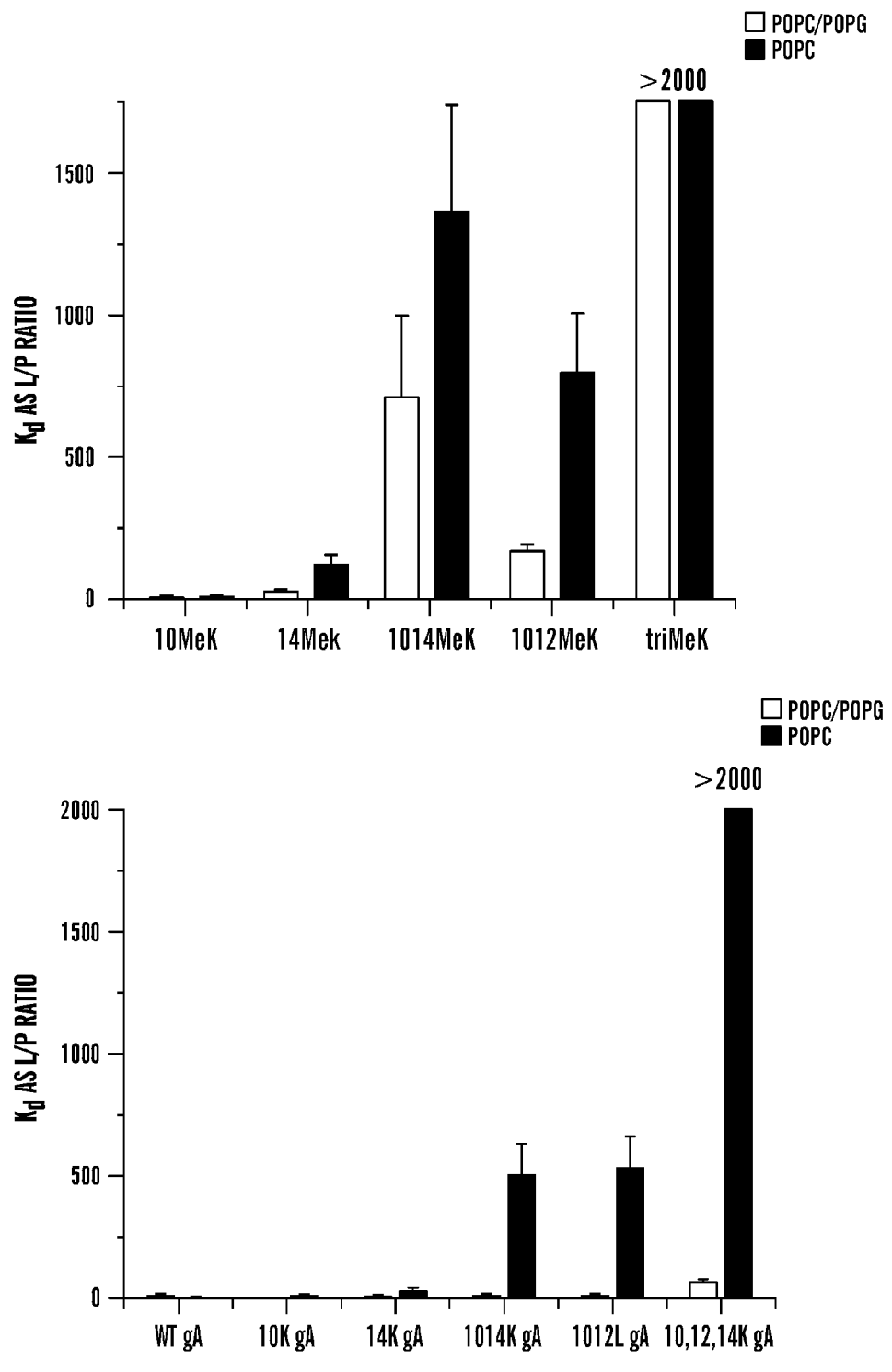
FIG. 20 demonstrates dissociation constant of $N^\epsilon$-trimethylated Lys containing gA mutants determined by Trp fluorescence. Methylation of lysine decreases peptide binding affinity with both POPC and PCPG LUVs. As more was decreased for PCPG LUVs, the binding selectivity decreases.

Then, the binding affinity of the peptides to liposomes was determined by monitoring the tryptophan fluorescence. It is well known that tryptophan fluorescence emission blue shifts ($\lambda_{em}$, max 350 nm to 330 nm) and the intensity increases upon binding to vesicles. By plotting the fluorescence intensity ($I_{330}/I_{350\ nm}$) against the lipids/peptides ratios (L/P ratio), we were able to compare the dissociation constants of all peptides. 10, 12, 14 M gA showed no binding to either of the vesicles, which might account for the loss of cell activities. gA analogs comprising single or double residues modification(s) bound to the negative charged vesicles preferentially due to the attractive electron-static interactions. Surprisingly, all peptide analogous exhibited increased dissociation constant on both negatively charged liposome (POPC/POPG) and neutral liposomes (POPC only) compared to the original Lys versions (FIG. 4 and FIG. 20). As methylation of lysine residues does not change the number of charges carried by a peptide, the differences in binding affinity indicated that the peptide liposome binding is not only driven by the electrostatic attractions but also other factors. Hydrogen bonding between lysine side-chain and head-group of phospholipids can stabilize the bound form. Replacements of hydrogen by methyl remove the H-bond ability from the system, consequently, destabilized the bound form and shifted the equilibrium. And this shift of peptides distribution in a liposomal solution can be responsible for the decrease in membrane activity as less peptide ended up on the membrane.

Figure 17A:
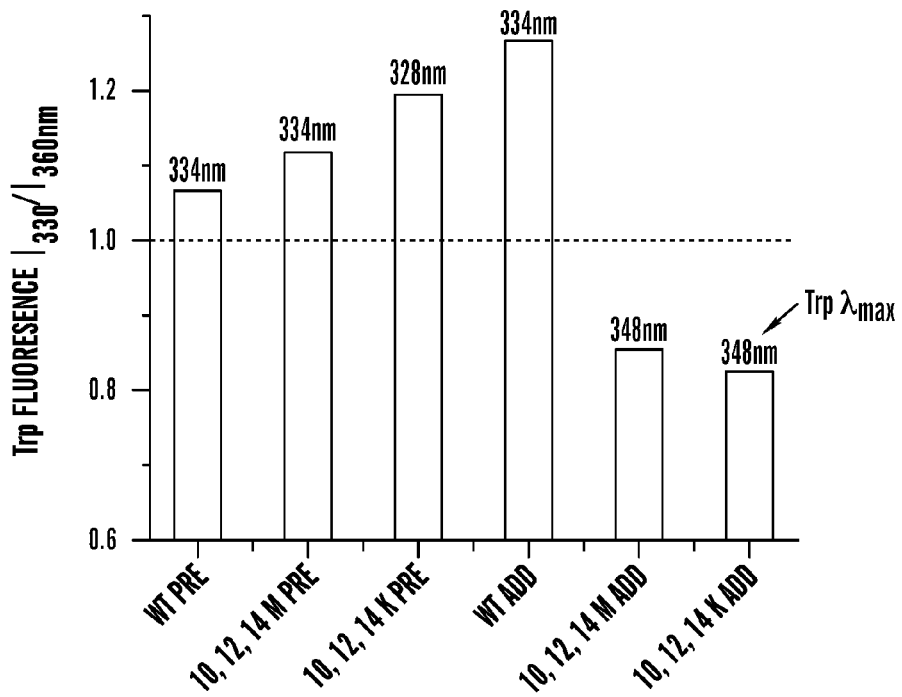
FIG. 17A shows peptide distribution in EYPC LUVs solutions determined by Trp fluorescence. I330/350 nm was shown as bars and the $\lambda_{em}$ was labeled on top. The premixed samples labeled as "pre" and samples with peptide added into LUVs solution labeled as "add.
Figure 17B:
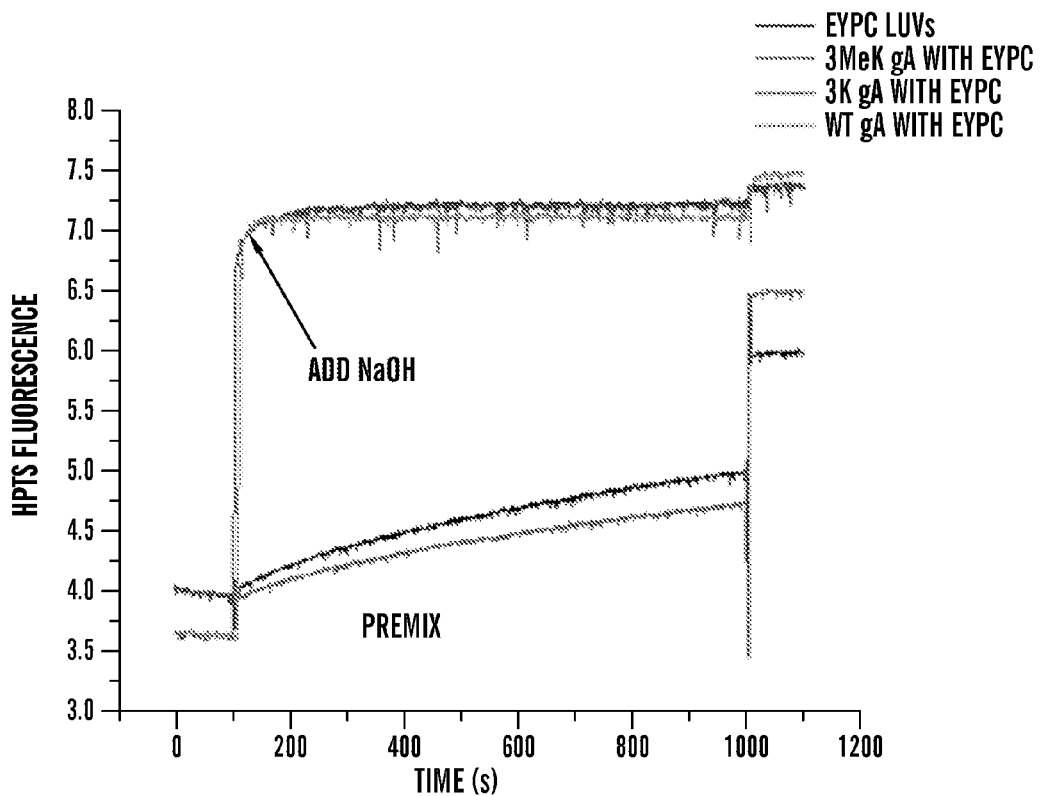
" FIG. 17B shows kinetic profile of proton leakage from EYPC vesicles monitored by a pH sensitive fluorophore HPTS.
Figure 18:
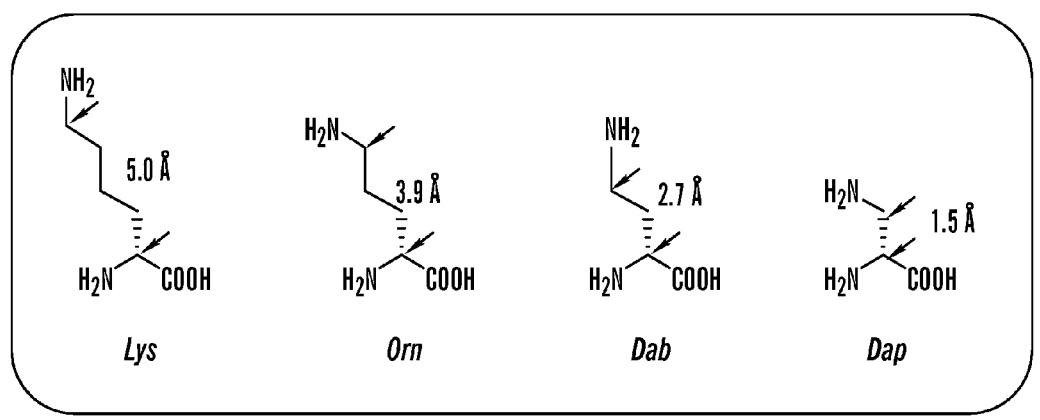
FIG. 18 depicts different lysine reside homologs that were tested. A detailed structure analysis of gA-WT shows that the α-carbon of AA10 is 5.0 Å from the tail of the peptide (the aqueous exposed portion), and along the z-axial to the N-terminal of gA channel, the distance decreases about 1.2 Å every other residues. Lys homologs with different side-chain lengths at the correct position (shown in the graph) were tested to determine whether they could provide a perfect hydrophobic match of the channel that would decrease the entropy cost in terms of ordering the carbon chain of Lys 14 or gain in the solvation energy that used to solublize the long carbon chain, and therefore, achieve a better channel.
Figure 18:
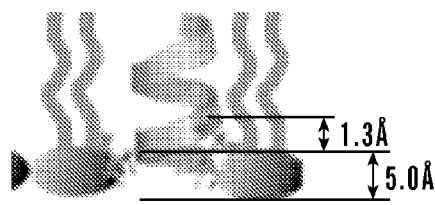
Figure 19:
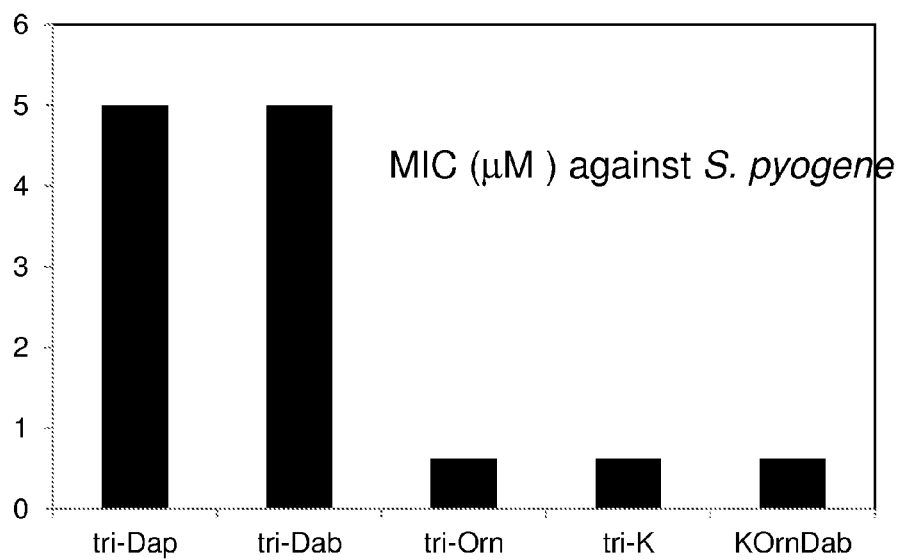
FIG. 19 demonstrates that short chain cationic charges substituted for lysine compromises gramicidin A channel formation, as seen by increases in MIC values, therefore demonstrating that long cationic side chains are necessary.
Figure 19:
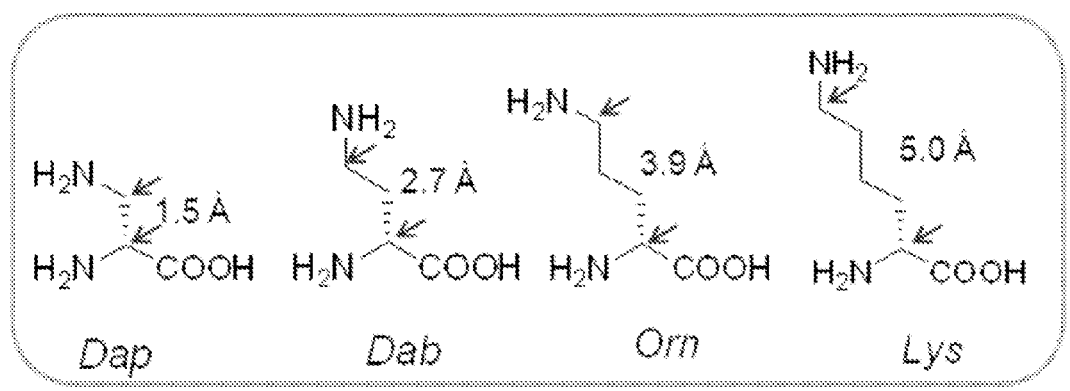
Figure 21:
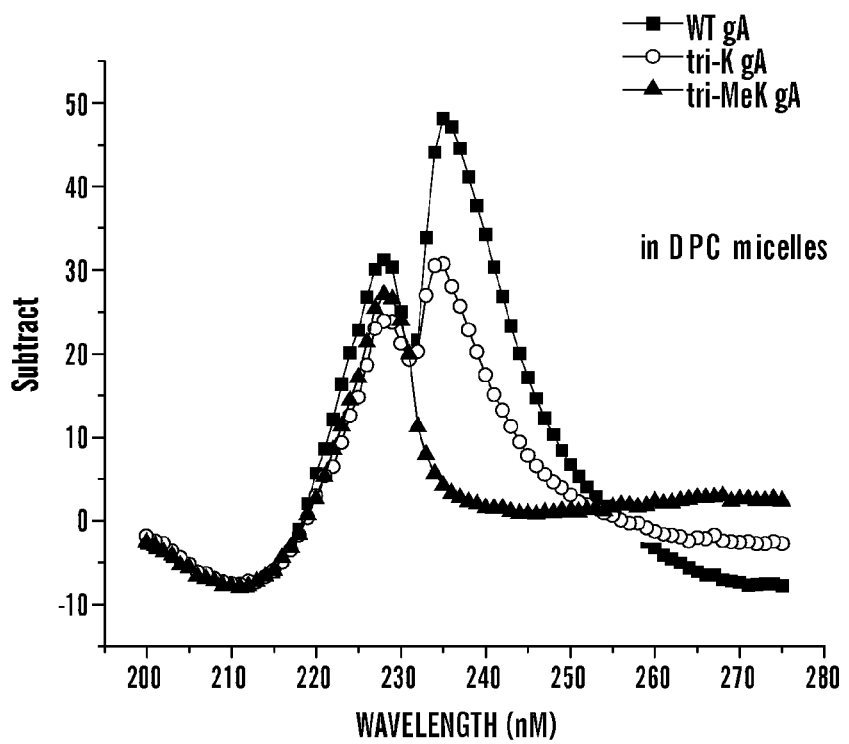
FIG. 21 demonstrates CD spectra of Gramicidin A-WT, Gramicidin-5 (10, 12, 14 K, triple lysine substituted gA) and tri-MeK Gramicidin variant in either neutral (DPC) or negatively charged (SDS) micelles. Peptide conc=100 uM; L/P ratio=50:1. Peptide was premixed with liposome and dried out completely. Peptide conformation equilibrium was promoted by sonication and 55° C. water bath (5 mins).
Figure 21:
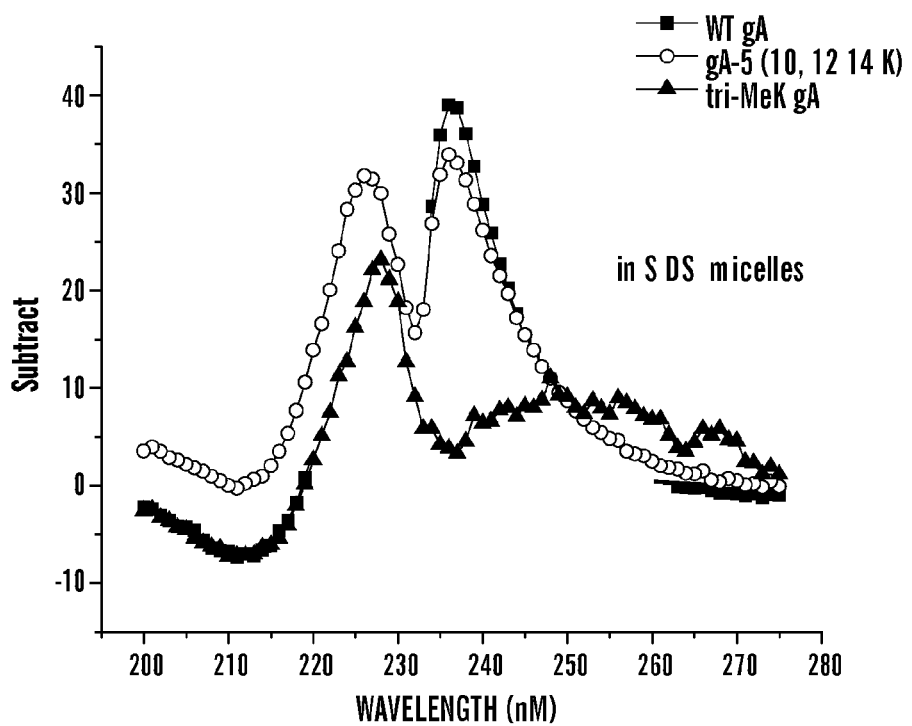

To confirm that lack of binding causes loss of membrane activity, we decided to premix the peptides and lipids in organic solvent and then dried out the mixture before hydration. Then, the peptides would be trapped into the bound form upon vesicle formation. The peptides distribution was determined by monitoring Trp fluorescence and the channel activity was determined by monitoring the proton leakage from LUVs using a pH sensitive fluorescence dye HPTS. Peptides 10, 12, 14K and 10, 12, 14 M gA were chosen to mix with neutral lipids EYPC. As neither of the two peptides showed any membrane activity upon addition to neutral vesicles, we could address the effect of premix more specifically. gA-WT was used as a control sample. Consistent with previous results, neither peptides bound to EYPC LUVs upon addition, but they were both trapped in a hydrophobic environment when premixed with lipids as suggested by blue shifting of Trp fluorescence (FIG. 17A). However, only 10, 12, 14 K caused proton leakage (FIG. 17B). This indicated that Lys Nε-trimethylation not only changed the binding profile but also alternated the structure of gA analogs. CD spectrum of 10, 12, 14M showed different signature from that gA-WT and 10, 12, 14K gA (FIG. 21).

In summary, the therapeutic utility or potential of solubilized gramicidin A as systemic antibiotics can be further fine tuned by Lys Nε-trimethylation. After side chain methylation, the gA mutants showed significantly decreased toxicity against human red blood cells. While their antibacterial activities were mildly affected, we gained 2-5 folds increase in therapeutic indices. Studies in model liposomal systems indicated that, Lys side chain methylation affects both the binding affinity between peptides and vesicles, and channel formation.

REFERENCES

[1] M. A. Fischbach, C. T. Walsh, Science 2009, 325, 1089-1093.
[2] a) R. E. Hancock, H. G. Sahl, Nat. Biotechnol. 2006, 24, 1551-1557; b) Z. Jiang, A. I. Vasil, L. Gera, M. L. Vasil, R.

S. Hodges, Chem. Biol. Drug Des. 2011, 77, 225-240; c) M. Torrent, J. Valle, M. V. Nogues, E. Boix, D. Andreu, Angew. Chem. 2011, 123, 1-5; Angew. Chem. Ind. Ed. 2011, 50, 1-5; d) R. Rathinakumar, W. F. Walkenhorst, W. C. Wimley, J. Am. Chem. Soc. 2009, 131, 7609-7617.

[3] a) E. A. Porter, X. Wang, H. S. Lee, B. Weisblum, S. H. Gellman, Nature 2000, 404, 565; b) S. Fernandez-Lopez, H. S. Kim, E. C. Choi, M. Delgado, J. R. Granja, A. Khasanov, K. Kraehenbuehl, G. Long, D. A. Weinberger, K. M. Wilcoxen, M. R. Ghadiri, Nature 2001, 412, 452-455; c) G. N. Tew, R. W. Scott, M. L. Klein, W. F. Degrado, Accounts. Chem. Res. 2010, 43, 30-39; d) N. P. Chongsiriwatana, J. A. Patch, A. M. Czyzewski, M. T. Dohm, A. Ivankin, D. Gidalevitz, R. N. Zuckermann, A. E. Barron, Proc. Natl. Acad. Sci. USA 2008, 105, 2794-2799; e) H. Meng, K. Kumar, J. Am. Chem. Soc. 2007, 129, 15615-15622; f) L. M. Gottler, H. Y. Lee, C. E. Shelburne, A. Ramamoorthy, E. N. Marsh, Chembiochem 2008, 9, 370-373; g) N. Srinivas, P. Jetter, B. J. Ueberbacher, M. Werneburg, K. Zerbe, J. Steinmann, B. Van der Meijden, F. Bernardini, A. Lederer, R. L. A. Dias, P. E. Misson, H. Henze, J. Zumbrunn, F. O. Gombert, D. Obrecht, P. Hunziker, S. Schauer, U. Ziegler, A. Käch, L. Eberl, K. Riedel, S. J. DeMarco, J. A. Robinson, Science 2010, 327, 1010-1013.

[4] a) M. Zasloff, Nature 2002, 415, 389-395; b) Y. Shai, Curr. Pharm. Desi. 2002, 8, 715-725.

[5] a) K. A. Brogden, Nat. Rev. Microbial. 2005, 3, 238-250; b) Y. Shai, Biochim. Biophy. Acta 1999, 1462, 55-70; c) H. W. Huang, Biochemistry 2000, 39, 8347-8352.

[6] a) A. K. Marr, W. J. Gooderham, R. E. Hancock, Curr. Opin. Pharmacol. 2006, 6, 468-472; b) L. Zhang, J. Parente, S. M. Harris, D. E. Woods, R. E. Hancock, T. J. Falla, Antimicrob. Agents Chemother. 2005, 49, 2921-2927; c) A. Giuliani, G. Pirri, S. F. Nicoletto, Cent. Eur. J. Biol. 2007, 2, 1-33.

[7] A. Som, L. Yang, G. C. Wong, G. N. Tew, J. Am. Chem. Soc. 2009, 131, 15102-15103.

[8] D. A. Kelkar, A. Chattopadhyay, Biochim. Biophy. Acta 2007, 1768, 2011-2025.

[9] R. R. Ketcham, K. C. Lee, S. Huo, T. A. Cross, J. Biomol. NMR 1996, 8, 1-14.

[10] a) J. R. Pfeifer, P. ReiB, U. Koert, Angew. Chem. Ind. Ed. 2006, 45, 501-504; b) M. X. Macrae, S. Blake, M. Mayer, J. Yang, J. Am. Chem. Soc. 2010, 132, 1766-1767; c) S. Majd, E. C. Yusko, A. D. MacBriar, J. Yang, M. Mayer, J. Am. Chem. Soc. 2009, 131, 16119-16126; d) G. A. Woolley, A. S. I. Jaikaran, Z. Zhang, S. Peng, J. Am. Chem. Soc. 1995, 117, 4448-4454.

[11] a) F. M. Harold, J. R. Baarda, J. Bacteriol. 1967, 94, 53-60; b) T. Hamada, S. Matsunaga, M. Fujiwara, K. Fujita, H. Hirota, R. Schmucki, P. Guntert, N. Fusetani, J. Am. Chem. Soc. 2010, 132, 12941-12945.

[12] a) T. Hessa, N. M. Meindl-Beinker, A. Bernsel, H. Kim, Y. Sato, M. Lerch-Bader, I. Nilsson, S. H. White, G. von Heijne, Nature 2007, 450, 1026-1030; b) J. A. Killian, G. von Heijne, Trends Biochem. Sci. 2000, 25, 429-434.

[13] I. Wiegand, K. Hilpert, R. E. W. Hancock, Nat. Protocols 2008, 3, 163-175.

[14] a) G. N. Moll, V. van den Eertwegh, H. Tournois, B. Roelofsen, J. A. Op den Kamp, L. L. van Deenen, Biochim. Biophys. Acta 1991, 1062, 206-210; b) C. H. Rammelkamp, L. Weinstein, J. Infect. Dis. 1942, 71, 166-173.

[15] A. Cherkasov, K. Hilpert, H. Jenssen, C. D. Fjell, M. Waldbrook, S. C. Mullaly, R. Volkmer, R. E. Hancock, ACS Chem. Biol. 2009, 4, 65-74.

[16] G. N. Bowers, R. A. Velapoldi, N. M. L. (U.S.), NBS special publication, 260-63, 1979.

[17] D. T. Vistica, P. Skehan, D. Scudiero, A. Monks, A. Pittman, M. R. Boyd, Cancer Res. 1991, 51, 2515-2520

[18] a) W. C. Wimley, S. H. White, Nat Struct Biol 1996, 3, 842-848; b) M. Tang, A. J. Waring, M. Hong, J. Am. Chem. Soc. 2007, 129, 11438-11446.

[19] Y. Shai, Biopolymers 2002, 66, 236-248.

[20-1] Denise V. Greathouse and Roger E. Koeppe, Methods in Enzymology, 1999, 294, 525-550.

[20-2] I. Wiegand, K. Hilpert & R. E W Hancock. Natural Protocols, 2008, 3, 163-175.

[20-3] H. Meng, K. Kumar, J. Am. Chem. Soc. 2007, 129, 15615-15622.

[20-4] G. N. Bowers, R. A. Velapoldi, N. M. L. (U.S.), NBS special publication, 260-63, 1979

[20-5] a) D. T. Vistica, P. Skehan, D. Scudiero, A. Monks, A. Pittman, M. R. Boyd, Cancer Res. 1991, 51, 2515-2520; b) Vybrant® MTT Cell Proliferation Assay Kit (V-13154) technical manual.

[20-6] J. Charles and M. Stewart, Anal. Biochem., 1980, 104, 10-14

[20-7] R. Rathinakumar and W. C. Wimley. J. Am. Chem. Soc, 2008, 130, 9849-9858

[20-8] A. R. Jude, D. V. Greathouse, R. E. Koeppe H, L. L. Providence and O. S. Andersen. Biochemistry, 1999, 38, 1030-1039

We claim:

1. An anti-microbial composition comprising at least one Gramicidin A peptide analog or derivative having reduced cytotoxicity and increased solubility relative to wild-type Gramicidin A wherein the wild-type Gramicidin A comprises the amino acid sequence of SEQ ID NO: 2, and wherein the at least one Gramicidin A peptide analog or derivative comprises the amino acid sequence of SEQ ID NO: 2, wherein one of the d-Leucine amino acids at positions 10 or 14 of the SEQ ID NO: 2 have been replaced or substituted with a cationic residue.

2. The anti-microbial composition of claim 1, wherein the at least one Gramicidin A peptide analog or derivative comprises the amino acid sequence of SEQ ID NO: 2 having both of the d-Leucine amino acids at positions 10, and 14 replaced or substituted with a cationic residue.

3. The anti-microbial composition of claim 1, wherein the cationic amino acid is d-lysine or d-arginine.

4. The anti-microbial composition of claim 1, wherein the solubility of the Gramicidin A peptide analog or derivative is increased relative to wild-type Gramicidin A by at least 10-fold.

5. The anti-microbial composition of claim 1, wherein the cytotoxicity of the Gramicidin A peptide analog or derivative is reduced relative to wild-type Gramicidin A by at least 2-fold.

6. The anti-microbial composition of claim 1, wherein the at least one Gramicidin A peptide analog or derivative comprises an amino acid sequence of SEQ ID NO: 3.

7. The anti-microbial composition of claim 1, wherein the at least one Gramicidin A peptide analog or derivative comprises an amino acid sequence of SEQ ID NO: 4.

8. An anti-microbial composition comprising at least one Gramicidin A peptide analog or derivative having reduced cytotoxicity and increased solubility relative to wild-type Gramicidin A wherein the wild-type Gramicidin A comprises the amino acid sequence of SEQ ID NO: 2, and wherein the at least one Gramicidin A peptide analog or derivative comprises the amino acid sequence of SEQ ID NO: 2, wherein two or more of the d-Leucine amino acids at positions 10, 12, or 14 of the SEQ ID NO: 2 have been replaced or substituted with a cationic residue.

9. The anti-microbial composition of claim 8, wherein the cationic amino acid is d-lysine or d-arginine.

10. The anti-microbial composition of claim 8, wherein the solubility of the Gramicidin A peptide analog or derivative is increased relative to wild-type Gramicidin A by at least 10-fold.

11. The anti-microbial composition of claim 8, wherein the cytotoxicity of the Gramicidin A peptide analog or derivative is reduced relative to wild-type Gramicidin A by at least 2-fold.

12. The anti-microbial composition of claim 8, wherein the d-Leucine amino acid at position 10 is replaced or substituted with Nε-trimethylated lysine.

13. The anti-microbial composition of claim 8, wherein the d-Leucine amino acid at position 14 is replaced or substituted with Nε-trimethylated lysine.

14. The anti-microbial composition of claim 8, wherein the d-Leucine amino acid at positions 10 and 14 are replaced or substituted with Nε-trimethylated lysine.

15. The anti-microbial composition of claim 8, further comprising a pharmaceutically acceptable carrier.

16. The anti-microbial composition of claim 8, wherein the at least one Gramicidin A peptide analog or derivative comprises an amino acid sequence of SEQ ID NO: 5.

17. The anti-microbial composition of claim 8, wherein the at least one Gramicidin A peptide analog or derivative comprises an amino acid sequence of SEQ ID NO: 6.

18. The anti-microbial composition of claim 8, wherein the at least one Gramicidin A peptide analog or derivative comprises an amino acid sequence of SEQ ID NO: 7.

19. The anti-microbial composition of claim 8, wherein the at least one Gramicidin A peptide analog or derivative comprises an amino acid sequence of SEQ ID NO: 8.

20. The anti-microbial composition of claim 1, wherein the d-Leucine amino acid at position 10 is replaced or substituted with Nε-trimethylated lysine.

21. The anti-microbial composition of claim 1, wherein the d-Leucine amino acid at position 14 is replaced or substituted with Nε-trimethylated lysine.

22. The antimicrobial composition of claim 8, wherein the d-Leucine amino acid at positions 10 and 14 are replaced or substituted with Nε-trimethylated lysine.

23. The anti-microbial composition of claim 1, further comprising a pharmaceutically acceptable carrier.

24. A method of inhibiting growth or replication of a microorganism, the method comprising contacting a biological sample or a surface found in a medical environment with the anti-microbial composition of claim 1 in an amount sufficient to inhibit growth or replication of the microorganism.

25. The method of claim 24, wherein the microorganism is a bacterium.

26. A method of treating or inhibiting a microbial infection in a subject having or at risk for a microbial infection, comprising administering to the subject a therapeutically effective amount of the anti-microbial composition of claim 1.

27. The method of claim 26, wherein the microbial infection is a bacterial infection.

28. A method of inhibiting growth or replication of a microorganism, the method comprising contacting a biological sample or a surface found in a medical environment with the anti-microbial composition of claim 8 in an amount sufficient to inhibit growth or replication of the microorganism.

29. The method of claim 15, wherein the microorganism is a bacterium.

30. A method of treating or inhibiting a microbial infection in a subject having or at risk for a microbial infection, comprising administering to the subject a therapeutically effective amount of the anti-microbial composition of claim 8.

31. The method of claim 30, wherein the microbial infection is a bacterial infection.

* * * * *

SEQUENCE LISTING

```
<160> NUMBER OF SEQ ID NOS: 8

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (1)..(1)
<223> OTHER INFORMATION: Val or Ile
<220> FEATURE:
<221> NAME/KEY: MOD_RES
<222> LOCATION: (4)..(4)
<223> OTHER INFORMATION: D-amino acid
```

```
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (11)..(11)
<223> OTHER INFORMATION: Trp, Phe or Tyr
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 1

Xaa Gly Ala Leu Ala Val Val Val Trp Leu Xaa Leu Leu Trp Leu Trp
1               5                   10                  15

<210> SEQ ID NO 2
<211> LENGTH: 15
<212> TYPE: PRT
<213> ORGANISM: Bacillus brevis
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 2

Val Gly Ala Leu Ala Val Val Val Trp Leu Trp Leu Trp Leu Trp
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 3

Val Gly Ala Leu Ala Val Val Val Trp Lys Trp Leu Trp Leu Trp
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 4

Val Gly Ala Leu Ala Val Val Val Trp Leu Trp Leu Trp Lys Trp
1               5                   10                  15

<210> SEQ ID NO 5
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 5

Val Gly Ala Leu Ala Val Val Val Trp Lys Trp Leu Trp Lys Trp
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 6

Val Gly Ala Leu Ala Val Val Val Trp Lys Trp Lys Trp Leu Trp
```

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<223> OTHER INFORMATION: C-term NHCH2CH2OH

<400> SEQUENCE: 7

Val Gly Ala Leu Ala Val Val Val Trp Lys Trp Lys Trp Lys Trp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term formyl
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:

-continued

<223> OTHER INFORMATION: C-term NHCH2CH2OH

<400> SEQUENCE: 8

Val Gly Ala Leu Ala Val Val Val Trp Arg Trp Arg Trp Arg Trp
1               5                   10                  15